United States Patent
Mahfouz

(10) Patent No.: US 11,331,151 B2
(45) Date of Patent: May 17, 2022

(54) SURGICAL NAVIGATION OF THE HIP USING FLUOROSCOPY AND TRACKING SENSORS

(71) Applicant: TechMah Medical LLC, Knoxville, TN (US)

(72) Inventor: Mohamed R. Mahfouz, Knoxville, TN (US)

(73) Assignee: TECHMAH MEDICAL LLC, Knoxville, TN (US)

( * ) Notice: Subject to any disclaimer, the term of this patent is extended or adjusted under 35 U.S.C. 154(b) by 0 days.

(21) Appl. No.: 16/012,718

(22) Filed: Jun. 19, 2018

(65) Prior Publication Data

US 2019/0133693 A1 May 9, 2019

Related U.S. Application Data

(60) Provisional application No. 62/617,383, filed on Jan. 15, 2018, provisional application No. 62/575,905, (Continued)

(51) Int. Cl.
*A61B 34/20* (2016.01)
*A61B 34/10* (2016.01)
(Continued)

(52) U.S. Cl.
CPC .......... *A61B 34/20* (2016.02); *A61B 5/11* (2013.01); *A61B 5/1114* (2013.01); *A61B 6/12* (2013.01);
(Continued)

(58) Field of Classification Search
None
See application file for complete search history.

(56) References Cited

U.S. PATENT DOCUMENTS 5,951,475 A * 9/1999 Gueziec ............... G06T 3/0068
128/922
8,007,448 B2 * 8/2011 Moctezuma de La Barrera .........
A61B 34/20
600/426

(Continued)

FOREIGN PATENT DOCUMENTS

JP 2006527620 12/2006
JP 2007518540 7/2007
(Continued)

OTHER PUBLICATIONS

Hu et al., "Learning 3D Object Templates by Quantizing Geometry and Appearance Spaces", IEEE Transactions on Pattern Analysis and Machine Intelligence, 2015, pp. 1-17.

*Primary Examiner* — Jason A Pringle-Parker
(74) *Attorney, Agent, or Firm* — Allen, Dyer, Doppelt + Gilchrist, P.A.

(57) ABSTRACT

A method of tracking motion of a body part, the method comprising: (a) gathering motion data from a body part repositioned within a range of motion, the body part having mounted thereto a motion sensor; (b) gathering a plurality of radiographic images taken of the body part while the body part is in different positions within the range of motion, the plurality of radiographic images having the body part and the motion sensor within a field of view; and, (c) constructing a virtual three dimensional model of the body part from the plurality of radiographic images using a structure of the motion sensor identifiable within at least two of the plurality of radiographic images to calibrate the radiographic images.

13 Claims, 55 Drawing Sheets

Related U.S. Application Data filed on Oct. 23, 2017, provisional application No. 62/521,582, filed on Jun. 19, 2017.

(51) Int. Cl.

| | |
|---|---|
| *A61B 6/12* | (2006.01) |
| *A61B 6/00* | (2006.01) |
| *A61B 5/11* | (2006.01) |
| *A61B 34/00* | (2016.01) |
| *G06T 7/579* | (2017.01) |
| *G06T 17/00* | (2006.01) |
| *G06T 19/20* | (2011.01) |
| *A61B 6/04* | (2006.01) |
| *A61B 90/00* | (2016.01) |
| *G06K 9/62* | (2006.01) |
| *G06V 10/75* | (2022.01) |

(52) U.S. Cl.
CPC ............ *A61B 6/487* (2013.01); *A61B 6/505* (2013.01); *A61B 6/5229* (2013.01); *A61B 6/5241* (2013.01); *A61B 34/10* (2016.02); *A61B 34/25* (2016.02); *G06T 7/579* (2017.01); *G06T 17/00* (2013.01); *G06T 19/20* (2013.01); *A61B 6/0492* (2013.01); *A61B 6/582* (2013.01); *A61B 2034/104* (2016.02); *A61B 2034/105* (2016.02); *A61B 2034/107* (2016.02); *A61B 2034/108* (2016.02); *A61B 2034/2048* (2016.02); *A61B 2034/2051* (2016.02); *A61B 2034/2065* (2016.02); *A61B 2090/364* (2016.02); *A61B 2090/367* (2016.02); *A61B 2090/3966* (2016.02); *A61B 2560/0223* (2013.01); *G06T 2207/10016* (2013.01); *G06T 2207/10116* (2013.01); *G06T 2207/30008* (2013.01); *G06T 2210/41* (2013.01); *G06T 2219/2004* (2013.01); *G06T 2219/2016* (2013.01); *G06V 10/751* (2022.01); *G06V 2201/03* (2022.01)

(56) References Cited

U.S. PATENT DOCUMENTS

| | | | | |
|---|---|---|---|---|
| 8,025,632 B2* | 9/2011 | Einarsson | .......... | A41D 13/1281 |
| | | | | 602/23 |
| 9,924,921 B1* | 3/2018 | Irish | ....... | A61B 7/006 |
| 10,111,595 B2* | 10/2018 | Wundrak | ....... | A61C 7/002 |
| 2003/0191394 A1 | 10/2003 | Simon et al. | | |
| 2006/0155189 A1 | 7/2006 | Lavallee et al. | | |
| 2006/0251300 A1 | 11/2006 | Borgert et al. | | |
| 2008/0221487 A1* | 9/2008 | Zohar | ......... | A61B 5/103 |
| | | | | 600/595 |
| 2010/0008559 A1* | 1/2010 | Borghese | ...... | G06T 11/006 |
| | | | | 382/132 |
| 2010/0198067 A1 | 8/2010 | Mahfouz et al. | | |
| 2011/0082367 A1* | 4/2011 | Regazzoni | ......... | A61B 90/36 |
| | | | | 600/425 |
| 2011/0103674 A1* | 5/2011 | Chang | ........ | G06K 9/00 |
| | | | | 382/132 |
| 2012/0106819 A1* | 5/2012 | Fernandez Oca | ...... | A61B 34/10 |
| | | | | 382/132 |
| 2013/0244211 A1* | 9/2013 | Dowling | ......... | G06F 19/3481 |
| | | | | 434/247 |
| 2014/0025348 A1* | 1/2014 | Abiven | ........ | A61B 17/155 |
| | | | | 703/1 |
| 2014/0221825 A1 | 8/2014 | Mahfouz et al. | | |
| 2014/0277451 A1* | 9/2014 | Ganz | ......... | A61F 2/3872 |
| | | | | 623/14.12 |
| 2015/0094564 A1* | 4/2015 | Tashman | ......... | A61B 6/12 |
| | | | | 600/424 |
| 2015/0148653 A1* | 5/2015 | Fleig | ........ | A61B 5/1072 |
| | | | | 600/407 |
| 2016/0103489 A1 | 4/2016 | Cruz-Hernandez et al. | | |
| 2016/0157751 A1 | 6/2016 | Mahfouz | | |
| 2016/0302721 A1* | 10/2016 | Wiedenhoefer | ...... | A61B 5/1071 |
| 2017/0000386 A1* | 1/2017 | Salamatian | ......... | A61B 5/742 |
| 2017/0143494 A1 | 5/2017 | Mahfouz | | |
| 2017/0296115 A1 | 10/2017 | Mahfouz et al. | | |
| 2018/0089841 A1* | 3/2018 | Dai | ....... | G01P 15/18 |

FOREIGN PATENT DOCUMENTS

| | | |
|---|---|---|
| JP | 2009505708 | 2/2009 |
| JP | 2009131632 | 6/2009 |
| JP | 2014025791 | 2/2014 |
| WO | 0222014 | 3/2002 |
| WO | 2008142629 | 11/2008 |
| WO | 2012127353 | 9/2012 |
| WO | 2016148968 | 9/2016 |
| WO | 20180236936 | 11/2018 |
| WO | 20180236936 A1 | 12/2018 |

* cited by examiner

FIG. 7
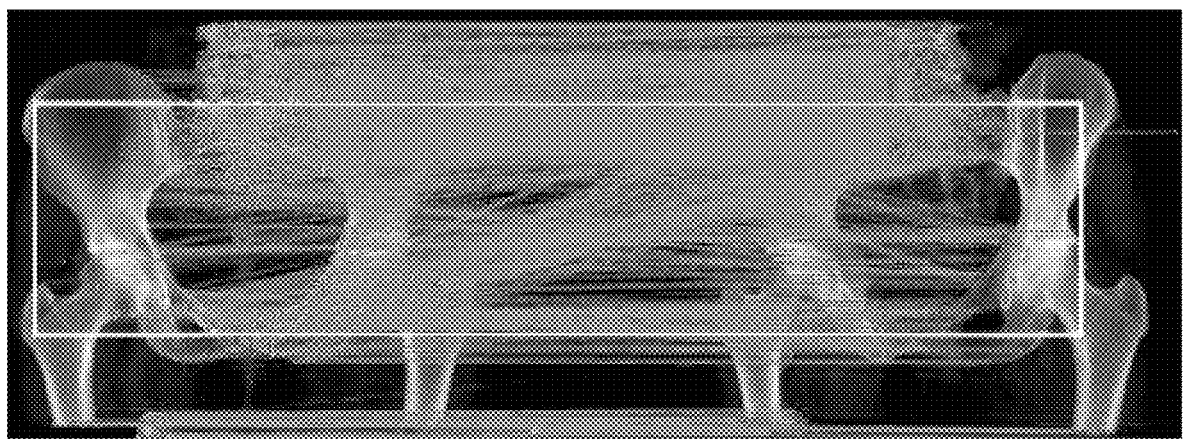
FIG. 8

FIG. 12
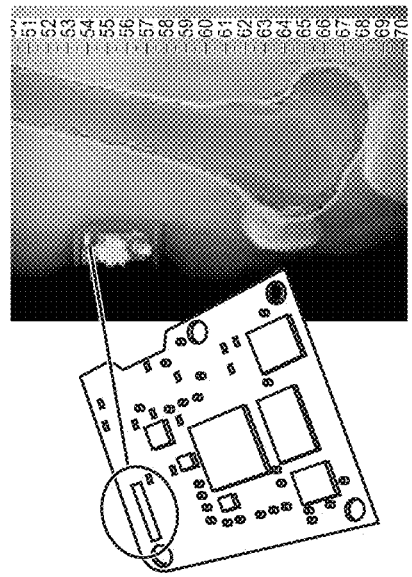
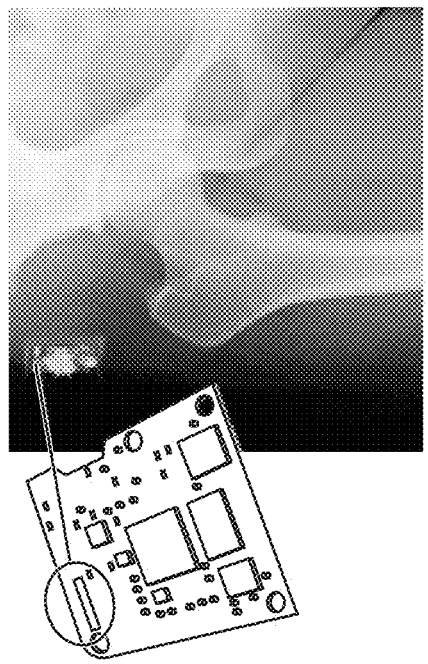
FIG. 13

TABLE 1 EVALUATION SCORE FUNCTION

ALGORITHM EVALUATE SCORE

INPUT: SHAPE PARAMETERS θ, FLUORO IMAGE
OUTPUT: SCORE
1: INITIALIZE SCORE=0;
2: RENDER THE RECONSTRUCTED SURFACE MODEL (θ) ON 2D;
3: FOR i=1:9
4: CALCULATE EDGE SCORE (e) OF THE iTH FLUORO IMAGE;
5: CALCULATE REGION SCORE (r) OF THE iTH FLUORO IMAGE;
6: SCORE = SCORE + 0.82*e + 0.12*r;
7: END FOR $$d_0^2 = \left[ \|z_0\|^2 \cdots \|z_n\|^2 \right]'$$

$$d_{ij}^2 = -2\sigma^2 \log\left( \frac{1}{2}(K_{ii} + K_{jj} - \tilde{d}_{ij}^2) \right)$$

LEAST SQUARE SOLUTION $$\hat{z} = -\frac{1}{2} \Lambda^{-1} V'(d^2 - d_0^2)$$

PROJECT BACK TO THE ORIGINAL COORDINATE SYSTEM $\quad \hat{x} = U\hat{z} + \bar{x}$

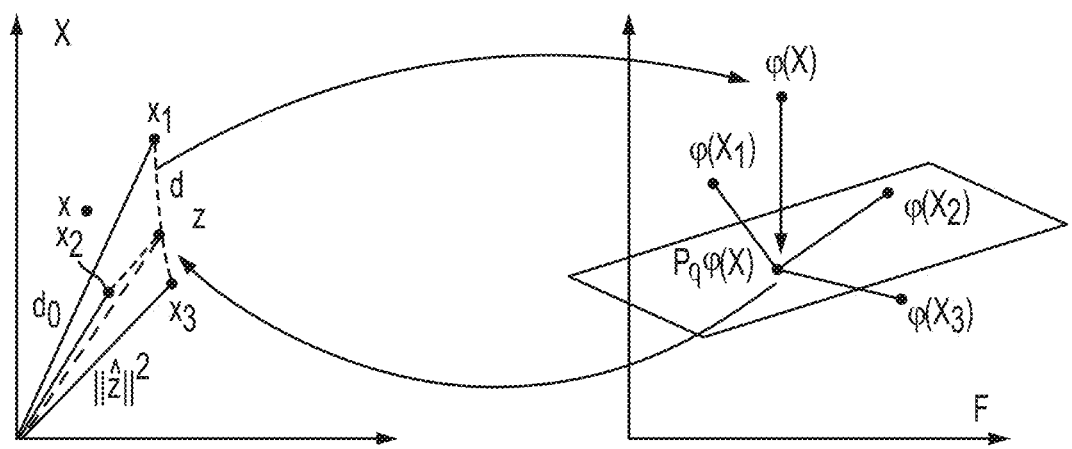

FIG. 18

 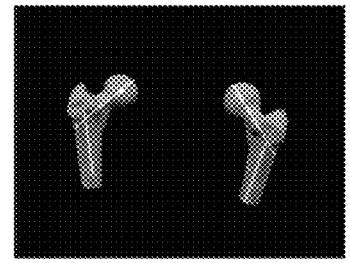
FIG. 19
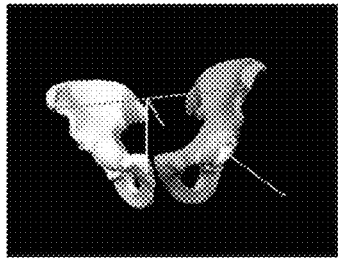 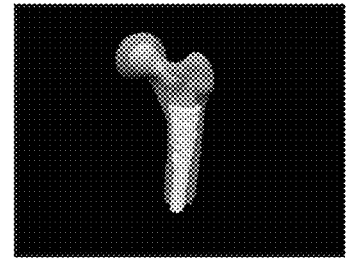
FIG. 20
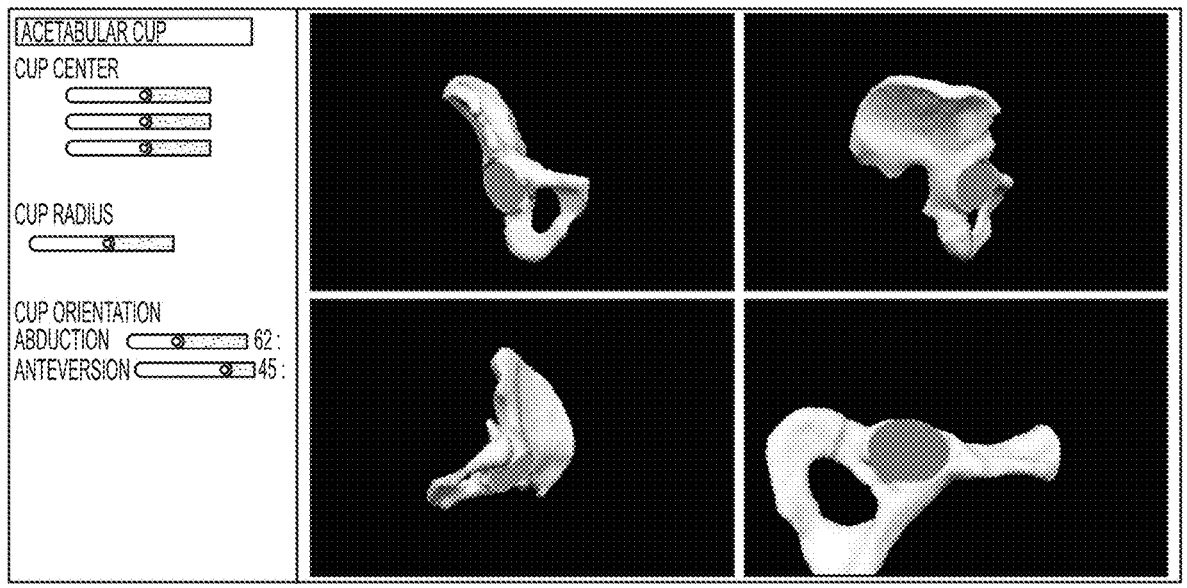
FIG. 21

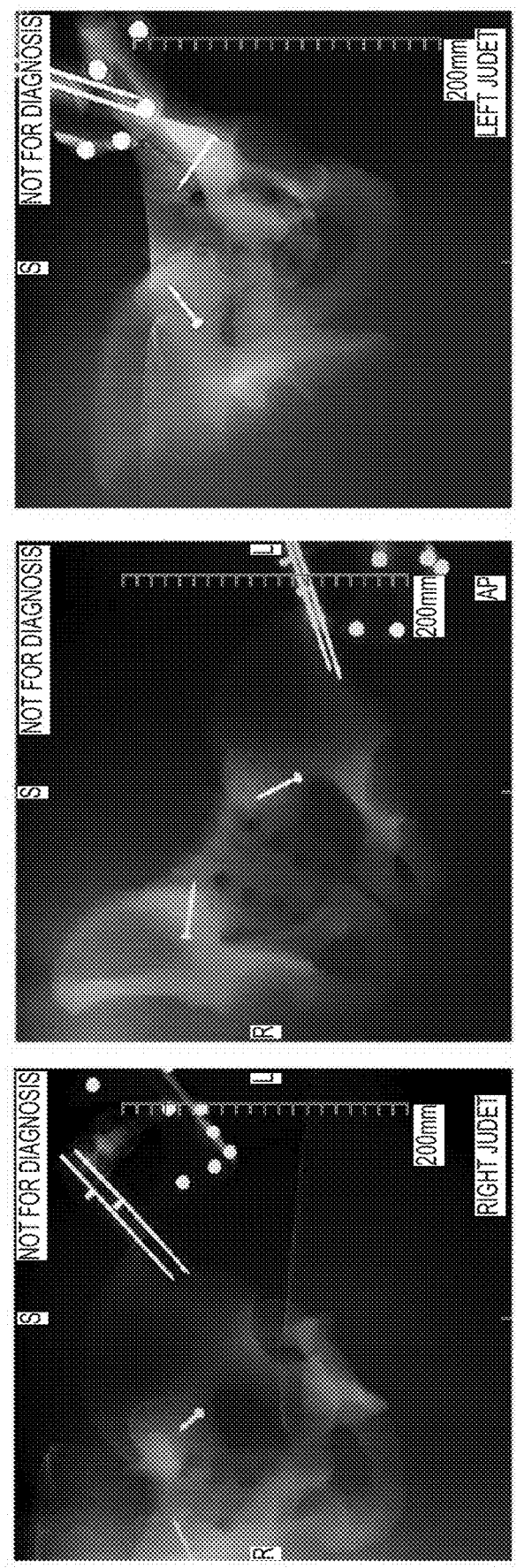

TABLE 2 EVALUATION SCORE FUNCTION

ALGORITHM EVALUATE SCORE

INPUT: SHAPE PARAMETERS θ, FLUORO IMAGE
OUTPUT: SCORE
1: INITIALIZE SCORE=0;
2: RENDER THE RECONSTRUCTED SURFACE MODEL (θ) ON 2D;
3: FOR i=1:9
4: CALCULATE EDGE SCORE (e) OF THE iTH FLUORO IMAGE;
5: CALCULATE REGION SCORE (r) OF THE iTH FLUORO IMAGE;
6: SCORE = SCORE + 0.82*e + 0.12*r;
7: END FOR $$d_0^2 = \left[ \|Z_0\|^2 \cdots \|Z_n\|^2 \right]'$$

$$d_{ij}^2 = -2\sigma^2 \log\left( \frac{1}{2}(K_{ii} + K_{jj} - \tilde{d}_{ij}^2) \right)$$

LEAST SQUARE SOLUTION $$\hat{z} = -\frac{1}{2}\Lambda^{-1} V'(d^2 - d_0^2)$$

PROJECT BACK TO THE ORIGINAL COORDINATE SYSTEM    $\hat{x} = U\hat{z} + \bar{x}$

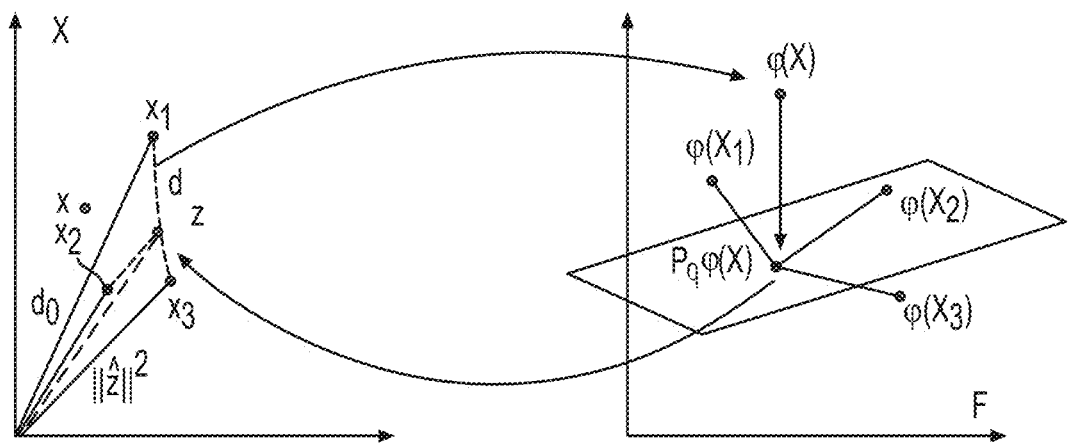

FIG. 64

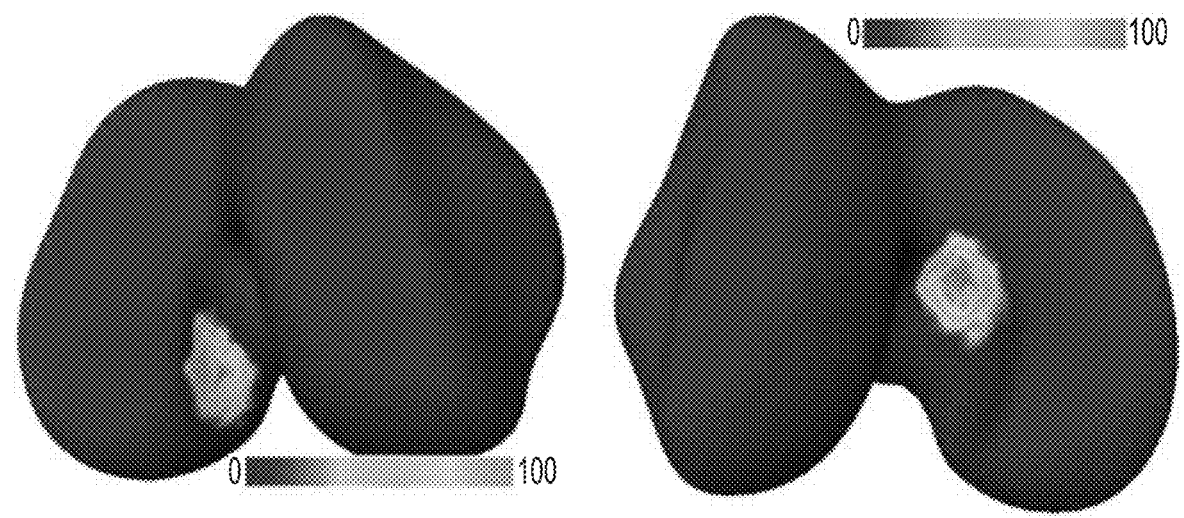
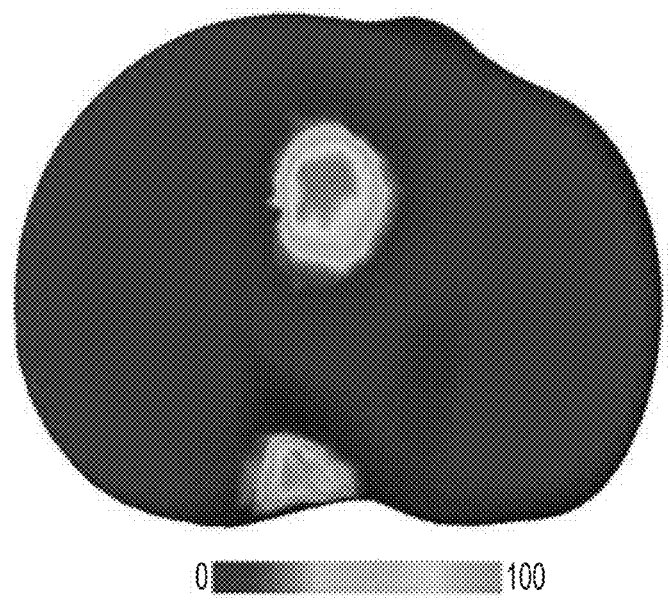
*FIG. 75*

SURGICAL NAVIGATION OF THE HIP USING FLUOROSCOPY AND TRACKING SENSORS

CROSS REFERENCE TO RELATED APPLICATIONS

The present application claims the benefit of U.S. Provisional Patent Application Ser. No. 62/521,582, titled "Surgical Navigation of the Hip using Fluoroscopy and Tracking Sensors," filed Jun. 19, 2017, and claims the benefit of U.S. Provisional Patent Application Ser. No. 62/575,905, titled "Surgical Navigation of the Hip using Fluoroscopy and Tracking Sensors," filed Oct. 23, 2017, and claims the benefit of U.S. Provisional Patent Application Ser. No. 62/617,383, titled "Surgical Navigation of the Hip using Fluoroscopy and Tracking Sensors," filed Jan. 15, 2018, the disclosure of each of which is incorporated herein by reference.

INTRODUCTION TO THE INVENTION

Computed tomography (CT) or magnetic resonance imaging (MRI) are generally considered the gold standard for joint imaging, specifically in applications requiring a virtual anatomical model. The images can be used by segmentation software to perform three dimensional (3D) reconstruction, the output of which is a surface model of the patient's joint. These models may include bone, cartilage, other soft tissues or any combination. Hence, these 3D models are used frequently in modern surgical navigation and guidance systems for total joint replacement surgery. However, creation of these models is often time consuming, resulting in increased costs and often significant time between imaging and surgery. A more cost-effective method of imaging is one that requires no off-site reconstruction, utilizes existing office-based imaging, for example standard X-Rays or fluoroscopy, while still providing a pathway for 3D model creation to be used in planning or surgery. As part of this disclosure, the 3D model and imaging may be used in intraoperative registration to decrease surgical time and reduce additional costs.

One difficult process related to using surgical navigation and guidance systems intraoperatively is registering the patient's joint locations and orientation to the navigation system. This is usually performed via registering the location of bony landmarks on the patient under the surveillance of the guidance system, where the joint positions and orientations can be calibrated to the system. Traditionally this is done manually in the operating room, is time consuming, and potentially inaccurate.

A technique has been developed for utilizing patient specific instrument for registration, where the instrument is made to fit to the patient's bone in a unique fashion. The instrument may be additively manufactured and sterilized for the patient. Several challenges are present in this process. The first one is related to manufacturing. Some patients may not have the ideal bony geometry that can uniquely 'lock' to the patient-specific instrument, which may introduce registration errors. In addition, due to the nature of additive manufacturing, the material is often porous, which may affect the tolerance of the instrument depending on the moisture level. Another issue is the high cost and lead-time required to manufacture these instruments. Often an engineer is needed to perform segmentation, analyze the joint geometry to create the locking mechanism of the instrument to the patient joint, which may take weeks to accomplish depending on the volume. As part of this disclosure, a novel registration technique is presented with medical imaging to avoid the need to manufacture any additional devices.

By coupling intraoperative radiography imaging with an inertial tracking system, the patient can be registered in the operating room without the overhead of manufacturing patient specific instrument or manually identifying landmarks.

It is a first aspect of the present invention to provide a method of tracking motion of a body part, the method comprising: (a) gathering motion data from a body part repositioned within a range of motion, the body part having mounted thereto a motion sensor; (b) gathering a plurality of radiographic images taken of the body part while the body part is in different positions within the range of motion, the plurality of radiographic images having the body part and the motion sensor within a field of view; and, (c) constructing a virtual three dimensional model of the body part from the plurality of radiographic images using a structure of the motion sensor identifiable within at least two of the plurality of radiographic images to calibrate the radiographic images.

In a more detailed embodiment of the first aspect, the motion sensor comprises an inertial measurement unit. In yet another more detailed embodiment, the inertial measurement unit comprises a plurality of accelerometers, a plurality of gyroscopes, and a plurality of magnetometers. In a further detailed embodiment, the motion sensor is mounted non-rigidly to the body part. In still a further detailed embodiment, the motion sensor is mounted outside an epidermis at least partially covering the body part. In a more detailed embodiment, the motion sensor is mounted rigidly to the body part. In a more detailed embodiment, the structure of the motion sensor comprises at least one of a resistor, a chip, a capacitor, a circuit board, and an electrical lead. In another more detailed embodiment, the radiographic image comprises an X-ray. In yet another more detailed embodiment, the radiographic image comprises a fluoroscopic image. In still another more detailed embodiment, calibrating the radiographic images is performed automatically.

In yet another more detailed embodiment of the first aspect, the automatic calibration of the radiographic images is performed by a computer running a software program. In yet another more detailed embodiment, the method further includes gathering data from the motion sensor that may be used to determine at least one of position and rotation of the motion sensor as a function to time. In a further detailed embodiment, the data gathered from the motion sensor is gathered wirelessly. In still a further detailed embodiment, the data gathered from the motion sensor is gathered from a wire connected to the motion sensor. In a more detailed embodiment, the data gathered from the motion sensor is gathered by at least one of a phone, a computer, a tablet, and a portable memory. In a more detailed embodiment, the method further includes registering in three dimensional space the motion sensor to the virtual three dimensional model of the body part, and correlating gathered data from the motion sensor as a function of position of the body part to create a virtual dynamic model of the body part that is repositionable to reflect actual positions of the body part when repositioned within the range of motion. In another more detailed embodiment, the method further includes constructing a virtual three dimensional model of the motion sensor using the plurality of radiographic images. In yet another more detailed embodiment, the virtual three dimensional model of the motion sensor is integrated into the virtual three dimensional model of the body part to create a virtual three dimensional combined model. In still another more detailed embodiment, the method further includes correlating gathered data from the motion sensor as a function of position of the body part to provide dynamic movement to the virtual three dimensional combined model.

In a more detailed embodiment of the first aspect, gathering the motion data includes recording at least one of changes in position and rotation of the motion sensor as a function of time. In yet another more detailed embodiment, gathering the motion data includes recording changes acceleration of the motion sensor as a function of time. In a further detailed embodiment, the method further includes displaying the virtual three dimensional model of the body part to reflect changes in position of the actual body part in real time. In still a further detailed embodiment, the motion data gathered is time stamped.

It is a second aspect of the present invention to provide a system for tracing motion of a body part, the system comprising: (a) a motion sensor; (b) a processor configured to be communicatively coupled to the motion sensor, the processor communicatively coupled to a plurality of modules, the modules comprising: (i) a data reception module configured to record motion data generated by the motion sensor, at least one of the data reception module and the motion sensor time stamping the motion data generated by the motion sensor; (ii) a radiographic image processing module configured to identify a common feature visible across a plurality of radiographic images in order to calibrate the plurality of radiographic images; and, (iii) a three dimensional model module configured to process a plurality of radiographic images and create a virtual three dimensional model of an object viewable in at least some of the plurality of radiographic images In a more detailed embodiment of the second aspect, the motion sensor includes an inertial measurement unit. In yet another more detailed embodiment, the motion sensor includes a plurality of accelerometers. In a further detailed embodiment, the motion sensor includes a plurality of magnetometers. In still a further detailed embodiment, the motion sensor include a plurality of gyroscopes. In a more detailed embodiment, the system further includes a display communicatively coupled to the processor and operative to display the virtual three dimensional model. In a more detailed embodiment, the system further includes a radiographic image taking machine.

It is a third aspect of the present invention to provide a method of providing surgical navigation, the method comprising: (a) obtaining a plurality of radiographic images taken intraoperatively from multiple vantage angles that include a body part and at least one image target; (b) registering the body part intraoperatively to a navigation system; (c) calculating at least one of an orientation and a position of the body part in a three dimensional coordinate system used by the navigation system; and, (d) displaying a virtual model of a tangible item comprising at least one of the body part, a surgical instrument, and an orthopedic implant, where displaying the virtual model includes changing in real-time at least one of a position and an orientation of the virtual model to accord with a change in at least one of position and orientation of the tangible item.

In a more detailed embodiment of the third aspect, the virtual model of the tangible item comprises a three dimensional model associated with the navigation system, and the registering step includes registering a two dimensional image of the body part to the three dimensional model. In yet another more detailed embodiment, the registering step includes identifying two dimensional anatomical landmarks of the body part from the plurality of radiographic images and registering those two dimensional anatomical landmarks with three dimensional landmarks associated with a virtual three dimensional model of the navigation system. In a further detailed embodiment, registering the two dimensional anatomical landmarks with the three dimensional anatomical landmarks includes projecting the three dimensional landmarks onto a two dimensional image. In still a further detailed embodiment, projecting the three dimensional landmarks includes adjusting a pose of the three dimensional model so that a distance between selected two dimensional landmarks is reduced with respect to a distance between corresponding three dimensional landmarks. In a more detailed embodiment, the registering step includes using a patient specific instrument that correctly engages the body part in only a single position and orientation. In a more detailed embodiment, the patient specific instrument includes an inertial measurement unit. In another more detailed embodiment, the patient specific instrument includes a plurality of accelerometers. In yet another more detailed embodiment, the patient specific instrument includes a plurality of gyroscopes. In still another more detailed embodiment, the patient specific instrument includes a plurality of magnetometers.

In yet another more detailed embodiment of the third aspect, the method further includes obtaining a plurality of radiographic images taken preoperatively from multiple vantage angles that include the body part, and creating a virtual three dimensional model of the body part from the plurality of radiographic images. In yet another more detailed embodiment, the method further includes calibrating the plurality of radiographic images taken preoperatively prior to creating the virtual three dimensional model. In a further detailed embodiment, the method further includes planning a surgical procedure using the virtual three dimensional model. In still a further detailed embodiment, the method further includes gathering motion data from the body part repositioned within a range of motion, the body part having mounted thereto a motion sensor. In a more detailed embodiment, the motion sensor comprises an inertial measurement unit. In a more detailed embodiment, the inertial measurement unit comprises a plurality of accelerometers, a plurality of gyroscopes, and a plurality of magnetometers. In another more detailed embodiment, the motion sensor is mounted non-rigidly to the body part. In yet another more detailed embodiment, the motion sensor is mounted outside an epidermis at least partially covering the body part. In still another more detailed embodiment, the motion sensor is mounted rigidly to the body part.

In a more detailed embodiment of the third aspect, the plurality of radiographic images comprise a plurality of X-ray images. In yet another more detailed embodiment, the plurality of radiographic images comprise a plurality of fluoroscopic images. In a further detailed embodiment, the method further includes calibrating the plurality of radiographic images obtained intraoperatively. In still a further detailed embodiment, the calibration of the plurality of radiographic images is performed automatically by a computer running a software program. In a more detailed embodiment, the method further includes gathering data from the motion sensor that may be used to determine at least one of position and rotation of the motion sensor as a function to time. In a more detailed embodiment, the data gathered from the motion sensor is gathered wirelessly. In another more detailed embodiment, the data gathered from the motion sensor is gathered from a wire connected to the motion sensor.

In yet another more detailed embodiment of the third aspect, the data gathered from the motion sensor is gathered by at least one of a phone, a computer, a tablet, and a portable memory. In yet another more detailed embodiment, the method further includes registering in three dimensional space the motion sensor to a virtual three dimensional model of the body part, and correlating gathered data from the motion sensor as a function of position of the body part to create a virtual dynamic model of the body part that is repositionable to reflect actual positions of the body part when repositioned within a range of motion. In a further detailed embodiment, the method further includes constructing a virtual three dimensional model of the motion sensor using the plurality of radiographic images. In still a further detailed embodiment, the method further includes constructing a virtual three dimensional model of the motion sensor using the plurality of radiographic images. In a more detailed embodiment, the virtual three dimensional model of the motion sensor is integrated into the virtual three dimensional model of the body part to create a virtual three dimensional combined model. In a more detailed embodiment, the method further includes correlating gathered data from the motion sensor as a function of position of the body part to provide dynamic movement to the virtual three dimensional combined model. In another more detailed embodiment, gathering the motion data includes recording at least one of changes in position and rotation of the motion sensor as a function of time. In yet another more detailed embodiment, gathering the motion data includes recording changes acceleration of the motion sensor as a function of time. In still another more detailed embodiment, the motion data gathered is time stamped.

BRIEF DESCRIPTION OF THE DRAWINGS

FIG. 7 is an exemplary depiction of feature detection on pelvis X-ray images taken in different views in accordance with the instant disclosure.

FIG. 8 is an exemplary depiction showing feature matching between multiple 2D images, taken in different views, only using the grid-based motion statistics approach on pelvis X-ray images in accordance with the instant disclosure.

FIG. 12 is an exemplary depiction of multiple X-rays of the pelvis taken from the perspective of the right Judet view, the AP view, and the left Judet view.

FIG. 13 is an exemplary depiction showing X-ray images with bone and attached sensor.

FIG. 18 is an exemplary depiction showing the relationship between input-space distance and feature-space distances as part of the instant disclosure.

FIG. 19 is an exemplary depiction of screen shots showing automatic calculation of anatomical landmarks on pelvis and femur 3D virtual models.

FIG. 20 is an exemplary depiction of screen shots showing planned placement of a acetabular cup and a femoral stem on pelvis and femur 3D virtual models.

FIG. 21 is a screen shot depicting generic templating of an acetabular cup with respect to a pelvis 3D virtual model.

FIG. 50 is an exemplary radiographic image showing an RPO Judet view of an exemplary embodiment in accordance with the instant disclosure showing placement of the image target with respect to the patient anatomy (pelvis).

FIG. 51A is an exemplary radiographic image showing an AP view of an exemplary embodiment in accordance with the instant disclosure showing placement of the image target with respect to the patient anatomy (pelvis).

FIG. 51B is an exemplary radiographic image showing an LPO Judet view of an exemplary embodiment in accordance with the instant disclosure showing placement of the image target with respect to the patient anatomy (pelvis).

FIG. 64 is a diagram depicting the relationship between input-space distance and feature-space distances.

FIG. 75 is a ligament loci probability map for a distal femur and a proximal tibia.

DETAILED DESCRIPTION

The exemplary embodiments of the present disclosure are described and illustrated below to encompass exemplary surgical navigation methods and corresponding devices and systems. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1A:
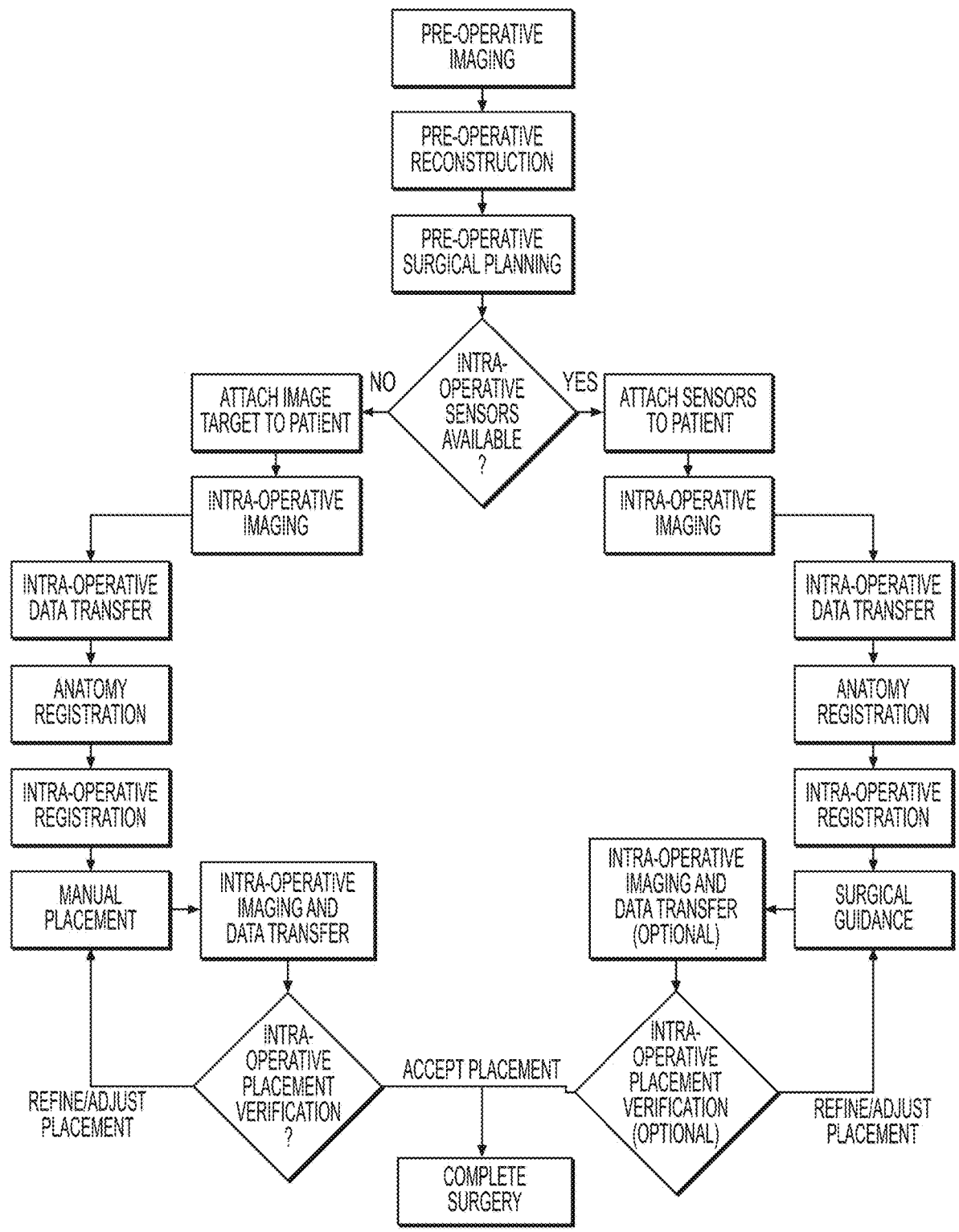
FIG. 1A is an exemplary system overview of an exemplary surgical navigation of the hip using pre-operative X-ray or fluoroscopy in accordance with the instant disclosure.
Figure 1B:
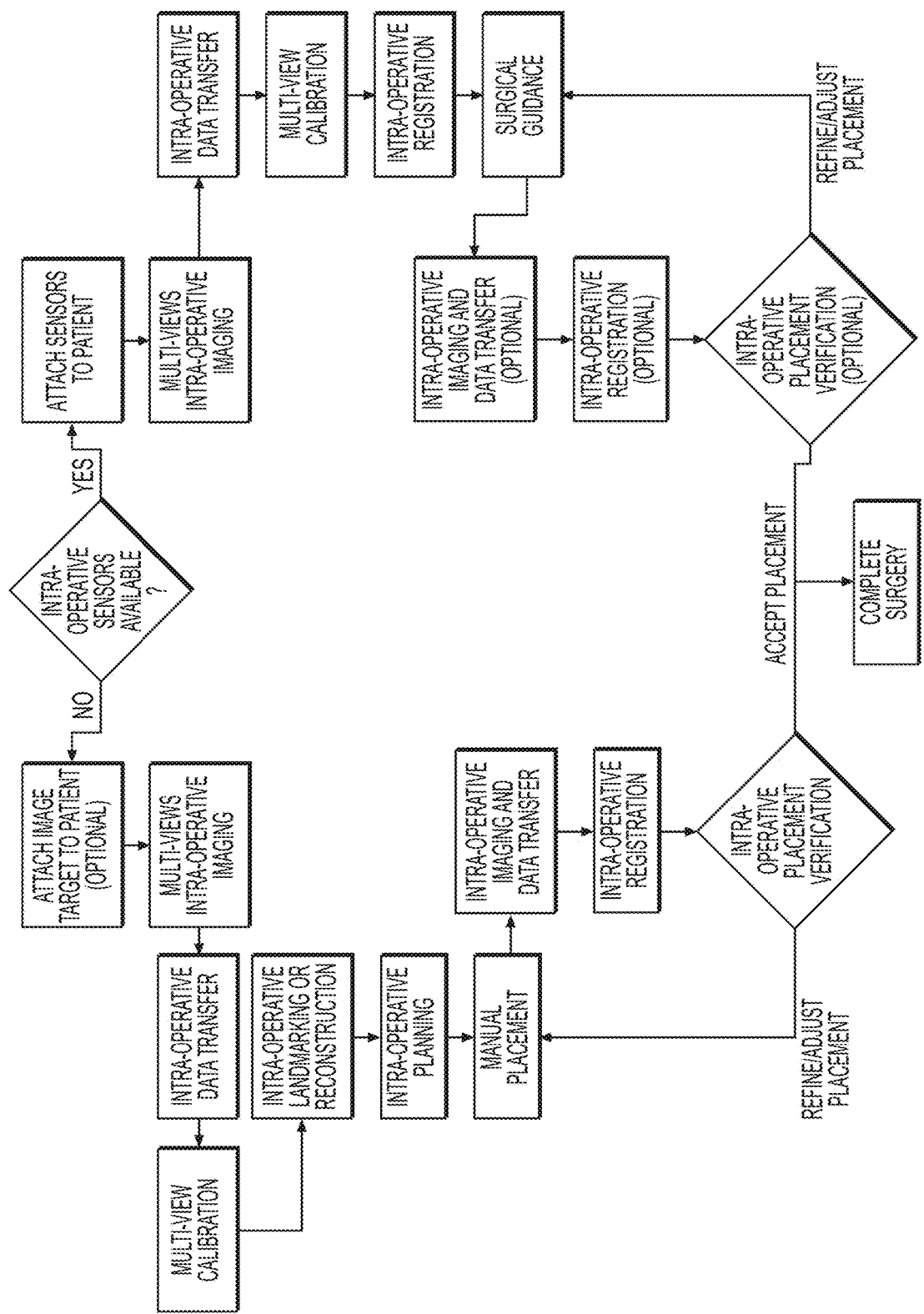
FIG. 1B is an exemplary system overview of an exemplary surgical navigation of the hip using intra-operative X-ray or fluoroscopy in accordance with the instant disclosure.

An exemplary system, as described herein, comprises a hybrid system combining intraoperative fluoroscopy and/or X-ray and tracked instrumentation for real-time navigation. See FIG. 1. The system may utilize one of several variations as outlined in detail hereafter. For each of the configurations below, intraoperative fluoroscopy may be replaced by digital planar radiography.

Figure 2:
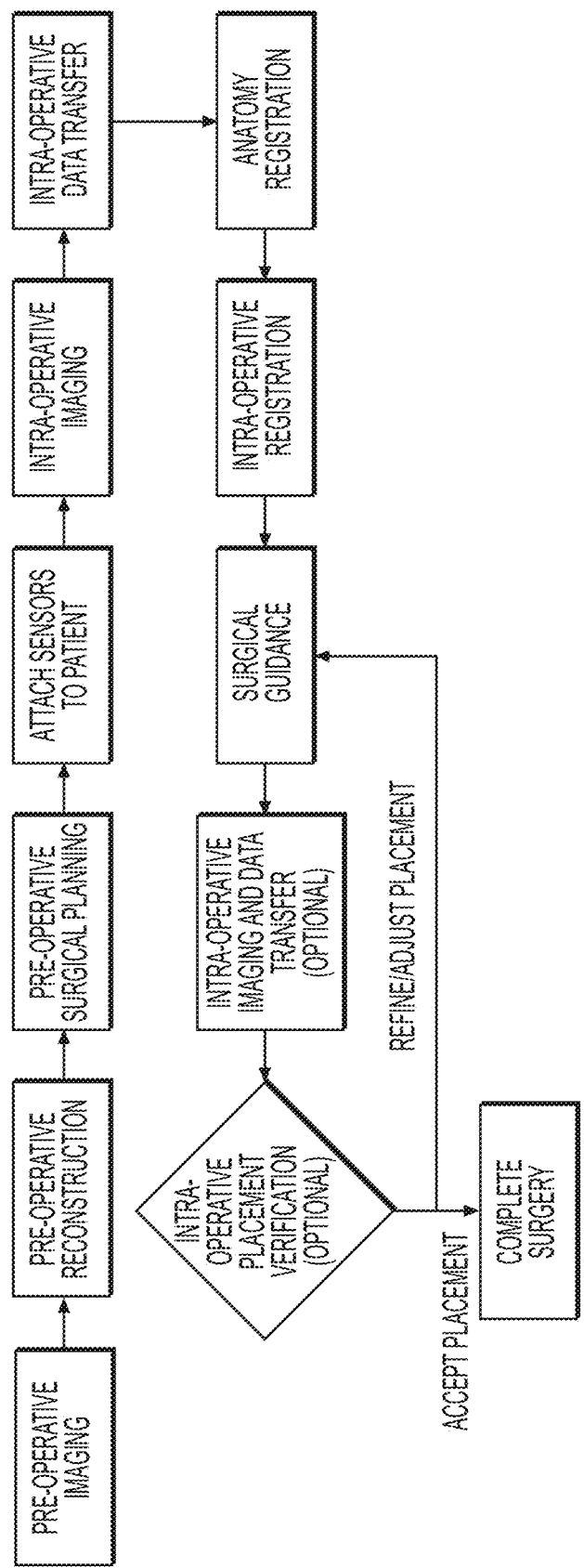
FIG. 2 is an exemplary system overview of image-based preoperative planning with intraoperative real-time image-based navigation system using tracking sensors in accordance with the instant disclosure.

FIG. 2 outlines an exemplary workflow of an exemplary navigation configuration utilizing a real-time tracking system and 2D imaging. The navigation system configuration outlined may require pre-operative imaging for 3D surface creation of pelvis and/or femur from one or more radiographic images, which is performed in the Pre-operative Reconstruction module. Associated with the 3D models are anatomical landmarks, defining anatomical sizing and reference coordinate system(s). The 3D anatomical models may then be input into a pre-operative surgical planning module, where the acetabular and/or femoral replacement components are virtually positioned. Intraoperatively, a first reference IMU/position sensor assembly (sensor, image target and reference piece), including radio opaque features distributed in a known orientation is attached to a patient pelvis or femur being navigated; a second IMU/position sensor is attached to the tool being tracked. A single 2D X-ray or fluoroscopic image may be acquired and adjusted to correct for any image distortion. Each intraoperative image contains at minimum the anatomy being navigated as well as a portion of the reference sensor assembly. Images are transmitted to a computer/tablet wirelessly or via some other suitable data transfer method. The navigation software module running on the computer uses inputs such as image(s), 3D anatomical model(s) and related information such as the surgical plan, implant templates, anatomical landmarks or any other data relevant to the procedure. The software may then perform a first 3D to 2D registration to align the 3D anatomy with the image. One way to accomplish this is first initializing the 3D to 2D registration process via landmark-based registration, where 3D anatomical landmarks on the 3D anatomy are registered to corresponding 2D landmarks on the image by adjusting the pose of the 3D bone so that the distance between the selected 2D landmarks on the image and the location of the 3D landmarks after projection onto the 2D image is minimized. A second registration step may be performed, where information from the image (detected edges, contours, regions, gradient, and/or texture information) is used to further adjust the 3D position and orientation of the 3D model so that a projection of the model onto the image plane is optimized based on a minimum error or maximum correlation between projection and image information. In one exemplary embodiment, the image information may be calculated by first detecting edges in the image, then performing a distance transformation on the edge map image. A cost function, used in the optimization step, may then calculate, by creating an off-screen projection of the 3D model at the current position and orientation (a "pose"), edge and gradient information from this image. A scoring function may then calculate as the sum of the pixel-wise product of the two images plus the sum of the absolute value of pixel-wise dot products between the two gradient directions (gradient directions of the acquired image and gradient directions of the projected image). The first reference sensor assembly may be registered to patient anatomy through registration of the radio-opaque features of the assembly with the 2D image. This registration allows merging of the patient preoperative coordinate frame with intraoperative imaging coordinate frame, and the tracking sensor coordinate frame. Upon completion of certain steps, real-time intraoperative guidance may be achieved by tracking instrumentation in reference to patient anatomy to achieve the desired surgical target. Additional X-ray or fluoroscopic image(s) may be taken upon placement of the trials and/or final implants to measure final implant placement, leg offset and leg length via yet another registration step of anatomy to images and components to images. In addition, a distance measuring device may be used to capture distance between reference and instrument sensors, which then may be utilized to capture relative translation between both sensors.

Figure 3:
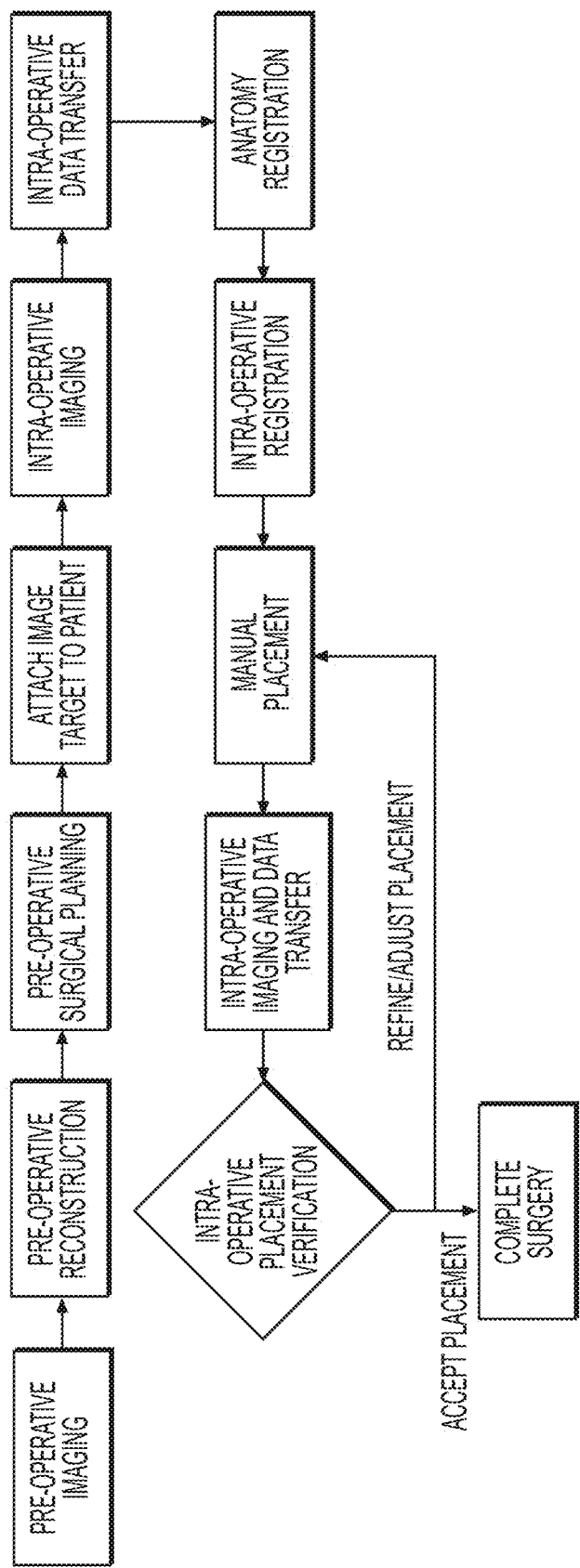
FIG. 3 is an exemplary sensor-less variation of the image-based preoperative planning plus intraoperative real-time image-based navigation system in accordance with the instant disclosure.

FIG. 3 describes an exemplary variation of the previous configuration where sensors may be replaced by static X-ray or fluoroscopic imaging containing the anatomy and implant. The position and orientation of the implant is registered to the image by another 3D to 2D registration process though initialization can be made by aligning the 3D implant in a default or planned position and orientation relative to the already registered 3D anatomical model(s). Presumably this initialization is close to the final position and therefore comprises a sufficient initial guess. Once an implant (or trial) component is registered, the orientation and position of the component may be calculated in the 3D coordinate system and reported to the operator on the screen. Adjustments may be made to the virtual 3D implant and projected onto the 2D image to provide feedback related to expected image content if placed properly. The software may also suggest alternate sizing and positioning to allow the configuration that results in minimal offset and leg length discrepancy. If both femoral and acetabular implants have been placed and 3D models have been registered to an image containing both components, final component orientation and positioning can be computed.

Figure 4:
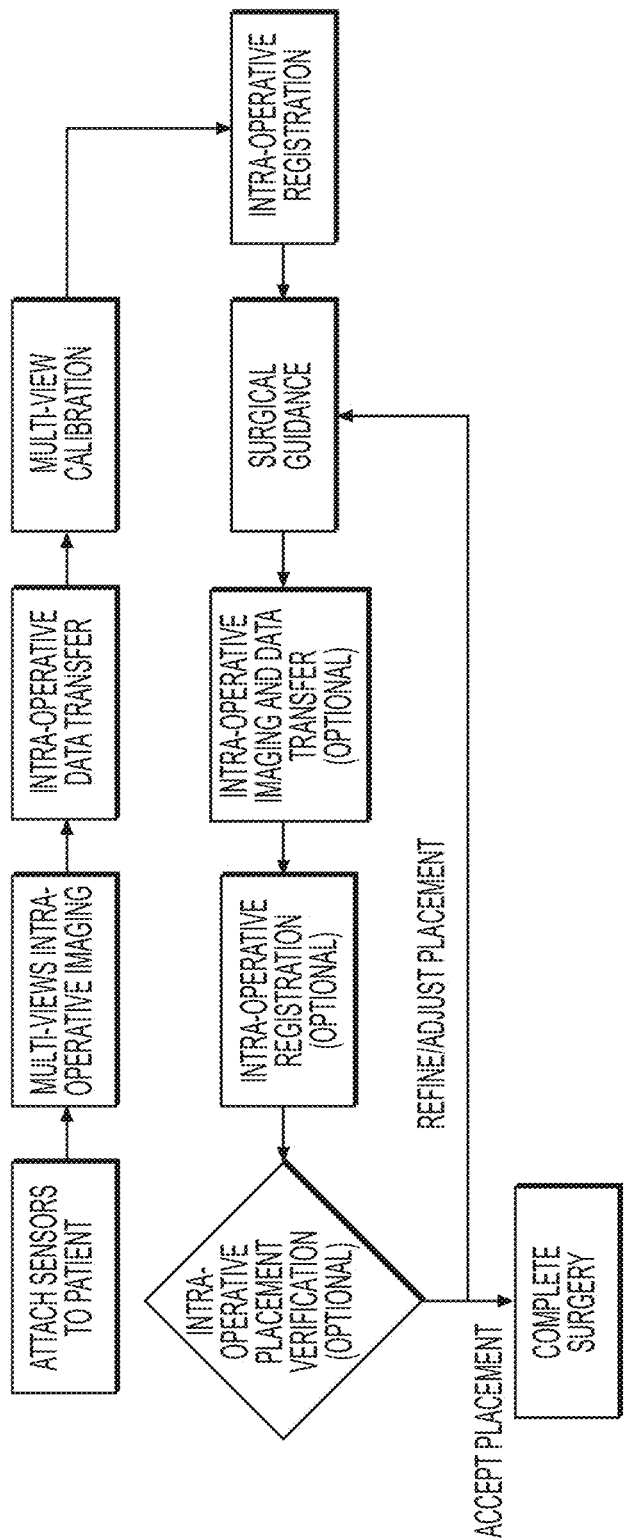
FIG. 4 is an exemplary system overview of image-based intra-operating planning with intraoperative real-time image-based navigation system using tracking sensors in accordance with the instant disclosure.

In yet another exemplary configuration of the overall system, image-based real-time intraoperative navigation system is utilized without preoperative imaging or planning. FIG. 4 outlines the workflow of this exemplary configuration. Intraoperatively, a reference IMU sensor assembly with radio opaque features distributed in a known configuration is attached to the patient pelvis or femur being navigated. An additional IMU sensor is attached to the tool being tracked. One or more x-ray/fluoroscopy images of the pelvis and femoral anatomy are acquired. Each image should contain one of the anatomies being navigated as well as at least a sufficient part of the reference sensor assembly for registration. For example AP, judet RPO and/or judet LPO may be adequate images. Images can be transmitted to a computer wirelessly or via any storage media, such as USB or any other suitable data transfer method. The navigation software module uses the images and processes them to calculate a calibration between each of the images by extracting the relative orientation and position of the rigidly fixed reference assembly containing radio opaque features in each the acquired shots via 3D to 2D registration of the assembly to each of the images. On each image, one or more anatomical landmarks may be identified through an automated or semi-automated process. From the set of calibrated images and the located landmarks, multi-view camera geometry principles may be used for creation of 3D coordinates for each of the landmarks identified in 2 or more of the images. For example, for the pelvis landmarks may include the right and left Anterior-Superior Illiac Spine, right and left Pubic Tubercle Points and for the femur, the femoral head center and center of the femoral IM canal are calculated. The landmarks are then utilized to calculate the 3D surgical coordinate system(s) used for planning the procedure. For example, the anterior pelvic plane for the pelvis and the anatomical axis and femoral neck axis for the femur. Those surgical axes are then utilized for measurement of implant placement and the sizing of the acetabular cup and femoral stem. The orientation of the reference sensor is registered to generated landmarks and surgical axes via its known position and orientation relative to the reference assembly's fiducial markers. Upon completion of this step, real-time intraoperative guidance can be achieved by tracking instrumentation relative to the patient anatomy to enable placement of the components according to a defined surgical target. Tracking of instruments is performed by a second IMU that is attached to each instrument as it is being used in the surgical procedure. Additional, though optional, fluoroscopy images can be captured upon placement of the trials and final implants to measure final implant placement, leg offset and leg length. In addition, a distance measuring device can be used to capture distance between reference and instrument sensors, which then may be utilized to capture relative translation between both sensors.

Figure 5:
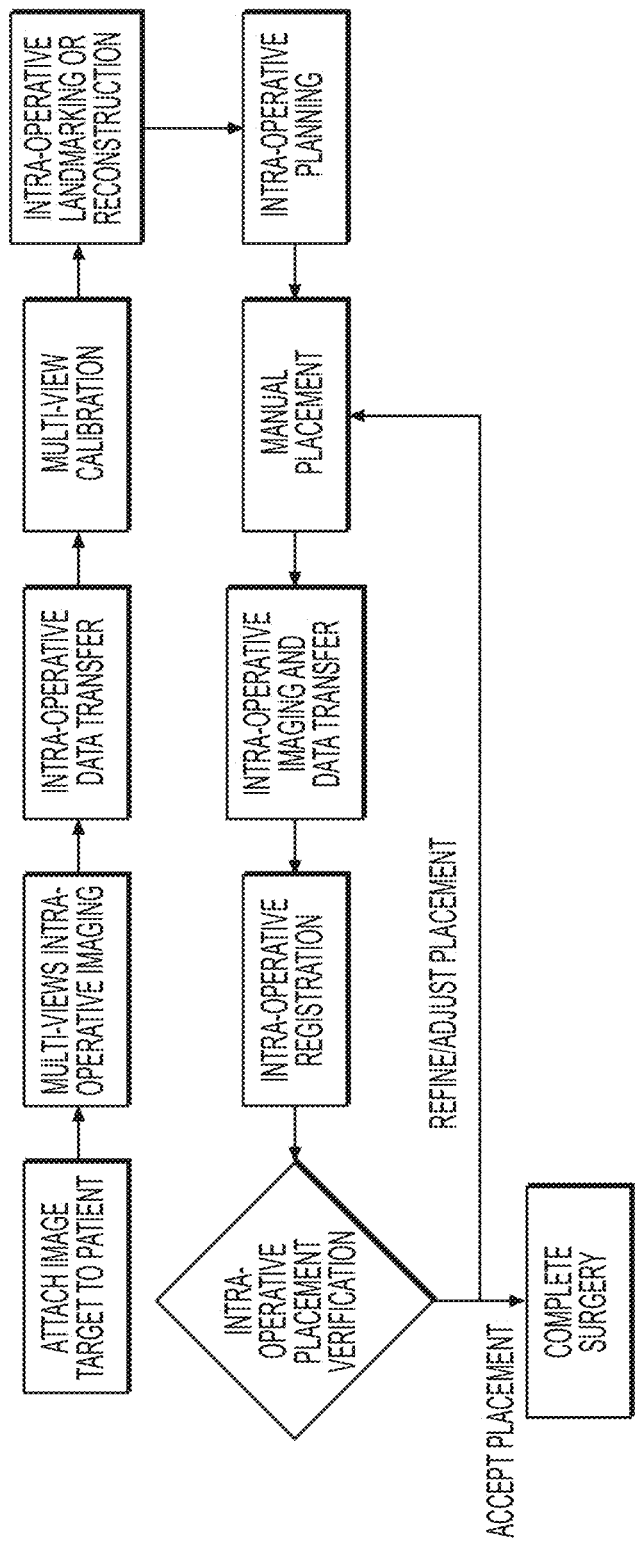
FIG. 5 is an exemplary configuration for navigation using X-ray images and no real-time tracking system, without reconstruction, in accordance with the instant disclosure.

In the following exemplary configuration, the real-time tracking system with sensors may be omitted, as may be pre-operative imaging. In this configuration, intraoperative imaging is utilized to obtain feedback related to component position and orientation. The registration of bone, image target and component to each of the captured images and reconstruction of bone anatomy and/or landmarks from images is performed using the methods disclosed here for all configurations. FIG. 5 describes the steps in this exemplary configuration. The position and orientation of the implant is registered to the image by the registration process as described in detail hereafter. Automatic initialization of the implant registration may be made by aligning the 3D implant in a default position and orientation relative to the already registered 3D landmark(s). Once an implant (or trial) component is registered to the acquired images and patient anatomy and/or landmarks, the orientation and position of the component may be calculated in the 3D coordinate system and reported to the operator on the screen. Adjustments may be made to the virtual 3D implant and projected onto the 2D image to provide feedback related to expected image content if placed properly. The navigation software module may also suggest alternate sizing and positioning to allow the configuration that results in minimal offset and leg length discrepancy. If both femoral and acetabular implants have been placed and 3D models have been registered to an image containing both components, final component orientation and positioning can be computed.

I. Pre-Operative Imaging

An exemplary step of the exemplary configurations may include performing imaging of the patient joint and creation of 3D models for virtual surgical planning. Aside from the traditional imaging methodologies utilizing static imaging modalities, such as X-ray, CT and/or MRI to create patient anatomical models, this exemplary disclosure may incorporate additional techniques to create patient bone as well as joint motion. In one exemplary embodiment, one or more X-ray images may be used to create a 3D patient-specific anatomical model for landmarking and measurements. At the same time, one or more tracking sensors may be fixed to the patient and used in conjunction with the captured images to obtain joint motion data. This is outlined in more detail hereafter. In another exemplary embodiment, if no sensors are available, X-ray or fluoroscopy may be used to image patient anatomy during multiple activities. The recorded images of activities may be utilized to build 3D patient models coupled with kinematic data, which may then be used for landmarking and dynamic and/or static surgical planning. In another exemplary embodiment, ultrasound may be used to create the patient's bone model for landmarking and measurements.

Figure 6:
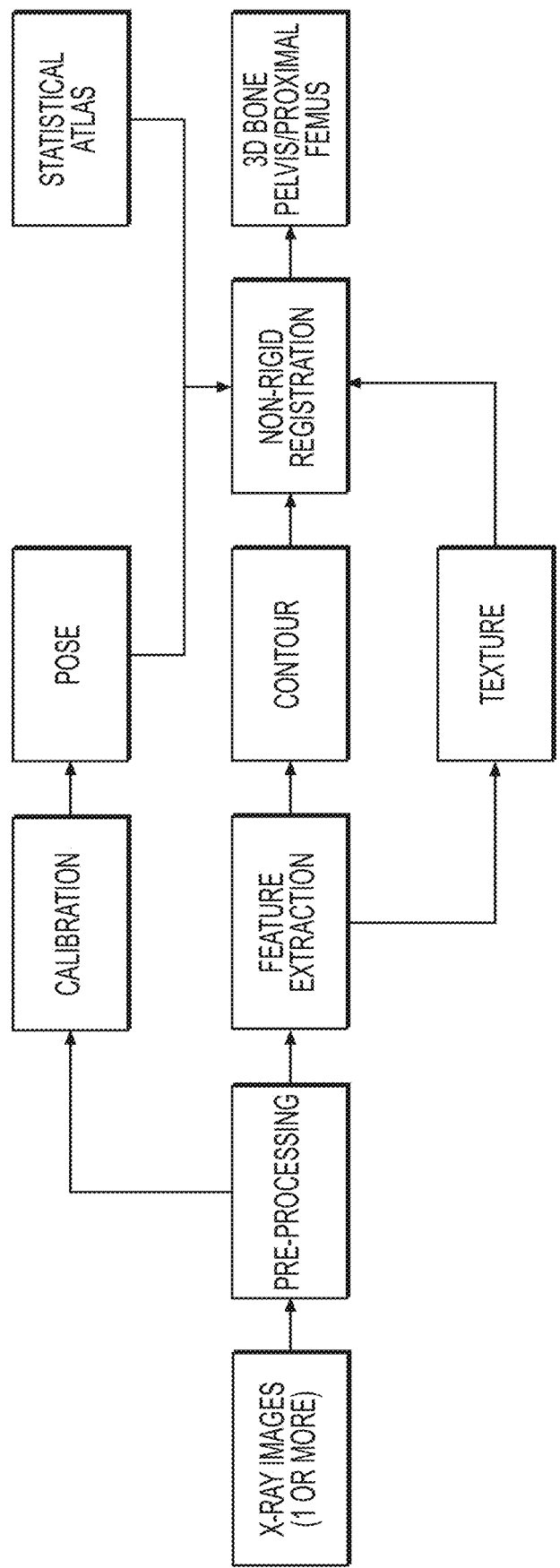
FIG. 6 is an exemplary process flow depicting a non-rigid registration for creation of patient specific three-dimensional pelvis and proximal femur models from X-ray in accordance with the instant disclosure.

A. X-Ray Reconstruction of a Joint 3D reconstruction, or non-rigid registration (shown in FIG. 6), of anatomical models from multiple X-ray images plays an important role in understanding the patient joint. However, a central problem in existing 3D reconstruction methods from multi-view X-ray images lies in the following constraint: X-ray images are taken with different types of markers or braces as calibration targets in order to improve the accuracy of calibration with regard to estimating the relative position and orientation of image pairs. However, the major limitation of such a calibration approach is that it is only capable of handling the stereo radiographic images including specific calibration targets. To potentially address the above issues, a practical method without the need for a calibration target is disclosed for estimating epipolar lines based on feature correspondences from X-ray images of the same object or objects in different views.

Epipolar geometry between two images is the intrinsic projection geometry most often determined by finding corresponding pixels in one image, given a set of pixels in the other image. It can be determined by computing the fundamental matrix describing the projective transformation between corresponding pixels in image pairs. To estimate epipolar lines between image pairs, employed are feature correspondences that involve finding the projections of the same scene points in both images acquired in different views. However, matching the corresponding pixels or features in biplanar X-Ray images is an especially challenging problem because the corresponding information may appear in different regions and shapes of each image. To this end, hybrid feature correspondences across multi-view X-ray images may be established.

An exemplary embodiment of the feature correspondence may be composed of: (1) feature detection, (2) feature description, and (3) feature matching. A set of discriminative features on X-ray inputs may be denoted as points, edges, lines, patches, or on any mixture thereof. In one example embodiment, feature points may be used to find a sparse set of corresponding locations in different images as a prerequisite for computing the projective transformation between a pair of two input images. Feature points for pixel-wise detection may be considered with large contrast changes and gradients in significantly different orientations where the pixel-wise detection performs pixels in one location of the input image at a time. To find a set of corresponding point features in both images, each of the feature points associated with a position (x, y) in the 2D image domain may be described as a feature vector representing a local appearance and spatial relationship around the position of the feature point in the input image. The feature vectors are referred to as feature descriptions. To estimate the fundamental matrix between image pairs, a set of feature points in the reference are matched to another set of feature points in the target along with identifying true and false matches during the comparison of feature vectors.

In biplanar X-ray images, feature detection may be used as the primary process of determining feature correspondences to extract salient features represented in the image such as points, edges, lines, patches, on any mixture thereof. The textures in the image, which are directly related to the local salient information of the features, are critical to efficiently perform the feature correspondences. However, feature correspondences on minimally textured bone structures in X-ray images may suffer from degrading repeatability and stability of their performances on untextured regions due to the scarcity of the local salient information. In detecting corner points in target images to possibly address the challenging problems in untextured objects, corner detection approaches may provide the ability to detect a set of highly discriminative feature points on X-ray images with untextured bone structures. In consideration of scale invariance, the corner point detection over multiple scales of the image may be employed. An exemplary method of feature detection, referencing FIG. 7, may include performance of some or all the following steps: (1) Extracting corner points via existing corner detection approaches; (2) Filtering the detected corner points on edges by measuring cornerness of each point; and (3) Repeating previous steps (1) and (2) at each level of a scale pyramid of the image. Once salient corner points are detected among all the pixels in the image, the local information of each the detected corner points around their locations ma by encoded to a vector where the local information may be characterized as salient visual patterns, orientation, or on any mixture thereof. To match the corresponding corner points in image pairs, the method may include performing a hybrid feature correspondence using the grid-based motion statistics and the vector field consensus approaches where the vector field consensus approach is employed to remove the outliers in the matching results from the grid-based motion statistics approach. FIG. 8 shows the result of feature matching via the grid-based motion statistics approach. There remain a large number of false correspondences or outliers especially in the highlighted region of FIG. 8. By removing false matches, the comparable results can be obtained.

Figure 9:
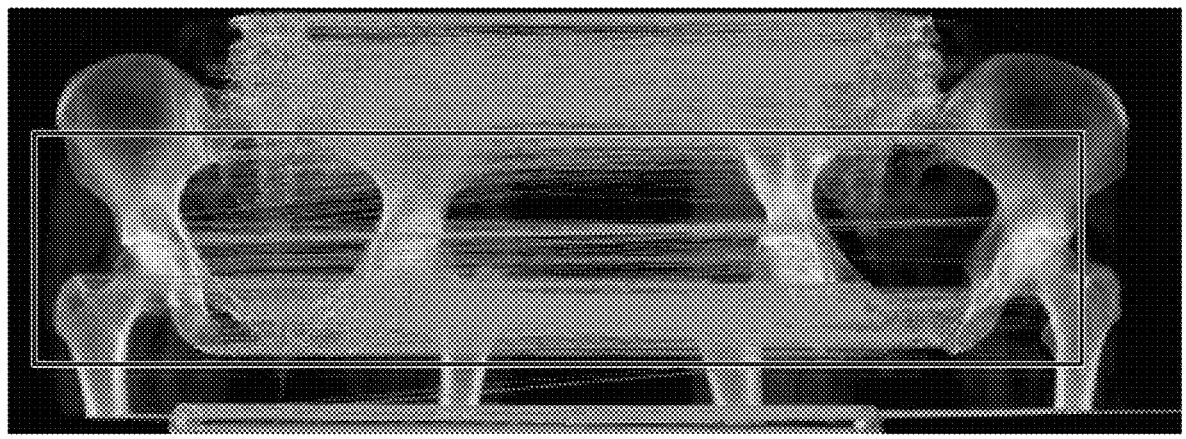
FIG. 9 is an exemplary depiction showing feature matching between multiple 2D images, taken in different views, using the combination of the grid-based motion statistics and the vector field consensus approaches on pelvis X-ray images in accordance with the instant disclosure.

As shown in FIG. 9, the hybrid feature correspondence method can provide the ability to improve the accuracy of estimating epipolar lines in the image pairs. For this reason, the exemplary method of feature matching may employ the outlier removal method to conduct better epipolar line estimation. More specifically, the hybrid feature correspondence method reduces the population of outliers as compared to the results of the grid-based motion statistic approach as shown in FIG. 8. This hybrid correspondence method may provide the ability to improve the accuracy of estimating epipolar lines in the image pairs.

The true matches or inliers obtained from the hybrid correspondence described herein may be used to compute the fundamental matrix that may be estimated using a random sample consensus (RANSAC) scheme in which iterative random selections of 8 matches are established. In each selection of the RANSAC scheme, the fundamental matrix is estimated, and its accuracy is assessed by considering the cardinality of the subset of the candidate matches. Once the best correct solution of the fundamental matrix is found, epipolar lines (considering the knowledge of the internal camera parameters) can be determined using the basic properties of the fundamental matrix regarding if any pair of points x and x^' in the two images correspond, then x' lies on the epipolar line l^'=Fx corresponding to the point x where F denotes the fundamental matrix. These epipolar lines may be employed to reconstruct 3D models of the bone structure by using the geometrical relationship between the world points and their projections on the image planes as described below.

Figure 10:
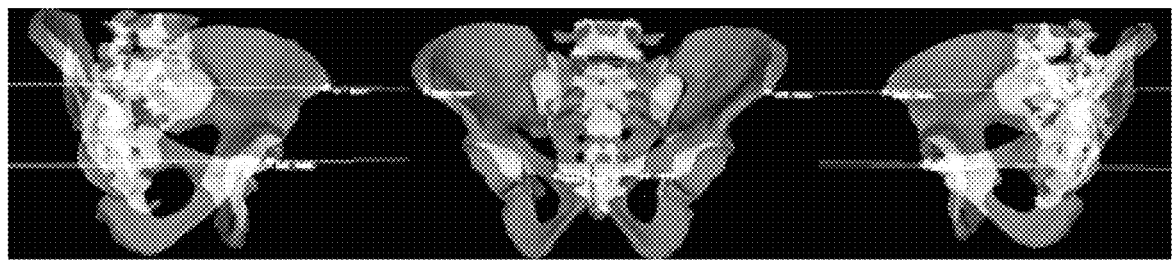
FIG. 10 is an exemplary depiction of DRR images of Right Judet view, the AP view, and the Left Judet view of an exemplary pelvis model in accordance with the instant disclosure.
Figure 11:
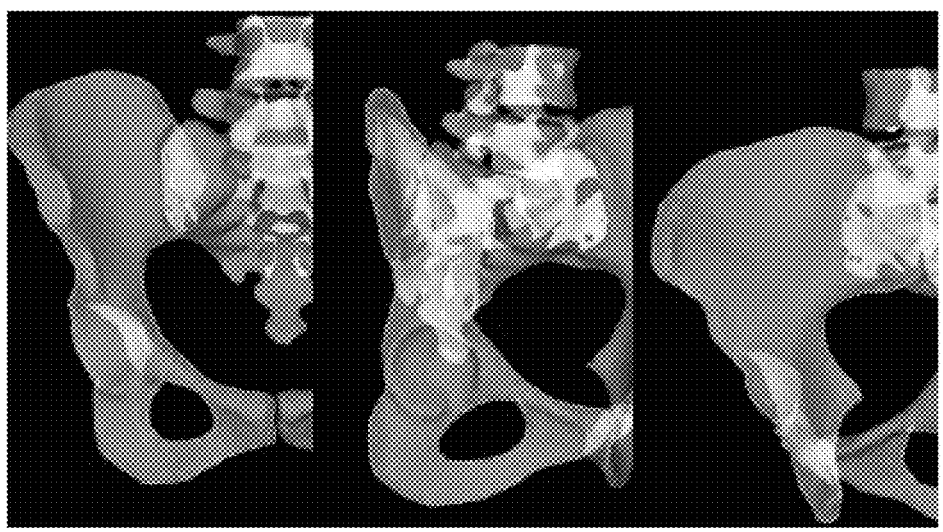
FIG. 11 is an exemplary X-ray reconstruction, in accordance with the instant disclosure, showing highlighted bone boundaries for morphing.

An alternative exemplary method of calculating feature points and correspondences between X-ray views may utilize a priori information relating to the anatomy being imaged and the expected image properties of the anatomy. This alternate exemplary method uses statistical shape models, having point correspondence across all anatomical samples that are incorporated in the model. For each shape model having a corresponding CT image, digitally reconstructed radiographs (DRRs) may be simulated at a plurality of known views. Each DRR is a simulated X-ray image of the patient anatomy with known camera parameters. For each DRR, the position of the patient anatomy, with point correspondence to a statistical shape model, relative to the image plane is also known. For each view, feature descriptions for each vertex on the anatomical model may be calculated by determining the location of the vertex on the DRR image and calculating the desired feature information at the image coordinate of the projection. The image coordinate of the projection is determined by tracing a line from the camera origin, through the shape vertex and onto the image plane. Now, for each DRR image, this process generates the feature descriptions on the image for each vertex on the anatomical model. Thus, for each dataset (CT+ anatomical model), multiple DRR's are generated simulating the expected images to be acquired during in-office reconstruction (see FIG. 10). Now, for each pose—AP, Right Judet, Left Judet for example—statistics may be calculated for the distribution of the feature descriptors at each vertex on the anatomy. These statistics may be used as a priori information in the process of determining point correspondence in real-world images. It should be noted that feature descriptors and methods of calculating them are known to those skilled in the art of computer vision and that one or more suitable descriptors may be deployed in this process. To use this data, when new X-Ray images are acquired, their capture position is noted (AP, right Judet, left Judet, or similar) and the appropriate feature statistics may be loaded from the a priori data. Features in the new image are calculated from the image data and compared to the a priori dataset. In this step, each detected feature point is assigned a pairwise likelihood of belonging to the anatomical surface based on calculation of the a priori probability for each surface point given the feature points descriptor as calculated from the image. For each image, feature points are assigned to the surface vertex with the highest likelihood of membership given the feature descriptor. Fuzzy methods or similar statistical memberships may be employed. Correspondence may now be found between image points by matching feature points belonging to the same surface vertex. Alternative methods of correspondence calculation are easily seen, such as predicting the feature points in one image, given the feature points in another image by using known differences as determined in the a priori data. Another alternative is to utilize the a priori data in a machine learning framework to train a neural network to identify matching feature points across multiple X-ray images. Erroneous correspondences may now be filtered using RANSAC or similar robust methods familiar to those skilled in camera geometry.

After image calibration is performed, the reconstruction process estimates the 3D pose of the patient's bone within the different image views. This may be done by selecting automatically—using the same or similar a priori data as described previously—a predefined set of 2D points representing projections of 3D anatomical landmarks on the image dataset. Various anatomical landmark projection points are identified on at least two images from the image dataset. Corresponding points on the two images may then be used to calculate 3D landmarks in three-dimensions using the previously calculated fundamental matrix between the two images. A list of bone models from a statistical bone atlas may then be aligned to the calculated 3D landmarks, hence registering them in the patient space. Thereafter, a template bone model may be selected to initiate the reconstruction process. Given the extracted patient's bone poses in the different images, graphical 3D simulations of the radiological scenes used to capture the image dataset may then be created. The X-ray source may be represented by a perspective camera, simulating the radiological beam divergence, and may be placed at the image's focal length distance to the projection plane. Within the camera's field of view, the atlas bone models may be separately placed at the images' extracted 3D bone poses and bone projection images may be synthesized. The synthesized bone outlines may then be compared to the radiographic images'. The atlas bone model that produces synthesized bone outline distances closest to the radiological patient bone outlines may be selected as the initial reconstruction template.

The selected bone template may be morphed to better represent the patient anatomy. In the simulated radiological scenes, the radiological images may be placed on the projection planes, and rays may be generated between the x-ray source location and the radiological bone contour points. Template bone points may then be selected for every image ray based on the template points' distance threshold d and normal angle threshold (90−α) to the rays. Target 3D fitting points may be calculated by moving the selected points in a direction normal to the model's surface. The distance moved may be the distance between the ray and the ray's nearest template vertex. The template model may then be transformed so that the distances between the template's selected points and their corresponding 3D target points may be minimized. After that, the template may be morphed by optimizing the bone atlas' principle component values, to minimize the distance between the template's selected points and their corresponding 3D target points. Optimization may be done using any direct or heuristic search algorithm. This process may be repeated for a pre-determined number of iterations or when no more significant shape deformation occurs. The values of the distance d and angle at may start with larger values for gross deformation, then may linearly decrease for fine-tuning with every iteration.

Alternatively, a machine learning framework may be created using the DRR data described previously. In this framework, the expected principal components of the reconstructed bone may be predicted from the image data and initial pose. In this framework, an appropriately structured neural network may be trained using the DRR images and poses as input, and the principal components of the corresponding anatomical model. By generating a plurality of training sets and using these training sets to train a sufficiently deep neural network, the trained network may be used to predict the shape of initialized bone models in newly presented calibrated X-ray images (see FIG. 12).

B. Dynamic Imaging with Static X-Ray and Motion Sensors

Figure 14:
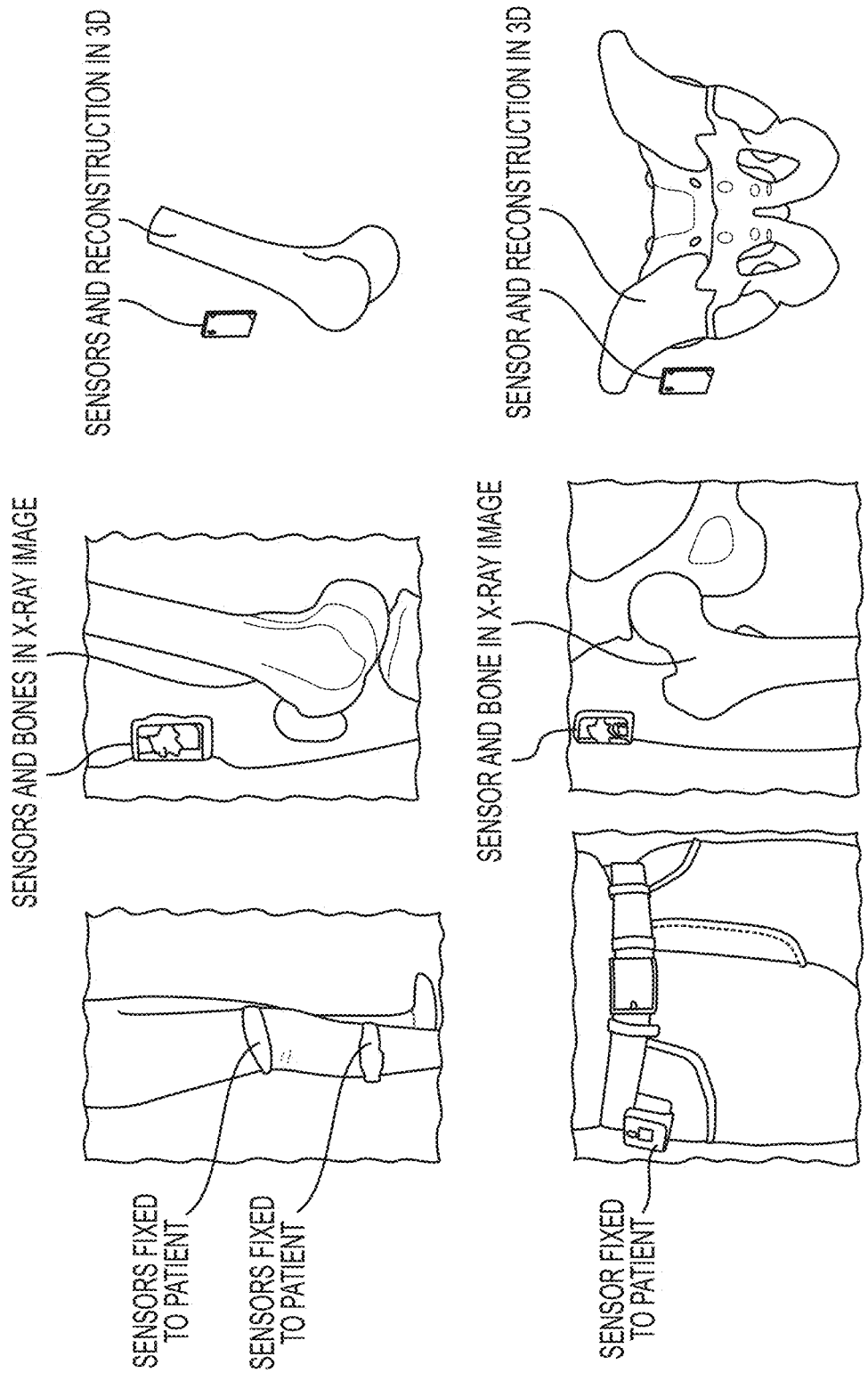
FIG. 14 is an exemplary depiction showing sensors attached to patient prior to imaging and the resultant X-ray images containing both a sensor and patient joint information.

In this exemplary embodiment, the patient may wear one or more motion sensing units, such as IMUs, comprising one or more accelerometers, gyroscopes and/or magnetometers, that outputs rotation and/or position of the sensor. The sensor may stream this data wirelessly to a processing device (phone, tables, PC, or similar). X-rays may then be captured, where each X-ray image contains at least one IMU sensor and a portion of the patient anatomy. These sensors may be fixed externally, using a wrap or flexible band or any other attachment means including, without limitation, adhesives. During imaging, the sensors and bones are captured and visible in multiple images. The calibration of the image sequence may then be performed by finding points on the imaged IMU sensor corresponding to known points on an IMU board design. The determination of corresponding points and regions may be performed automatically. These points in the image may correspond to components on the circuit board, such as resistors, capacitors, chips, routing or any other feature which may be distinctly identifiable in one or more X-ray images and on the circuit board, as shown in FIG. 13. Using the sensor for calibration, the bones may be reconstructed using the X-ray reconstruction methods outlined herein or any other method that may be familiar to those skilled in object reconstruction and non-rigid registration. The reconstructed bone surfaces, along with the registered sensors in the images, may be used to initialize a motion capture session, consisting of at least one bone and sensor, that have been registered in 3D space via X-ray reconstruction of the bone and registration of the sensor to the same image(s) used for reconstruction, thus providing information relating the sensor(s) to the bone(s). Using this relative information, the sensor data may now be related to the bone data directly. In this way, static X-ray images may be used to initialize a sensor-based motion capture system and used in capturing dynamic information of the 3D joint. This exemplary process is illustrated in FIG. 14. In this exemplary process, X-ray and sensor data may be used together to create dynamic imaging data. This data can be utilized in a similar way as fluoroscopy dynamic data as outlined herein. After the motion capture session is initialized, joint motion activities may be performed. During each activity, the orientation data from each sensor is relayed to the processing device and recorded. The processing device may provide some visual indication of the motion being performed, such as updated 3D renderings of the bone models in their respective positions determined using the sensor data. Here dynamic data encompasses at least a bone model, a sensor model, their relative positions and orientations, and time-stamped data relating to the motion of the bone during at least one activity (quaternions, rigid transformations, or any other as dictated by the sensor capabilities).

C. Fluoroscopy Reconstruction

Figure 15:
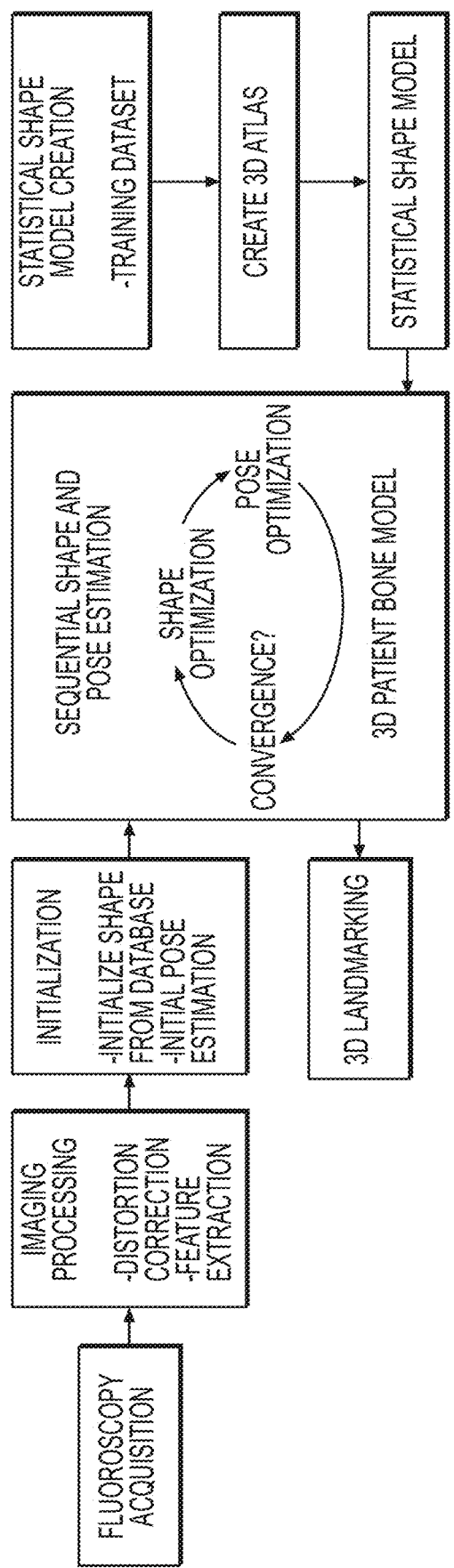
FIG. 15 is an exemplary process flow of a process for reconstruction of patient anatomy and surgical landmarking from fluoroscopy in accordance with the instant disclosure.

The overall structure of reconstruction may comprise one or more of four parts, as shown in FIG. 15: (A) Image processing, which extracts features from fluoroscopic images; (B) Initialization, which estimates the 3D model's initial pose using a hybrid classifier integrating k-nearest neighbors (KNN) and support vector machine (SVM) (may use other machine learning techniques to train and classify images); (c) Optimization, which determines the 3D model's optimal pose and shape by maximizing the similarity measure between the 2D X-ray fluoroscopy and the reconstructed 3D surface mesh model (the similarity measure is designed as a novel energy function including edge score, region score, homogeneity score, and multibody registration score); and, (D) 3D Shape Analysis, which represents the training dataset of 3D surface mesh models with nonlinear statistical shape model named kernel principal component analysis (KPCA).

Creation of anatomical information from dynamic fluoroscopic image data begins with fluoroscopic image acquisition. As part of this image acquisition, the subject/patient may be observed at any number of positions that may include a deep knee bend and opposing gait endpoints. Post image acquisition, an image processing substep may be carried out.

Using a calibration target, one can estimate distortion and remove it from subsequent images as part of the image processing substep. An exemplary step in this procedure may include estimating any 2D image's geometric distortion. By taking an X-ray of a known rectangular grid of metal beads, one can estimate a 2D spatial transform for each small square sub-image that is bounded by four beads. Using standard techniques in geometric distortion removal, a local bilinear model may be used to model the spatial mapping, as well as the gray level interpolation. Once the 2D distortion has been removed, the effective source-to-image plane distance (focal length) can be computed by a two-plane calibration grid with a known displacement between the planes.

Figure 16A:
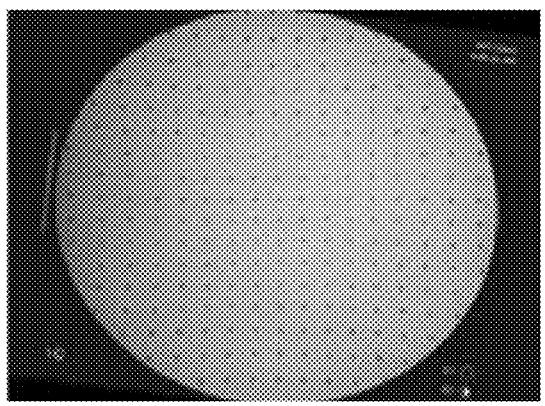
FIG. 16 is an exemplary depiction showing fluoroscopic images of geometric calibration grid, before distortion removal (left) and after distortion removal (right), in accordance with the instant disclosure.
Figure 16B:
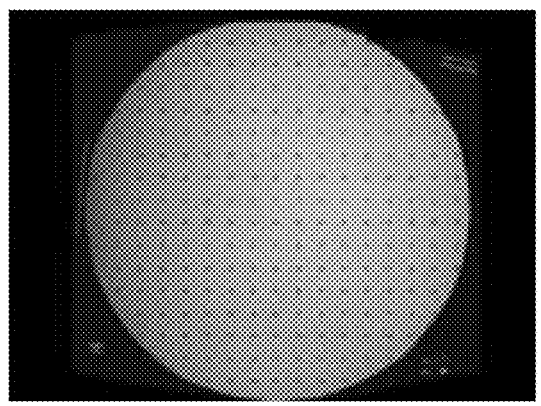

FIG. 16 illustrates a fluoroscopic image of a geometric calibration grid before and after geometric distortion removal. As part of this substep, one may compute the bilinear transform for each set of four grid points that transforms the image positions of the beads in the left image to regularly spaced grid locations in the right. Clearly, the calibration procedure removes the pin-cushion distortion so that the grid points lie along straight lines.

Figure 59:
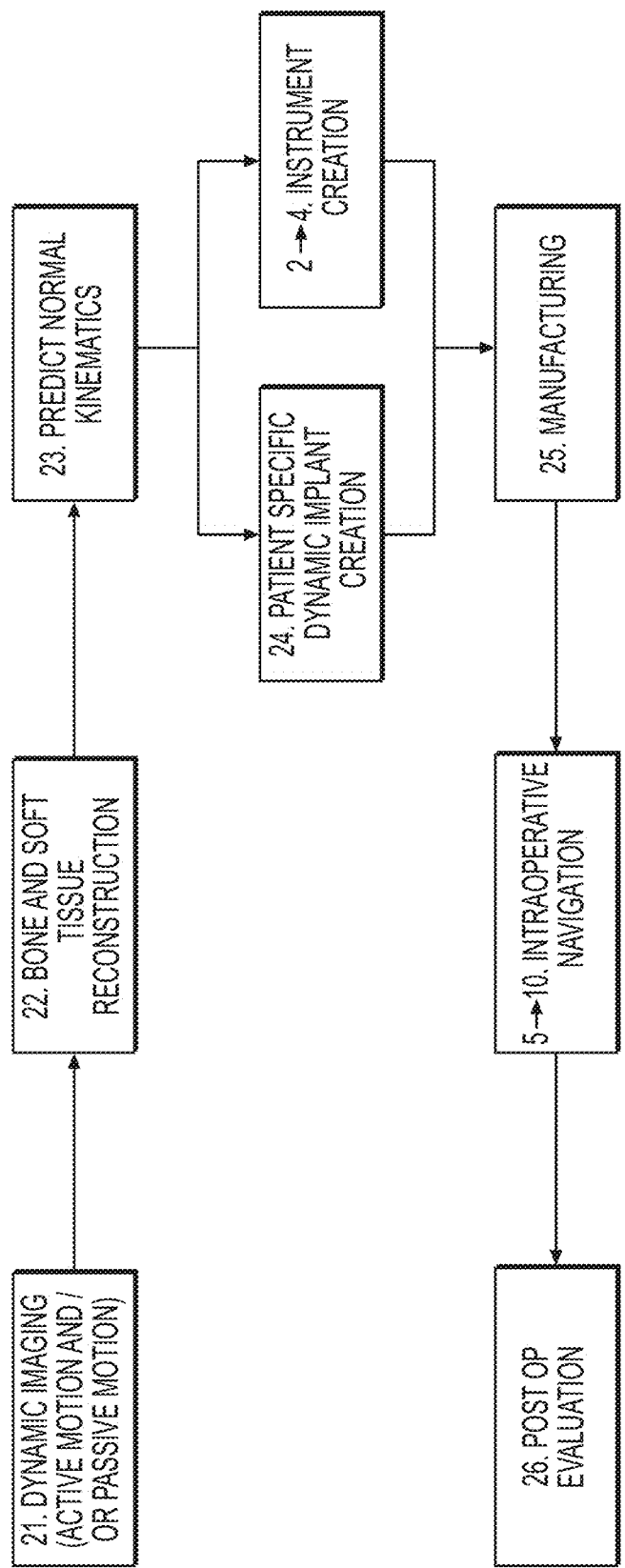
FIG. 59 is a flow diagram of an exemplary process of utilizing dynamic data across the episode of surgical care to create patient-specific implants and instruments, place the implant and monitor performance post-operatively.

Post image processing, an initialization substep may be performed to determine the initial pose of the mean model. The initialization may be based on a hybrid classifier combining k-nearest neighbor and support vector machine, as shown in FIG. 59.

Figure 60:
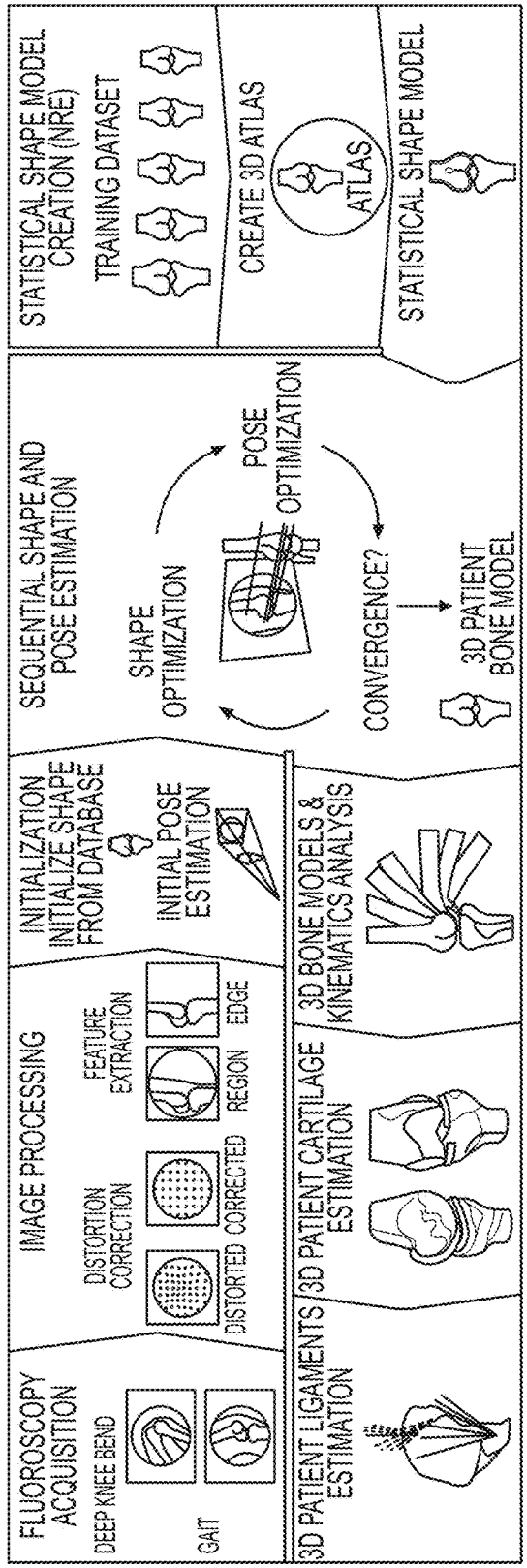
FIG. 60 is a flow diagram depicting an exemplary process of creating anatomical information from dynamic image data.
Figure 61:
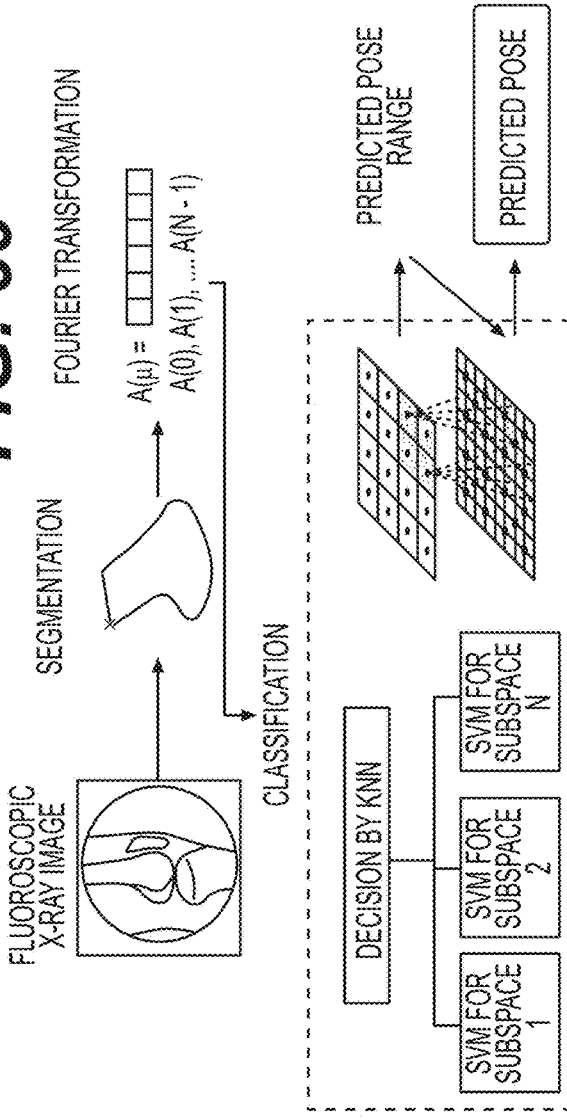
FIG. 61 is a diagram depicting initialization with a hybrid classifier.

As depicted in FIG. 60, two primary methods of reconstruction have been developed for building 3D patient anatomy from fluoroscopy images. A first method, Method 1, comprises a sequential shape and pose estimation, whereas a second method, Method 2, comprises reconstruction using And-Or-Tree (AoT). A more detailed discussion of each of these models follows.

Figure 62:
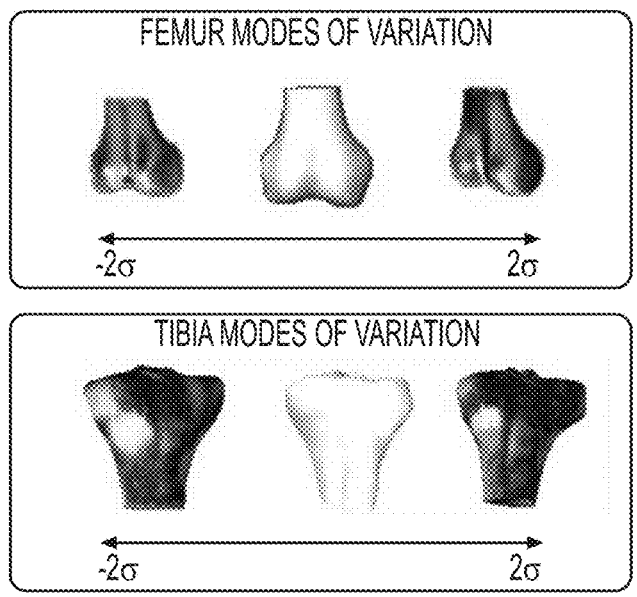
FIG. 62 is a diagram depicting KPCA model variation applied to a knee joint.
Figure 63:
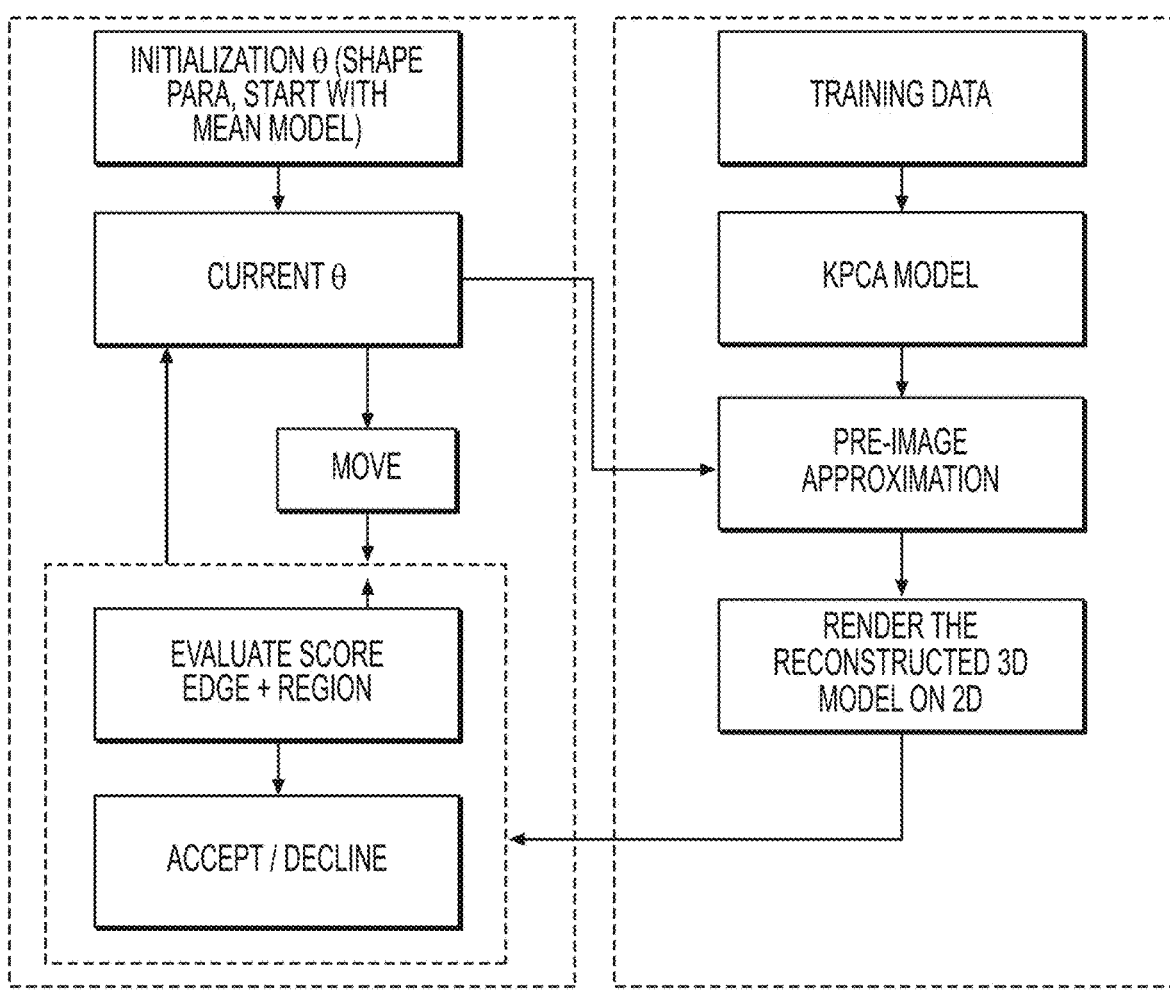
FIG. 63 is a diagram depicting a process for pose and shape parameter optimization.

A sequential shape and pose estimation 3D reconstruction may be based on a nonlinear statistical shape model, namely kernel principal component analysis (KPCA). By projecting the training data onto high-dimensional kernel space, the shape of the 3D model may be represented by a vector of shape parameters, as shown in FIG. 62. As part of this method, an optimization process may be carried out where the optimization determines the 3D model's shape and pose parameters from a sequence of monoplane fluoroscopic X-ray images, as shown in FIG. 63. Optimization may be based on a novel energy function, which combines the edge, region, homogeneity, and multi-body registration score to measure the similarity between the 3D model and the 2D X-ray image, as shown in Table 1. The hybrid energy function requires neither time-consuming DRR generation nor error-prone 2D segmentation.

Thereafter, the 3D model may be reconstructed by a pre-image approximation, because the map between the input and feature space points is not necessarily known. It is preferred to reconstruct the pre-image of the corresponding test point based on the distance constraint in the input space. This may be achieved by establishing the relationship between input-space distance and feature-space distances, as shown in FIG. 64.

Figure 65A:
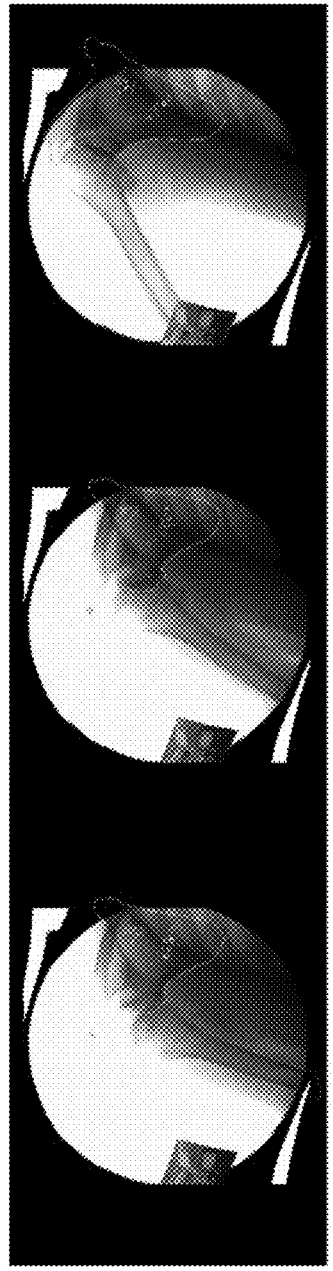
FIG. 65 comprises exemplary images of shoulder and hip reconstruction from X-ray fluoroscopy.
Figure 65B:
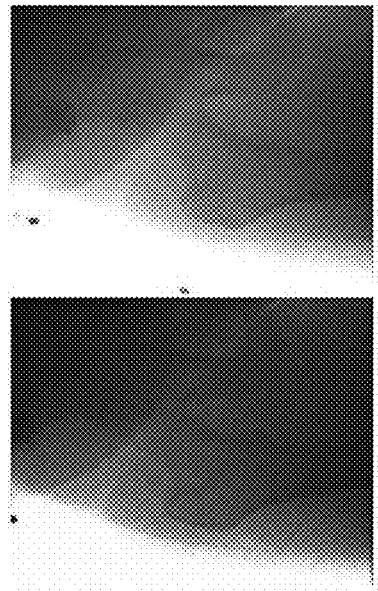

Alternatively, as depicted in FIG. 65, the reconstruction may be performed with the AOT technique. Initially, the geometry space is decomposed by extracting volumes of interest (VOI) as volumes where part templates may exist. Each VOI may be further divided into a set of overlapping sub-volumes, which may be used as bounding volumes for the placement of part templates. The examples of the sub-volumes are shown on the node on the left side of FIG. 65. The "And-or tree" may be generated recursively by partitioning volumes and representing partitions by And-or node pairs. The "or node" may connect to all the "and nodes" that slice the volume represented by this "or node" into two sub-volumes. The "or node" may also connect to two sets of leaf nodes, where on each node a surface is placed by either inscribing the volume or on the surface perpendicular to the depth direction. Each "and node" may connect two or more nodes, with each representing one of the two smaller sub-volumes occupying the current sub-volume. This tree starts from a root "OR node" representing the volume of interest (VoI), and keeps growing until the sub-volumes are divided to a size limit. Using surface as bounding boxes, appearance of part templates may be further defined. Possible appearance for each part template may also be represented by an "and-or tree," where "and" represents composition and "or" represents deformation. Layers of "and nodes" may decompose the part templates into curve segments. These curves may be projected onto image plane. The 3D object template may be converted to a 2D object template composed of active curves, which may resemble object appearance in the image plane. The deformed active curves may then be projected back into the object space as the reconstructed 3D model.

Figure 66:
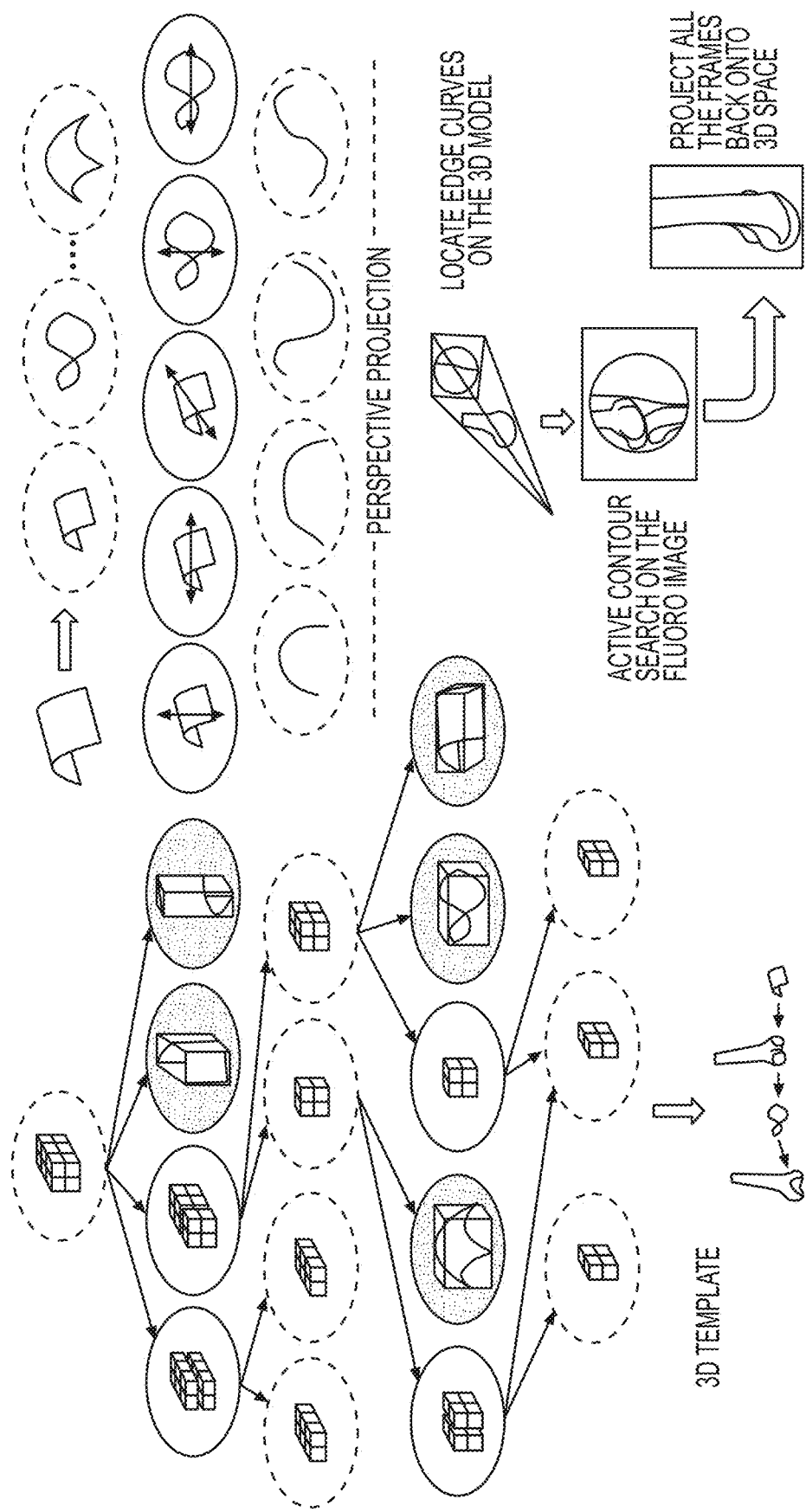
FIG. 66 is a diagram depicting how the geometry space is first decomposed by extracting volumes of interest (VOI) as volumes where part templates may exist.

As shown in FIG. 66, the volume of interest (VoI) is determined by detection. The shape of a generic model may be learned from different known poses by optimizing information gain. Then, templates may be projected onto 2D image planes as active contours, which deform in image planes. The leaves of the appearance "And-or tree" may be projected onto 2D image planes as active contours. At part level, templates may perform in-plane translation, rotation, which is called 3D deformation. Projected active curves may also be allowed to deform in 2D. Both 2D and 3D deformation may be guided by maximizing the information gain. By projecting the deformed active curves back to the object plane, the 3D model may be reconstructed.

Figure 67:
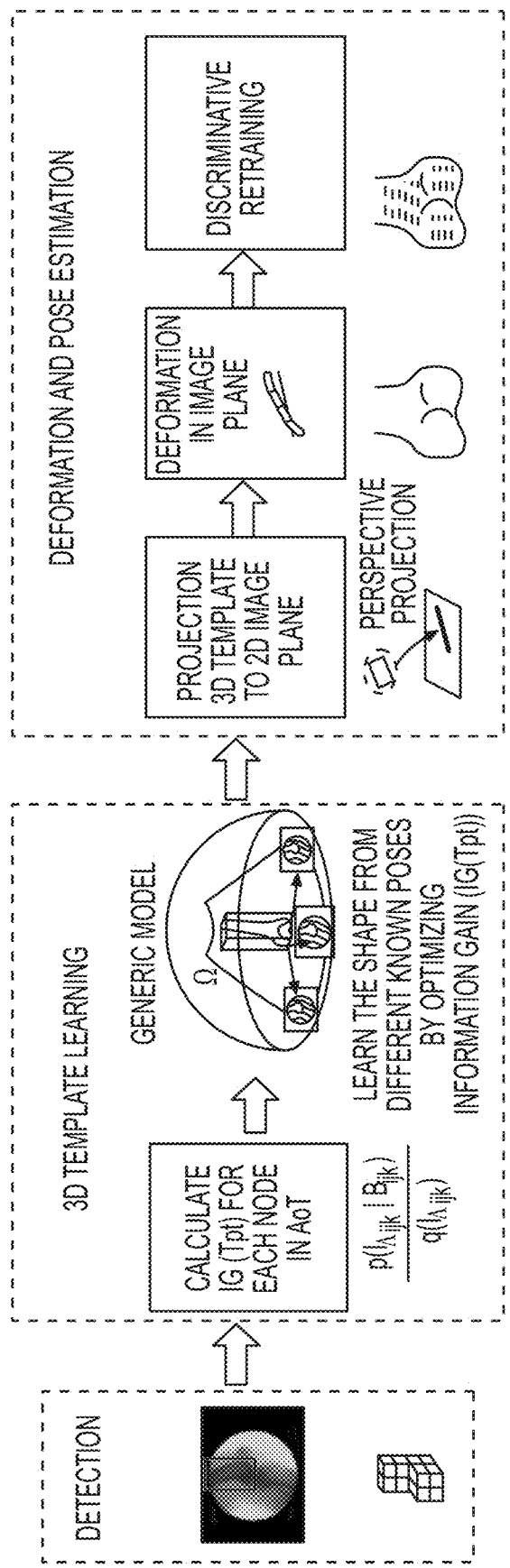
FIG. 67 is a diagram depicting how the volume of interest (VoI) is determined by detection.
Figure 68:
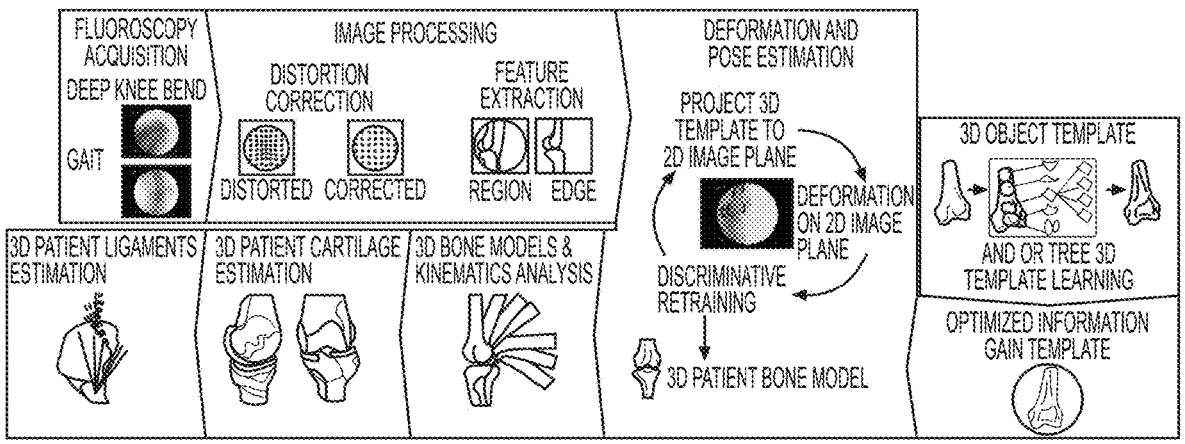
FIG. 68 is a diagram depicting one alternative to using statistical shape deformation is to identify features on the image directly and use the so-called And-Or Tree for shape identification and deformation.
Figure 69:
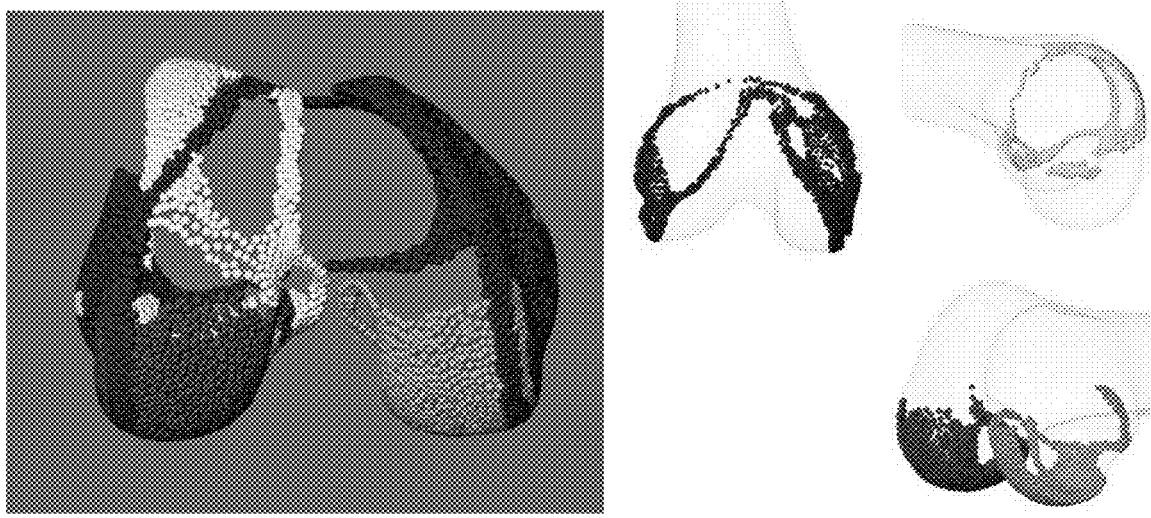
FIG. 69 is a series of computer generated illustrations decomposing femoral anatomy into primitive shapes.

As depicted in FIGS. 67-69, one alternative to using statistical shape deformation may be to identify features on the image directly and use the so-called "And-Or Tree" for shape identification and deformation (see Hu, Wenze, and Song-Chun Zhu. "Learning 3d object templates by quantizing geometry and appearance spaces." IEEE transactions on pattern analysis and machine intelligence 37.6 (2015): 1190-1205, the disclosure of which is incorporated herein by reference. In the foregoing publication, the shape parameters for the bone anatomies are dictated by the structure of the AoT and the identification of those structures in the fluoroscopy frames.

It is worth mentioning that for the knee, it is required that, at minimum, the knee portion of the joint be created (distal femur and proximal tibia). However, the same approach could be applied to any joint.

D. Image Processing

Because fluoroscopy is prone to image distortion, it may be desirable to correct this distortion prior to analyzing the image data. Using a calibration target, this distortion may be estimated and removed from subsequent images. A step in the calibration procedure may include estimating any 2D image's geometric distortion. By taking an image of a known rectangular grid of metal beads, a 2D spatial transform for each small square sub-image that is bounded by four beads can be estimated. Using standard techniques in geometric distortion removal, a local bilinear model may be used to model the spatial mapping, as well as the gray level interpolation. Once the 2D distortion has been removed, the effective source-to-image plane distance (focal length) may be computed by a two-plane calibration grid with a known displacement between the planes. FIG. 16 illustrates the fluoroscopic image of a geometric calibration grid before and after geometric distortion removal. A bilinear transform for each set of four grid points may be computed that transforms the image positions of the beads in the left image to regularly spaced grid locations in the right. This correction may be applied to each fluoroscopic image acquired during the procedure. Distortion correction may not be required for planar X-ray images.

Initialization

Initialization may be performed to determine the initial pose of the mean model. Initialization may be performed based on a hybrid classifier combining k-nearest neighbor and support vector machine. Other options may include manually initializing the models or utilizing other machine learning frameworks, such as CNN or similar deep learning structures to train and classify poses from images. The output of the initialization step may comprise a template model and the appropriate pose of the model relative to the image plane in at least one frame of the fluoroscopy images.

Optimization

Figure 17:
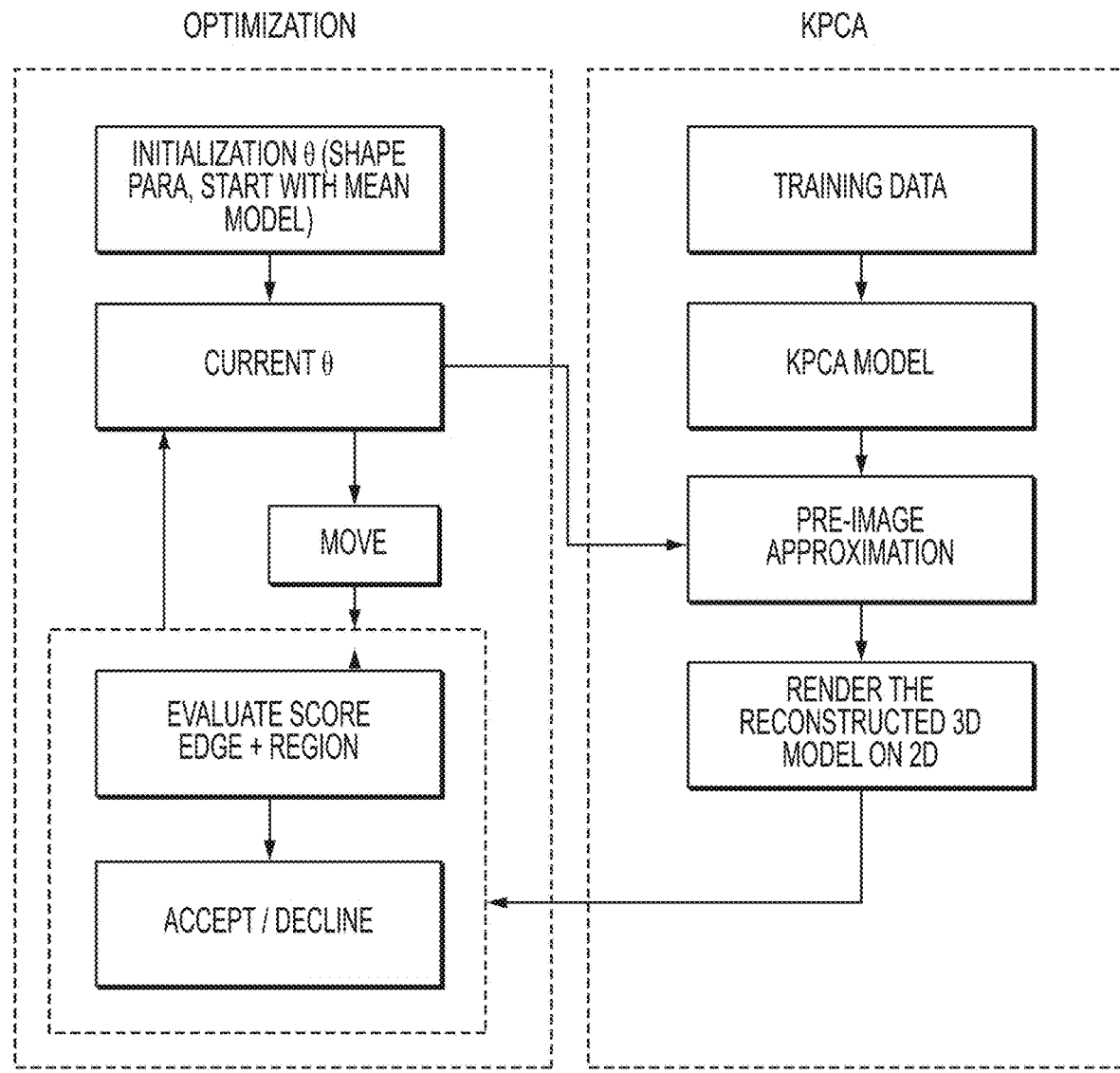
FIG. 17 is an exemplary pose and shape parameter optimization process flow in accordance with the instant disclosure.
Figure 22:
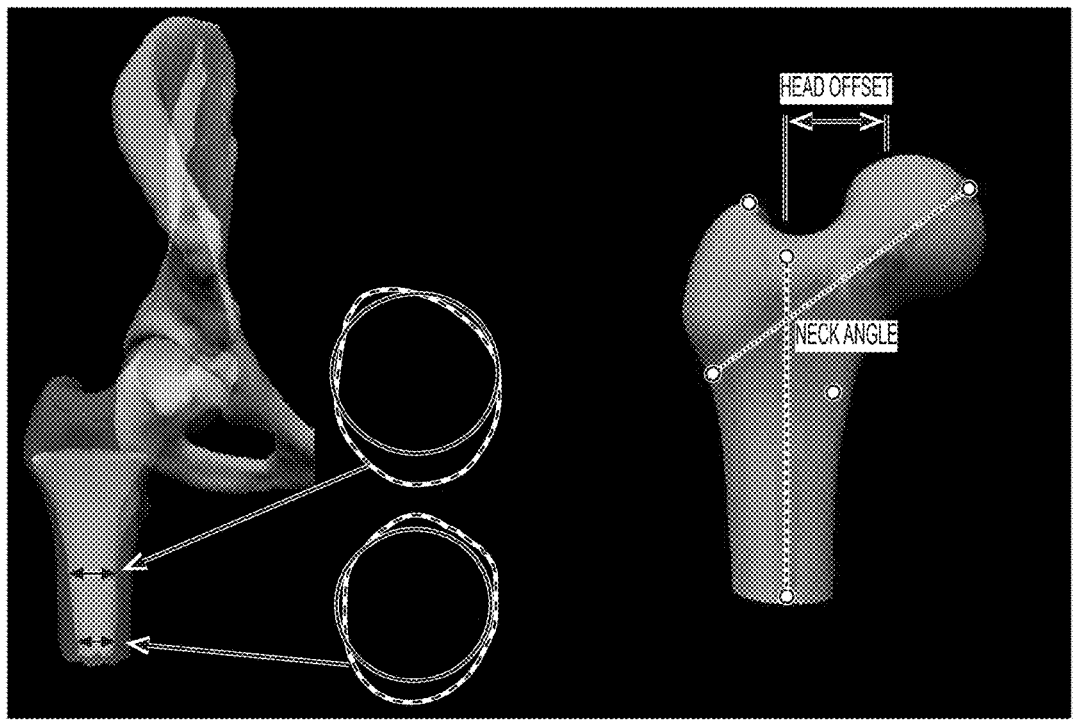
FIG. 22 is a partial screen shot depicting generic templating of stem and femoral measurements by way of intramedullary canal geometry to assess different implant locations that is used to compute the optimal implant diameter, neck angle, and head offset.

Optimization may include determining the 3D model's shape and pose parameters from a sequence of monoplane fluoroscopic X-ray images, as shown in FIG. 17. Optimization may be based on a novel energy function, which combines the edge, region, homogeneity, and multi-body registration score to measure the similarity between the 3D model and the 2D X-ray image, as shown in Table 1. The hybrid energy function requires neither time-consuming DRR generation nor error-prone 2D segmentation.

PreImage

The 3D model may then be reconstructed by a pre-image approximation, because the map between the input and feature space points is not necessarily known. Reconstruction of the pre-image of the corresponding test point may be based on the distance constraint in the input space. This may be achieved by establishing the relationship between input-space distance and feature-space distances, as shown in FIG. 18.

II. Surgical Planning

A. Static Surgical Planning

In any of the configurations of the exemplary systems disclosed herein, relevant surgical landmarks may be manually and/or automatically calculated (see FIG. 19), where these calculated surgical landmarks may be used to establish a coordinate system for measuring implant placement.

Prior to placing or guiding the placement of a surgical implant, it may be desirable that a virtual surgical plan be created through a process of virtual templating, or surgical planning. It may be desirable that the virtual templating be performed with 3D templates of the identical implants to be used in surgery. However, if no such implant is available, the templating may be done in an implant independent way, using generic implant virtual templates, which may be designed to mimic the shape and size of known surgical implants.

The virtual templating program may receive 3D patient-specific models from either or both an auto segmentation program and a non-rigid registration program. In the context of a hip joint, the 3D patient-specific models may include the pelvis and the femur, which are both input to an automatic landmarking program. This automatic landmarking program calculates anatomical landmarks relevant to implant placement on the femur and pelvis 3D models using regions from similar anatomy present in a statistical atlas and local geometrical searches.

Figure 80:
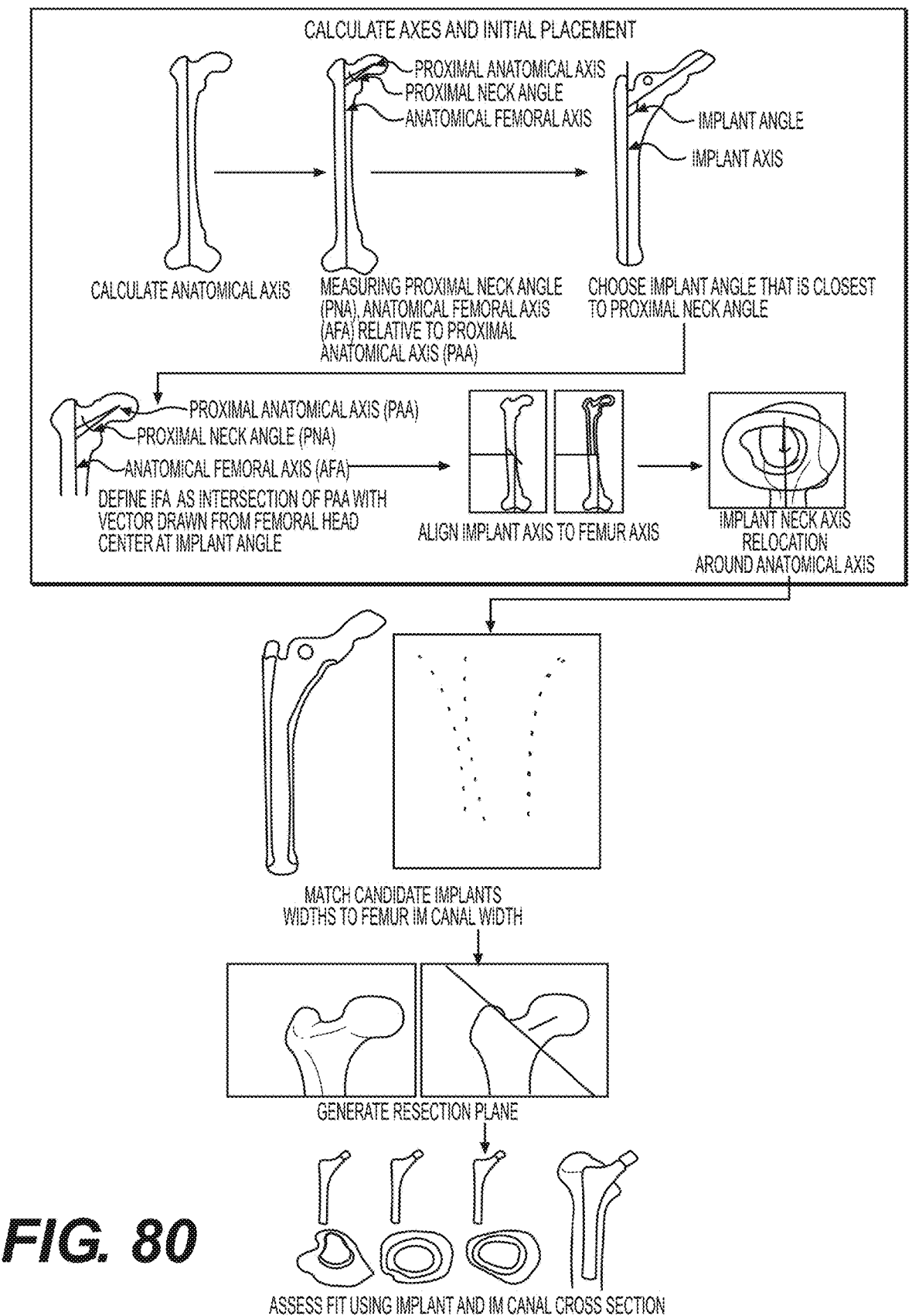
FIG. 80 is an exemplary process diagram for automatic femoral stem placement using distal fixation.

In the context of automatic placement of the femoral stem using distal fixation, as shown in FIG. 80, the automatic landmarking may include definition of axes on the femur and the implant. With respect to the femur, the anatomical femoral axis (AFA) may be calculated, followed by the proximal anatomical axis (PAA). The proximal neck angle (PNA) may then be calculated, which is defined as the angle between the AFA and PNA. With respect to the femoral implant, the implant axis is along the length of the implant stem and the implant neck axis is along the length of the implant neck. Similar to the PNA of the femur, the implant angle is defined as the angle between the implant axis and the implant neck axis. The implant may then be chosen that has an implant angle that may be closest to the PNA. The implant fitting angle (IFA) may then be defined as the intersection of the proximal anatomical axis with a vector drawn from the femoral head center at the chosen implant angle.

When using automatic placement of the femoral stem using distal fixation and the calculated anatomical landmarks, as shown in FIG. 80, an implant sizing step may be used to determine/estimate, for the appropriate implant sizes, the femoral components. The implant size may be chosen by comparing the width of the implant to the width of the intramedullary canal and selecting the implant with the most similar width to the intramedullary canal. Thereafter, the program may move forward to an implant placement step.

In an exemplary implant placement step for a distal fixation femoral stem, based on surgeon preferred surgical technique and previously calculated anatomical landmarks, the initial implant position may be determined/chosen for all relevant implanted components. A resection plane may then be created to simulate the proximal femur osteotomy and the implant fit may be assessed. Fit assessment may be conducted by analyzing the cross sections of the aligned implant and femur intramedullary canal at varying levels along the implant axis. The implant may be aligned to the femur by aligning the implant axis to the anatomic femur axis then translating the implant so that the neck of the implant is in the general location of the proximal femur neck. The implant may then be rotated about the anatomic femur axis to achieve desired anteversion.

As part of this exemplary implant placement step, an iterative scheme may be utilized that includes using an initial "educated guess" as to implant placement as part of a kinematic simulation to evaluate the placement of the "educated guess." In exemplary form, the kinematic simulation may take the implant (based upon the placement of the implant chosen) through a range of motion using estimated or measured joint kinematics. Consequently, the kinematic simulation may be used to determine impingement locations and estimate the resulting range of motion of the implant post implantation. In cases where the kinematic simulation results in unsatisfactory data (e.g., unsatisfactory range of motion, unsatisfactory mimicking of natural kinematics, etc.), another location for implant placement may be utilized, followed by a kinematic analysis, to further refine the implant placement until reaching a satisfactory result.

Figure 81:
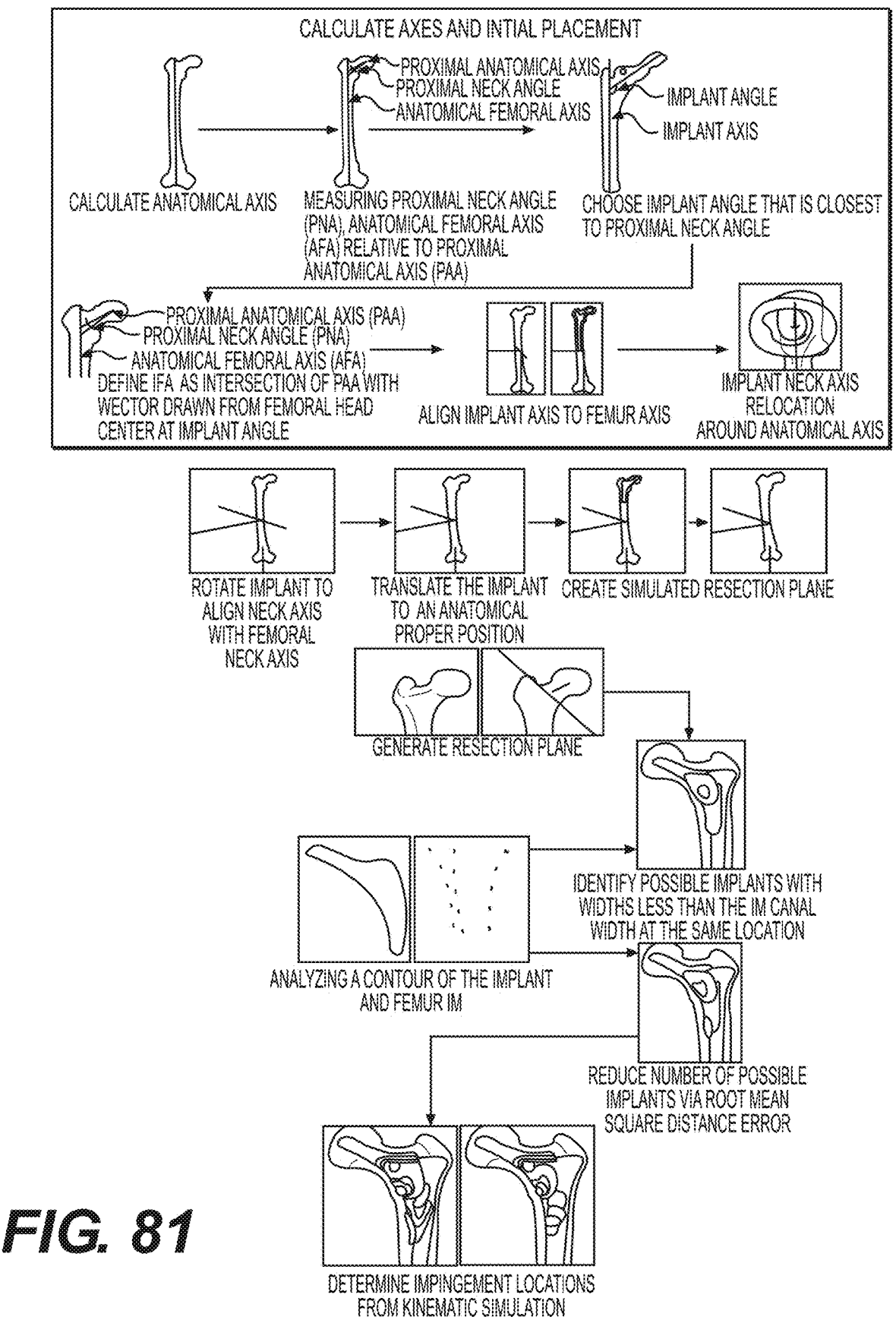
FIG. 81 is an exemplary process diagram for automatic femoral stem placement using press fit and three contacts.

In the context of automatic placement of the femoral stem using press fit and three contacts, as shown in FIG. 81, the automatic landmarking may include definition of axes on the femur and the implant. With respect to the femur, the anatomical femoral axis (AFA) may be calculated, followed by the proximal anatomical axis (PAA). The proximal neck angle (PNA) may then be calculated, which is defined as the angle between the AFA and PNA. With respect to the femoral implant, the implant axis is along the length of the implant stem and the implant neck axis is along the length of the implant neck. Similar to the PNA of the femur, the implant angle is defined as the angle between the implant axis and the implant neck axis. The implant may then be chosen among various implants as having an implant angle that is closest to the PNA. The implant fitting angle (IFA) may then be defined as the intersection of the proximal anatomical axis with a vector drawn from the femoral head center at the chosen implant angle.

When using automatic placement of the femoral stem using press fit, three contacts, and the calculated anatomical landmarks, as shown in FIG. 81, an implant sizing step may determine/estimate the appropriate implant size for pelvis and femoral components. The implant size may be chosen by aligning the implant to the femur by aligning the implant axis to the anatomic femur axis. The implant may then be rotated to align its neck axis with the femoral neck axis. The implant may then be translated to be in an anatomically proper position within the proximal femur. Thereafter, the system may move forward to an implant placement step.

In an exemplary implant placement step for a press fit femoral stem, based on surgeon preferred surgical technique and previously calculated anatomical landmarks, the initial implant position may be determined/chosen for all relevant implanted components. A resection plane may be created to simulate the proximal femur osteotomy and the implant fit may be assessed. Fit assessment may be conducted by analyzing a contour of the implant and femur intramedullary canal. The contour may be created by intersecting the intramedullary canal with a plane normal to both anatomical axis and femoral neck axis, passing through the point of intersection of the anatomical axis and femur neck axis, producing a contour. When the implant and intramedullary canal contours are generated, only the implants with widths less than the intramedullary canal width at the same location are kept, resulting in many possible correct implant sizes. The group of possible sizes may be reduced through two strategies reducing mean square distance error between the implant and the intramedullary canal. The first strategy minimizes the mean square error (MSE) or other mathematical error metric of the distance between both medial and lateral sides of the implant and the intramedullary canal. The second strategy minimizes the MSE of the distance between the lateral side of the implant and the intramedullary canal.

As part of this exemplary implant placement step, an iterative scheme may be utilized that includes using an initial "educated guess" as to implant placement as part of a kinematic simulation to evaluate the placement of the "educated guess." In exemplary form, the kinematic simulation may take the implant (based upon the placement of the implant chosen) through a range of motion using estimated or measured joint kinematics. Consequently, the kinematic simulation may be used to determine impingement locations and estimate the resulting range of motion of the implant post implantation. In cases where the kinematic simulation results in unsatisfactory data (e.g., unsatisfactory range of motion, unsatisfactory mimicking of natural kinematics, etc.), another location for implant placement may be utilized, followed by a kinematic analysis, to further refine the implant placement until reaching a satisfactory result.

In an alternative embodiment of a surgical planning program, the templating need not require a database of implant 3D CAD models. Instead, the program may compute anatomical acetabular cup diameters and depths. The program may utilize a set of generic cup implants (hemispheres) to template the cup placement relative to the surgical landmark (see FIG. 21).

B. Dynamic Surgical Planning for the Knee

The surgical planning program, while described in detail previously for the hip, may also be used for any of the other joints that are candidates for arthroplasty—such as, without limitation, knee, hip, ankle, elbow, shoulder or similar. For many joints, specifically the knee, it may be important to not only analyze the static geometry and landmarks during templating, but also the dynamic information coupled with the soft tissues of the joint. The virtual templating program utilizes sensor motion data and 3D data captured during the preoperative imaging to determine optimal sizing and positioning.

Referring to FIG. 59, the bone and soft tissue reconstruction substep 22 may include predicting soft tissues and normal anatomy using the dynamic images obtained in substep 21. As part of standard implant design, or patient specific implants and instruments, one relies on static CT or MRI to extract morphology of the joint. However, morphology is usually altered by disease or deformity. In the case of osteoarthritis of the knee, the cartilage may be lost and osteophytes present change the morphology of the knee. Using static CT and MRI may not describe the joint's ligament condition accurately. For example, collapse of the medial compartments in the knee in addition to the presence of osteophytes growth change the Medial Collateral Ligament (MCL) and Lateral Collateral Ligament (LCL) dynamic behavior. Given these large changes on soft tissue and bone, extraction of bone contours becomes difficult, inaccurate, and sometimes impossible. In this situation, statistical atlases of specific population may be used to predict the original deformed bone shape in addition to accurately predict ligament locations and then dynamically extract design parameters and curvature for this specific patient. Rather than rely on static images to generate patient specific implants and instruments, the instant exemplary embodiment uses static images in addition to kinematic data (dynamic data) to generate implants and instruments that are optimized both for replicating patient anatomy and kinematics. Prior art patient specific implants and instruments are, at best, optimized only for replicating patient anatomy, but ignore kinematics or fail to use kinematics as an element of the ultimate shape of the orthopedic implant.

Figure 70:
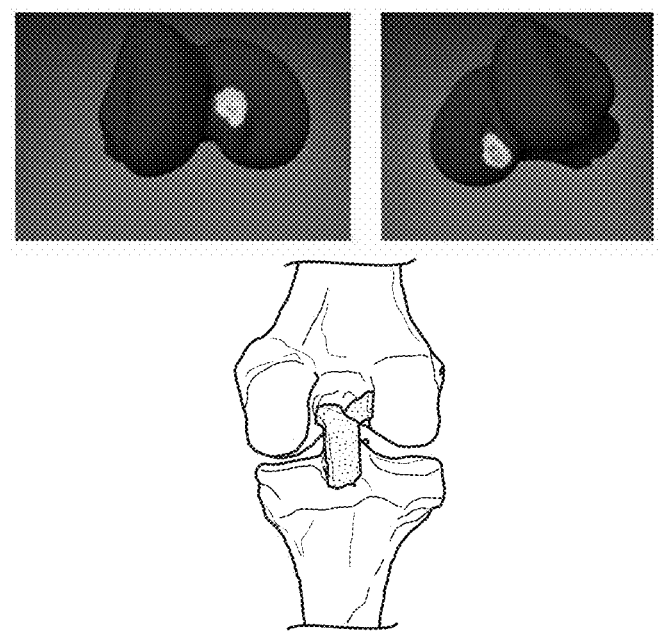
FIG. 70 is a bone model showing ligament locations having been extracted from imaging data.

Turning to FIG. 70, as part of reconstructing the soft tissue associated with the virtual bone model, ligament locations may be extracted from imaging data. In particular, the surface models of the bone and ligaments may be reconstructed from MRI. The bone models may be added to a statistical atlas and each vertex may be flagged as either belonging to the attachment site or not based on distance to the ligament surface model. Performing this step for multiple subjects allows for creation of a probability map for each ligament attachment site (shown in a top row for femoral attachment sites of ACL and PCL in FIG. 70). In the map, each bone atlas vertex may be assigned a probability of belonging to the attachment site.

Figure 71:
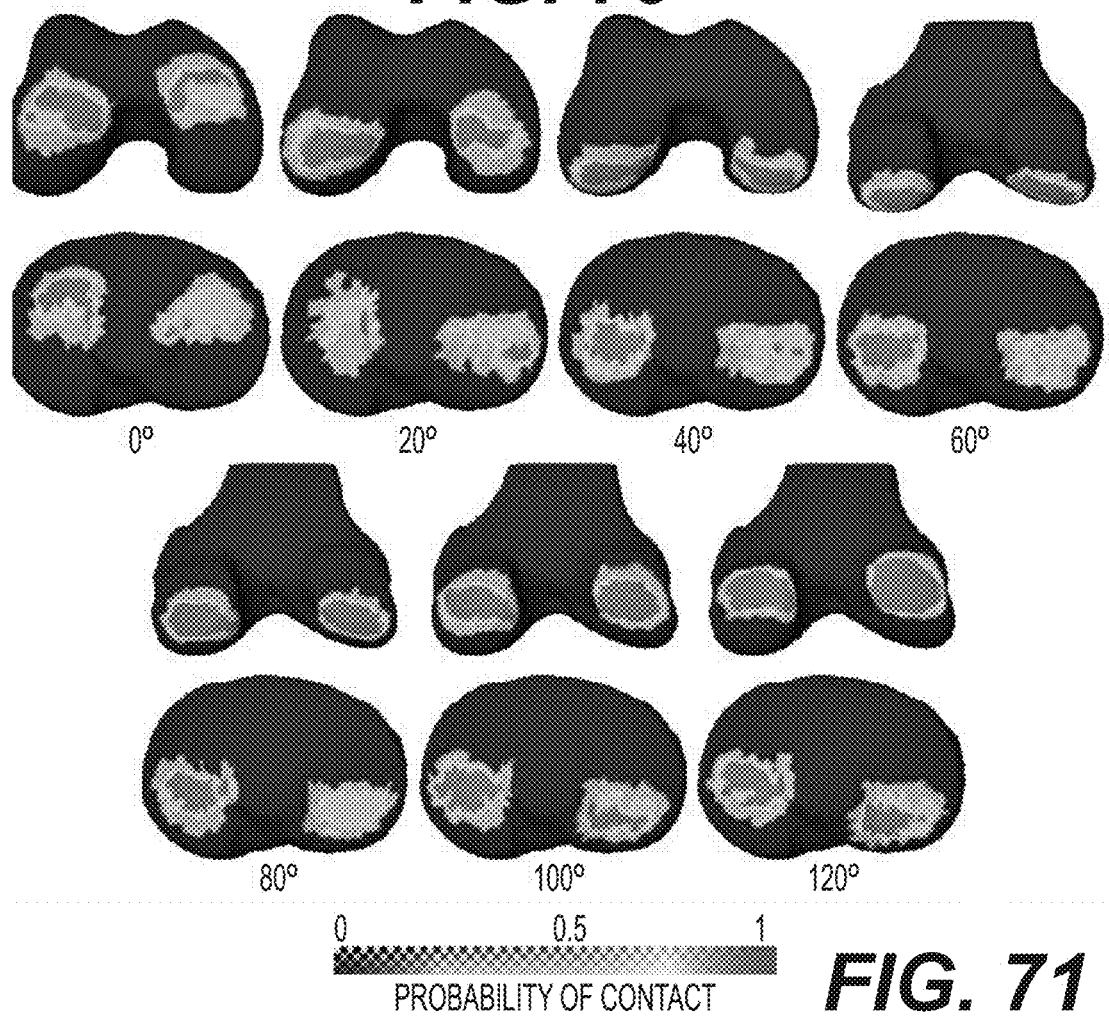
FIG. 71 is a diagram depicting contact maps of the tibia and femur for a deep knee bend.

Referencing FIG. 71, as further part of the bone and soft tissue reconstruction substep 22 (see FIG. 59), contact maps for the femur and tibia may be created during deep knee bend. For a single subject, both femur and tibia may be assigned vertex correspondence to the respective bone atlases. The pose of the femur relative to the tibia may be updated at each flexion angle. At each pose, the vertices of the femur and tibia belonging to the contact regions may be determined based on proximity to the articulating bone. Performing this analysis across multiple subjects allows for creation of a probability map on each bone, at each flexion angle, of contact regions.

Figure 72:
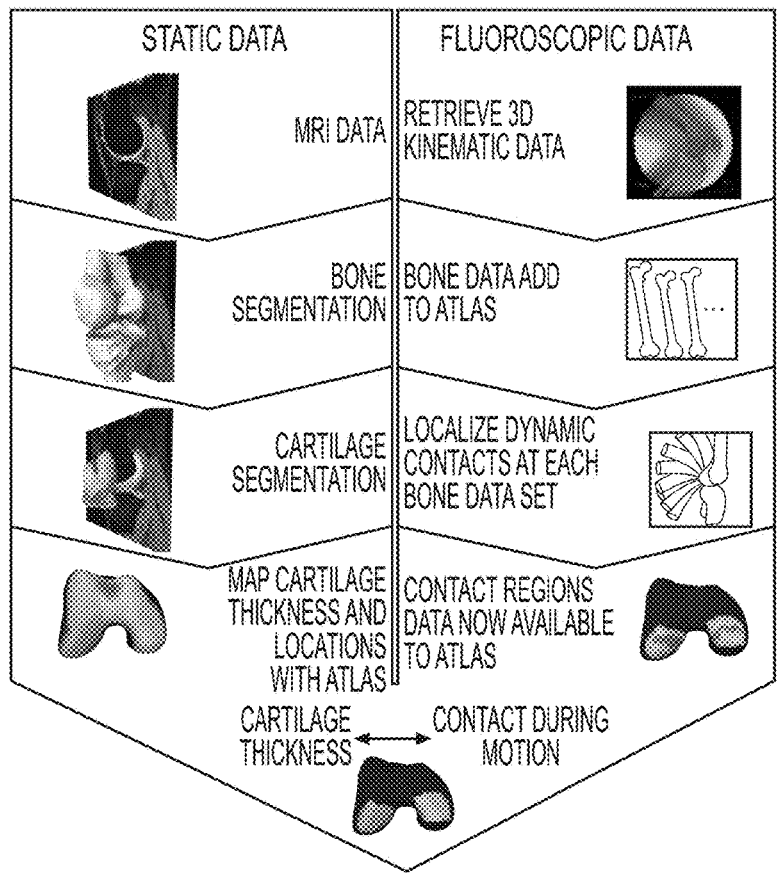
FIG. 72 is a diagram depicting how static data and fluoroscopic data are utilized to couple kinematics and morphology.

FIG. 72 depicts inputs and outputs associated with an exemplary method for determining cartilage thickness within contact regions during a deep knee bend (such as recorded during the dynamic imaging substep 21 in FIG. 59). This method may be used to map the contact regions, determine true patient specific thickness, and tie this information back into the previously created normal statistical atlas. In this fashion, kinematics is coupled to morphology.

Figure 73:
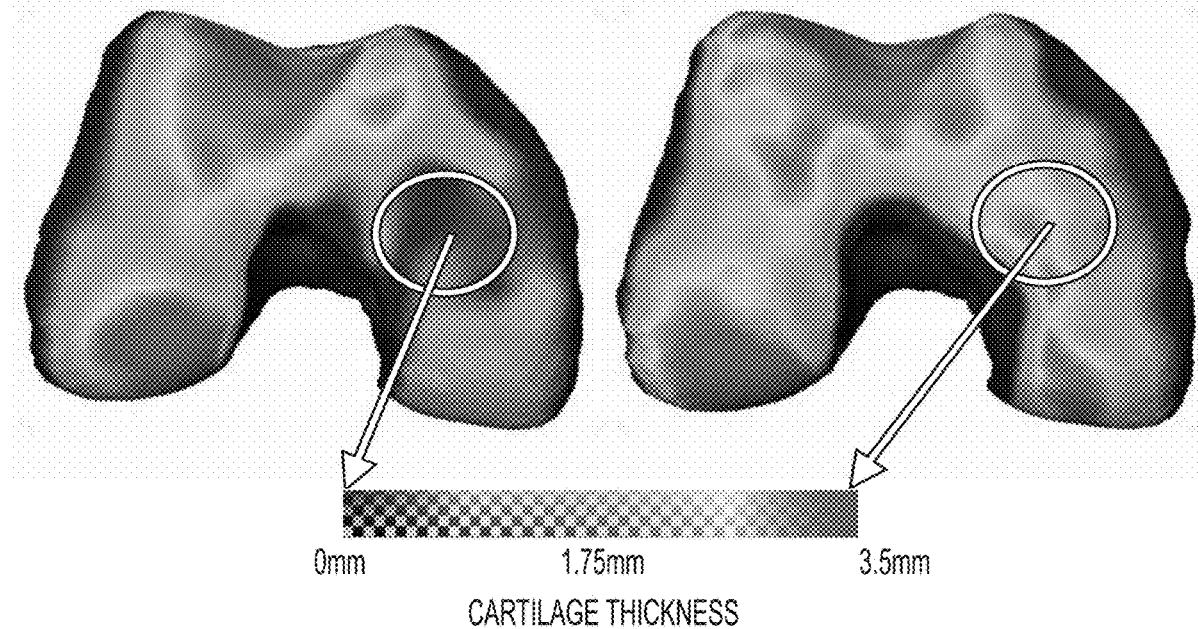
FIG. 73 is a map of two distal femurs showing relative cartilage thicknesses as part of dynamic image taking.

FIG. 73 depicts a patient specific cartilage map (obtained from kinematic analysis, substep 21 in FIG. 59) showing severe cartilage loss in the medial compartment. Creating a patient specific implant with only this information would lead to poor implant functionality. Instead, the instant embodiment may use statistical methods to estimate of the morphology before a deformity is created, thereby allowing for true patient specific (prior to pathology) curvature extraction. And this estimated morphology leads to greater implant functionality.

Figure 74:
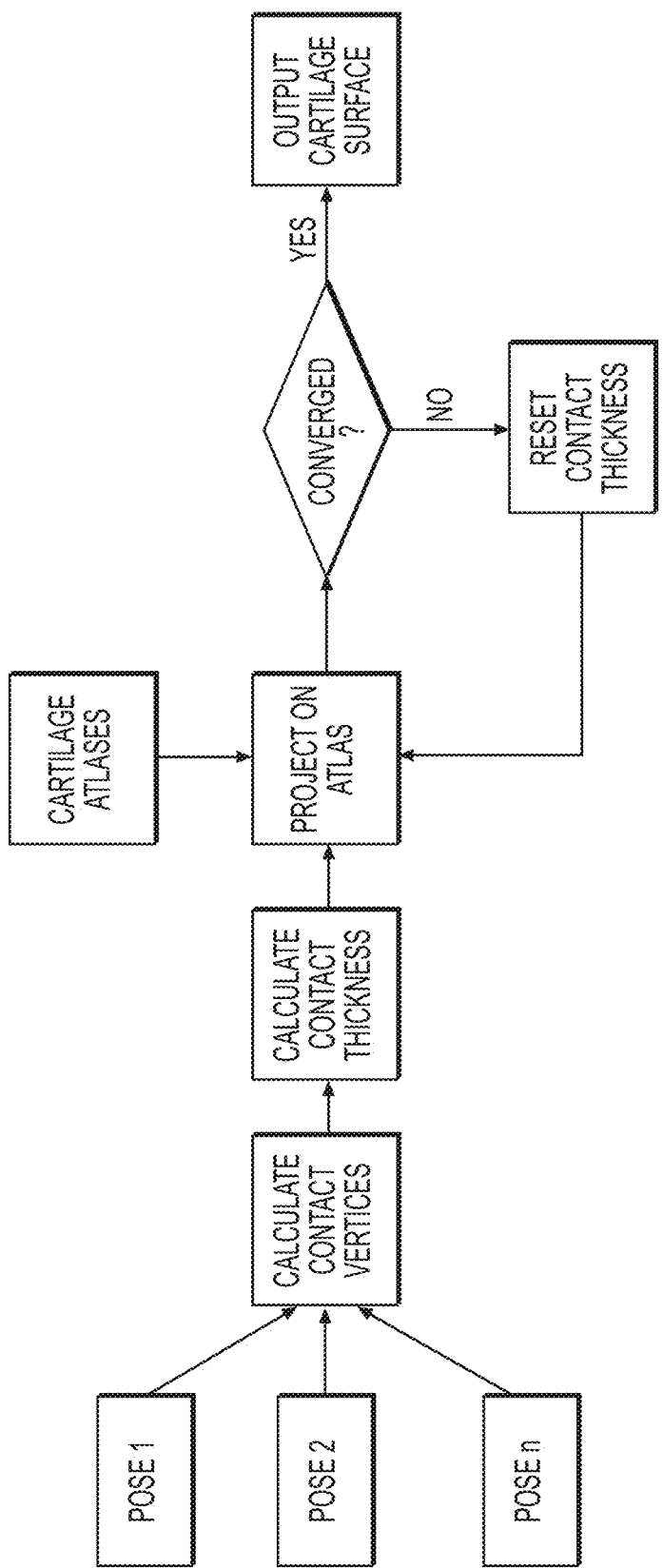
FIG. 74 is a flow diagram for estimating cartilage thickness from dynamic data.

Referencing FIG. 74, a flow diagram is depicted for estimating cartilage thickness from dynamic data in accordance with the instant disclosure. Given multiple poses of articulating surfaces—the knee, for example—the contact at each pose may be determined. Contact may be primarily determined using a small percentage of the closest points between each model. For each contact point, the distance between the point and the articulating model may be determined. The cartilage thickness can then be estimated as X % from model 1, Y % of model 2 so that the sum of the two thickness values equals the total distance between the surfaces. Calculating the thickness at each contact vertex at each pose provides a set of "known" thicknesses that are to be kept constant during the estimation procedure. This set can be considered convex set 1 in the projection on convex sets (POCS) algorithm. Convex set 2 is the cartilage atlases, which previously calculated from a priori datasets—these cartilage atlases can include normal anatomy, specific pathological cohorts (varus, valgus in case of knee) or a combination thereof. As per the POCS algorithm, convex set 1 is projected onto convex set 2, the result of which is projected back on convex set 1—this is repeated until the result converges. In the described algorithm, the projection on the atlas updates all vertices belonging to the cartilage. If the result has not converged, the vertices belonging to the cartilage are set to convex set 1 (the "known" thicknesses) and projected back onto the atlas until convergence is reached. When converged, the surface of the cartilage on each articulating bone model is exported. This routine allows accurate estimation of cartilage by making use of dynamic data to capture full contact information.

Referring back to FIG. 59, upon reconstruction of bone shape, location of the ligaments may be predicted using ligament shape atlas, shape atlas has the ability to capture the loci of soft tissue across population, along with the probability of each point being a ligament loci as shown in FIG. 74. The calculated ligament insertion points may then be used to calculate the ligament length envelope during kinematic activities as shown in FIG. 75.

The basis for cartilage estimation may be a statistical model that contains a mean cartilage template and uses information from the segmented femur and tibia models to locally deform the mean cartilage template. The mean cartilage template may be the mean cartilage thickness calculated from a database of manually segmented cartilage models. Each thickness value has an index associated with it, corresponding to a point on the bone atlas, which is used to localize that value. When adding the mean template to a new bone model, each point on the bone may be warped outward along the normal direction a distance corresponding to the mean thickness from the template at that location. The mean cartilage template may be adjusted only when the femoral and tibial cartilage overlap. In this case the cartilage thickness may be reduced globally by a small factor and at areas of overlap by a larger factor. This process iterates until there are no areas of overlap.

Figure 76:
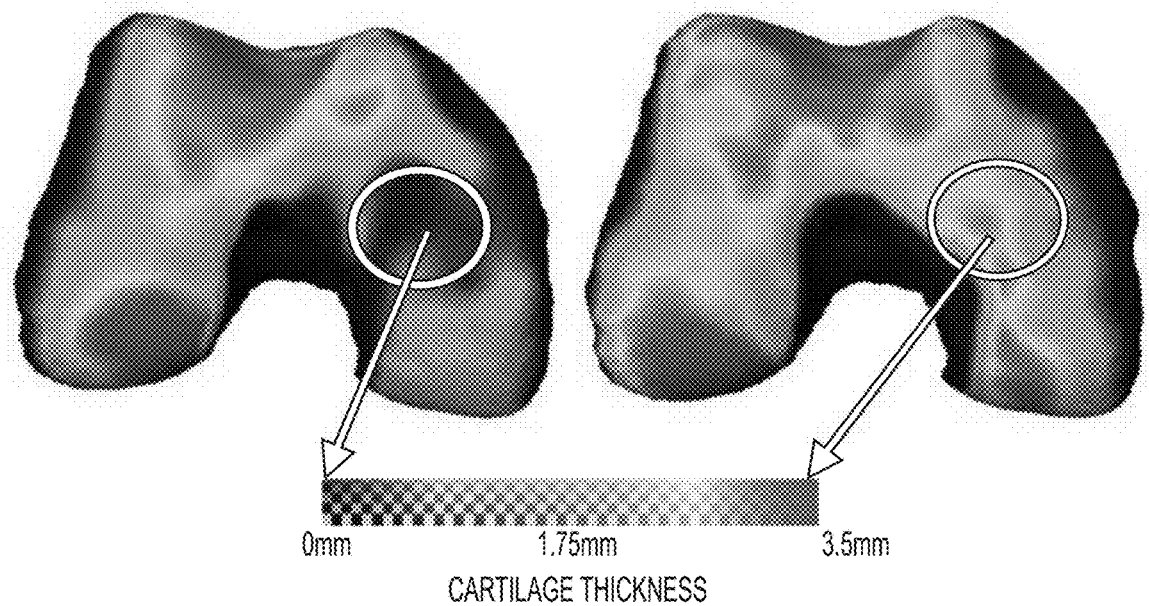
FIG. 76 is a pair of distal femur models mapping the amount of predicted cartilage loss.
Figure 77:
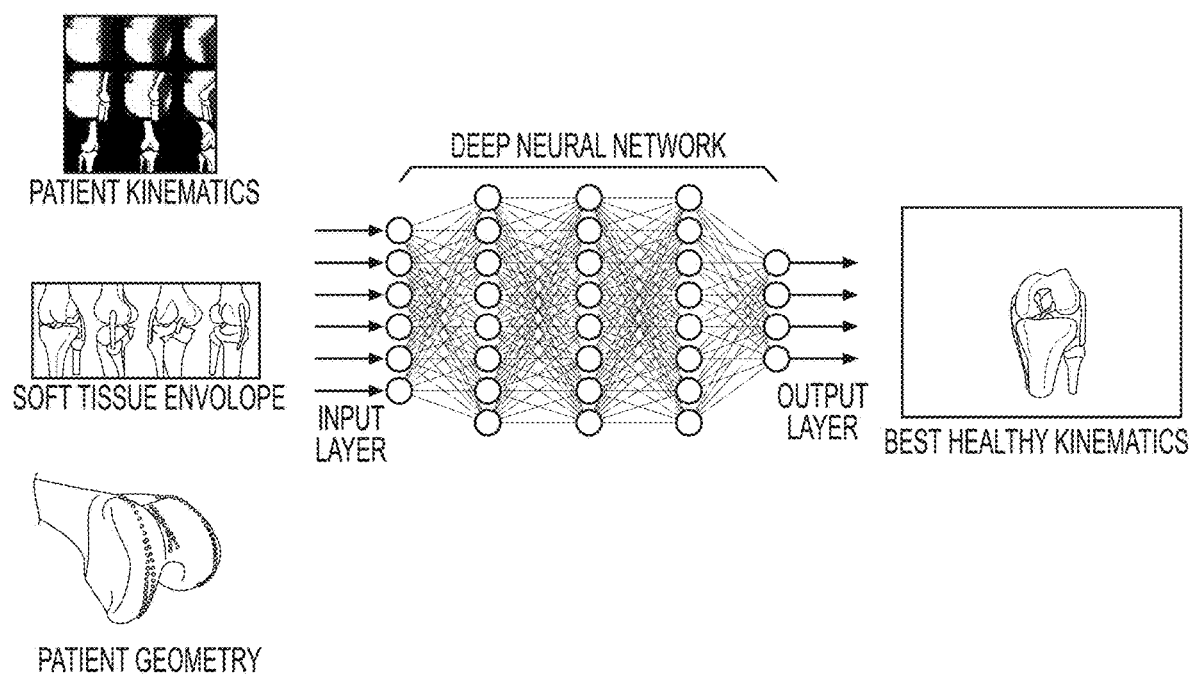
FIG. 77 is a process flow diagram for creating and using kinematic training networks for identifying kinematic patterns.
Figure 78:
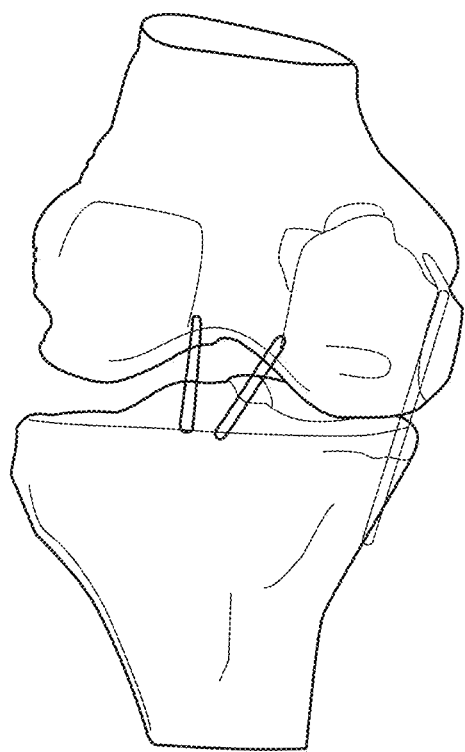
FIG. 78 is a knee joint bone model showing a collapse of a medial side.

Using estimated cartilage maps along with measured joint deformity, the location of cartilage loss may be determined and amount of cartilage loss may be estimated by projecting the patient cartilage on the normal cartilage model, as shown in FIG. 76. By correcting for the amount of cartilage loss, the joint may be put back into its normal alignment. This change in joint alignment directly affects ligament length and laxity. For example, loss of cartilage on the medial side will lead to laxity in the medial collateral ligament and increased tension in lateral collateral ligament as shown in FIG. 77. Restoring normal joint alignment change in ligament length may be calculated (see FIG. 78). Using soft tissue and morphology information the closest kinematic model from the normal kinematic database may be selected.

By way of example, determining normal healthy kinematics may be through the use of deep neural network, where the network may be trained by motions performed by healthy joints. The deep neural network may take pathological motion input and determine the optimal healthy kinematics (see FIG. 73).

Figure 79:
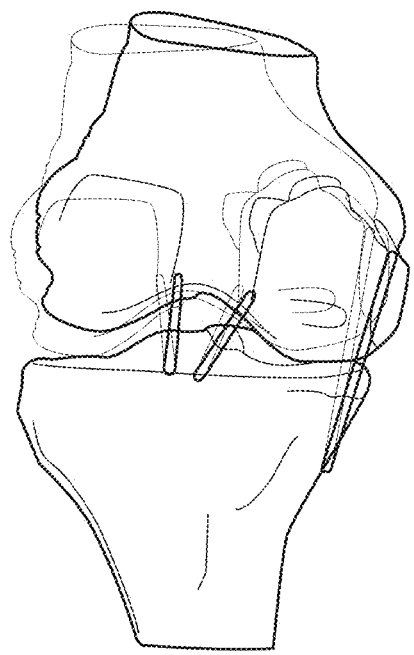
FIG. 79 is a knee joint bone model showing estimation of normal joint alignment and change in ligament length.

Referring to FIG. 79, a flow chart is provided depicting an exemplary process for calculating patient specific ligament stiffness as part of the normal kinematics prediction element in FIG. 59. In exemplary form, discussed with respect to an ankle arthroplasty procedure, a series of passive kinematic motion aspects may be recorded that include, without limitation, motion, speed of motion, acceleration of motion, and ligament length during the motion. These aspects may be used as inputs for a passive motion model, which also may receive inputs concerning ligament stiffness and mass of the tissues moved during motion. Using these inputs, the passive motion model may predict the force necessary to move the tissues. And this predicted force may be compared against a measured force to analyze whether the ligament stiffness values should be adjusted so that the predicted force equals the measured force. In circumstances where the predicted and measured forces are not equal or very closely similar, the ligament stiffness values and/or the mass inputs may be optimized and updated to allow subsequent predicted force calculations. This process may be repeated until the predicted and measured forces fall within acceptable tolerances of one another.

Figure 23:
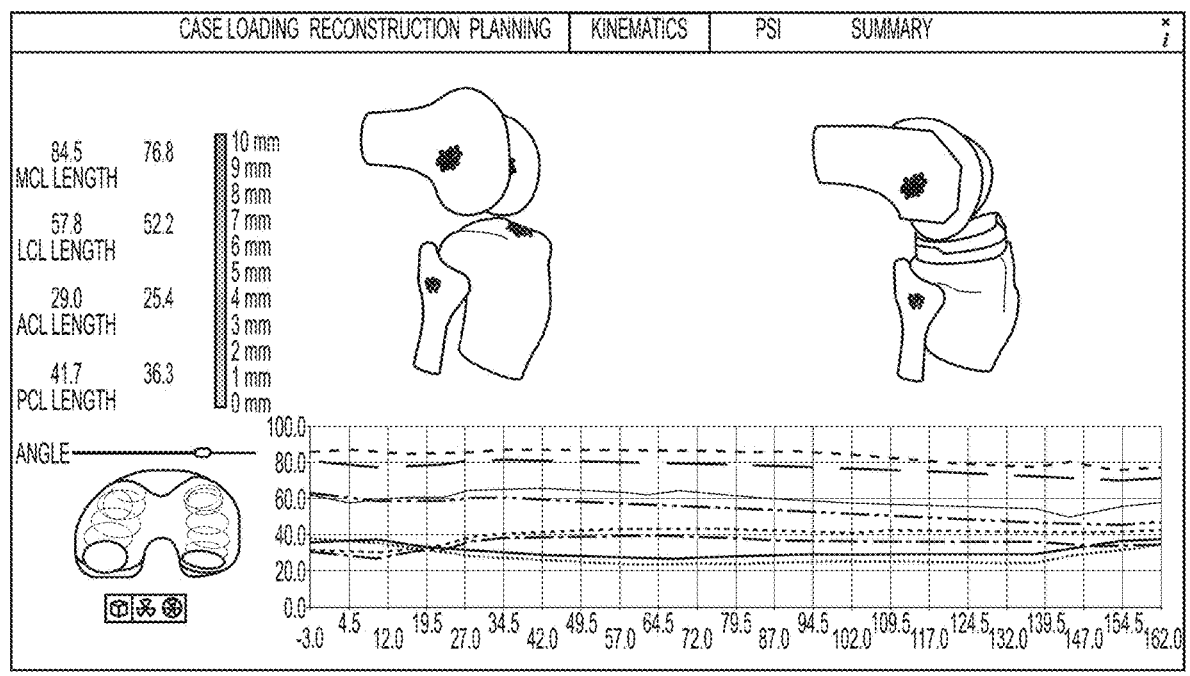
FIG. 23 is an exemplary screen shot of software demonstrating dynamic planning information including ligament tensions during different stages of the activities, and the contact map of the implants, in accordance with the instant disclosure.

Using the information generated from the dynamic and soft tissue analysis above, a virtual template of the femur, tibia and tibia inserts may be chosen from a family of implants to determine the best size and placement parameters so that the post-operative dynamic outcomes—motion, ligament lengths, tensions and femorotibial contacts—may be optimized for the patient (see FIG. 23). This optimization may begin with a default sizing and placement as determined by the patient joint geometry. This initial placement may then be adjusted automatically to account for desirable (or undesirable) corrections of the patient pathology and the effect of the corrections on the ligament locations and predicted contact areas. The planning software will present the pre-operative and post-operative predicted dynamic data and allow a user to inspect the results. If not satisfactory, the user may alter the position and/or sizing of the virtual implants, causing the software to re-analyze the predicted dynamic data which is again presented to the user. This process may continue until the user is satisfied. One example of unsatisfactory results would be if the choice of position or implant size causes a significant change relative to the preoperative anatomy in MCL or LCL length as predicted by the planning module. Such a large change may be indicative of overly tight or lax ligaments at this juncture of flexion, and may necessitate a change to the surgical plan. The output of this step is a pre-operative surgical plan optimized for the specific patient.

III. Anatomy Registration

Figure 24:
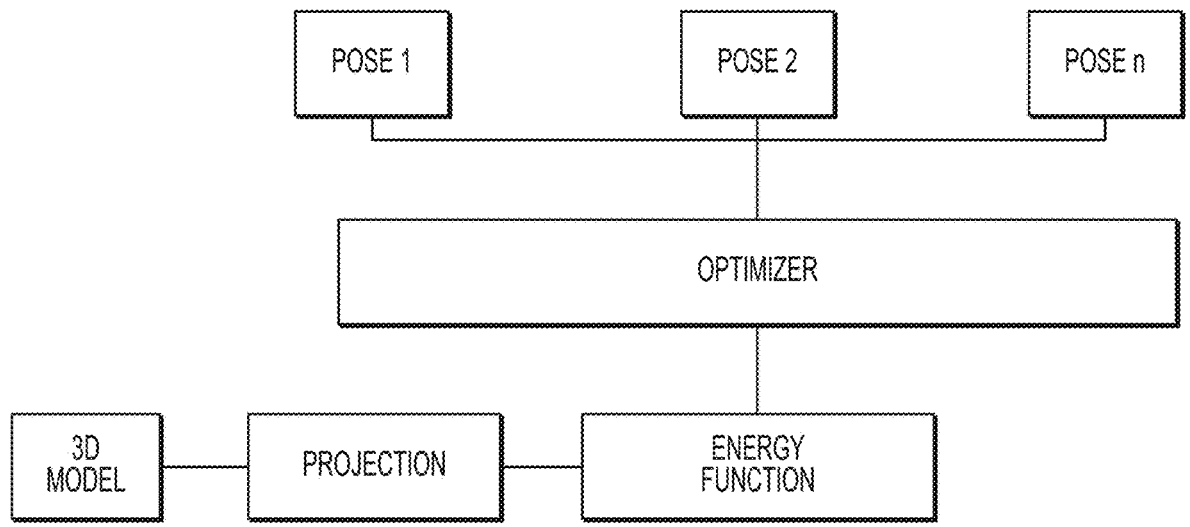
FIG. 24 is an exemplary process flow diagram depicting two dimensional to three dimensional registration in accordance with the instant disclosure.

In 3D-to-2D registration, the objective is to align a 3D surface to each frame of a monoplane fluoroscopic sequence or X-Ray image set (see FIG. 24). The 3D model is the surface mesh model for patient anatomy generated from preoperative imaging. The pose of the 3D model for all the frames in the sequence may be determined by optimization of an energy function. The energy function may consist of an edge score term, an intensity score term, a mis-alignment term, and a collision detection term. The edge score term and intensity score term show how well the projections of the 3D model fit to the fluoroscopic image with respect to edges and intensity, respectively. The mis-alignment term and collision detection term penalize misalignment and collision between neighboring bones in the same frame. Other factors may be introduced to the energy function to utilize a priori information, such as relative pose of multiple anatomies (pelvis and femur for example), known hardware or any other factors relevant to fitting optimization.

Figure 25A:
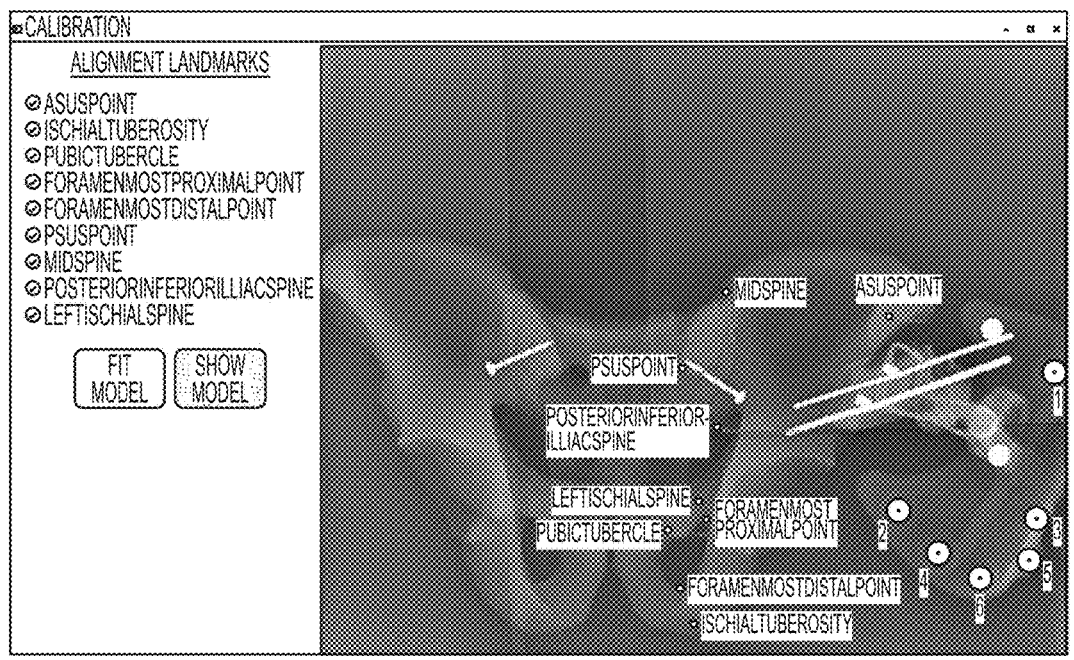
FIG. 25A is a screen shot of an exemplary software user interface for registration of a three dimensional model to a two dimensional X-Ray or fluoroscopic image, where the user selects a set of landmarks on the image that correspond to anatomical landmarks, in accordance with the instant disclosure.
Figure 25B:
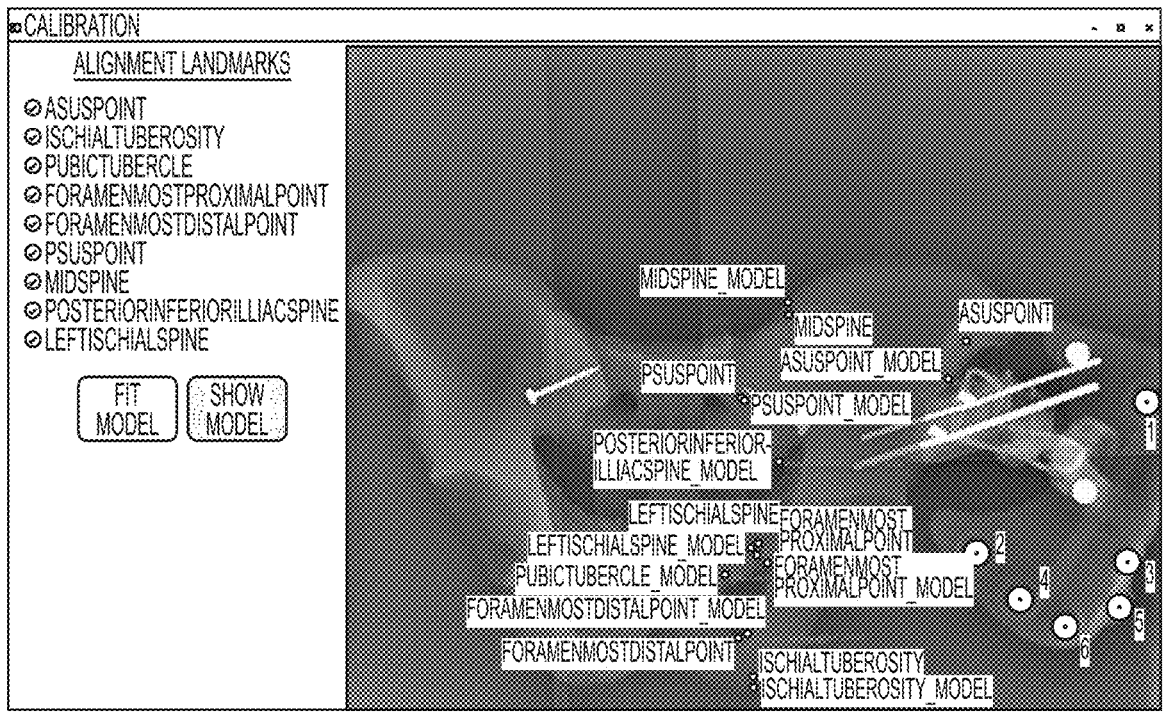
FIG. 25B is a screen shot of an exemplary software user interface for registration of a three-dimensional model to a two dimensional X-Ray or fluoroscopic image, where the landmarks are used in a first pass optimization which outputs the pose that results in the smallest distance between projected landmarks and selected landmarks, in accordance with the instant disclosure.
Figure 25C:
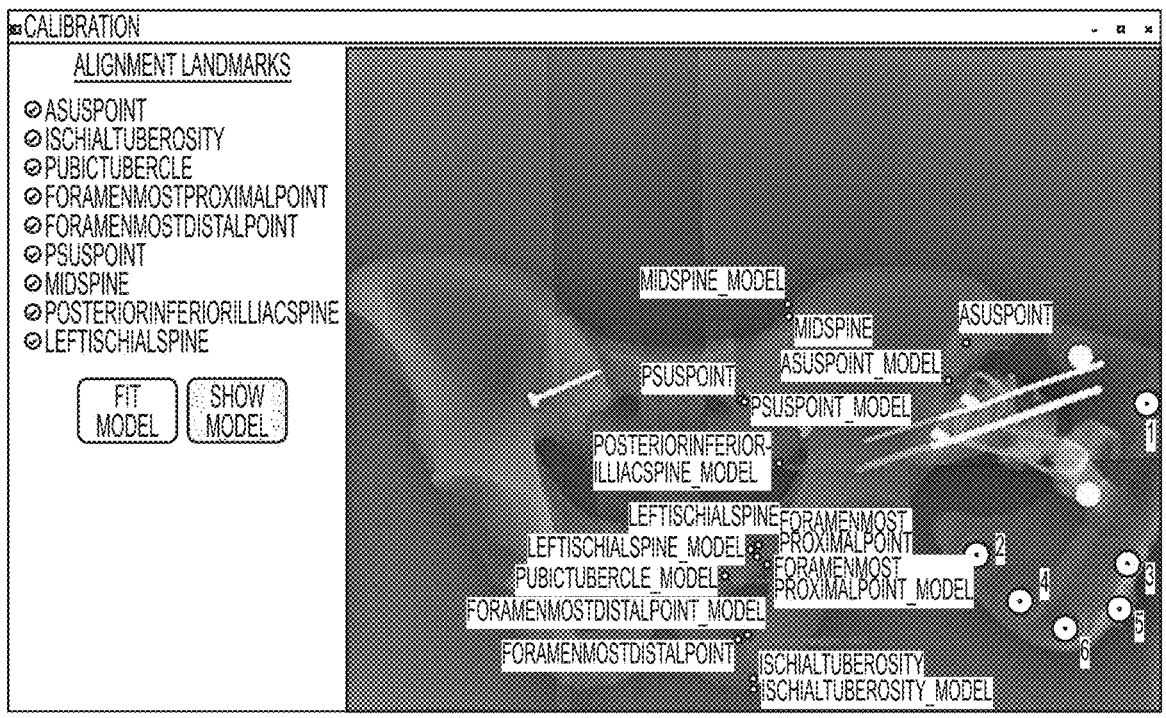
FIG. 25C is a screen shot of an exemplary software user interface for registration of a three-dimensional model to a two-dimensional X-Ray or fluoroscopic image, where further optimization (initialized at the output pose of the landmark optimization, that minimizes a cost function based on a projected image of the 3D model and the 2D image) results in a final pose of the three-dimensional model to the two dimensional image.
Figure 27:
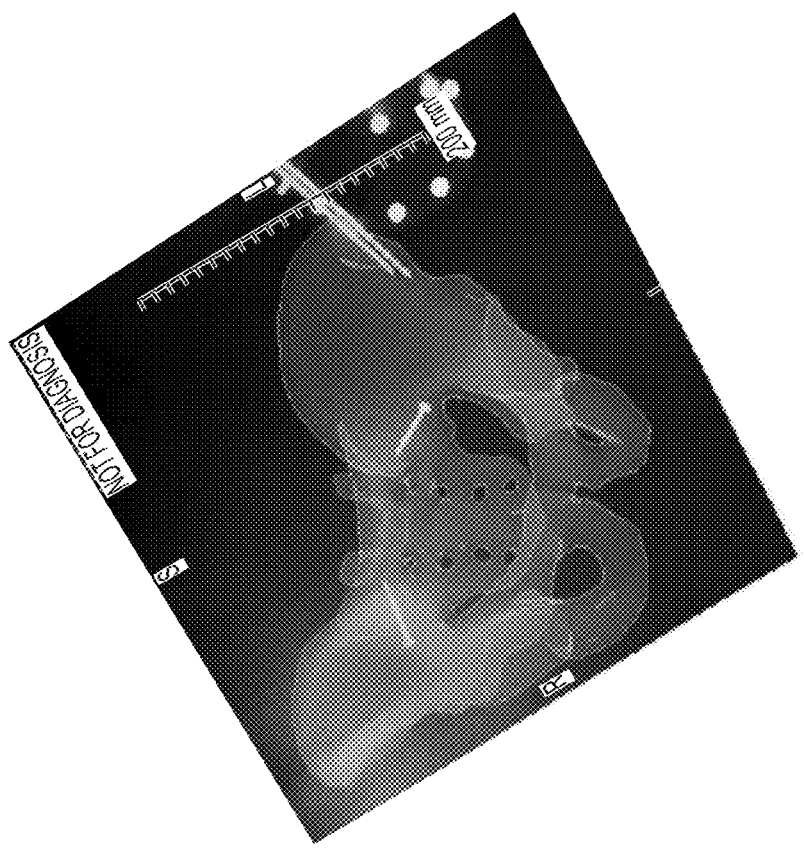
FIG. 27 is a three-dimensional bone model registered to the image of FIG. 26 in accordance with the instant disclosure.
Figure 26:
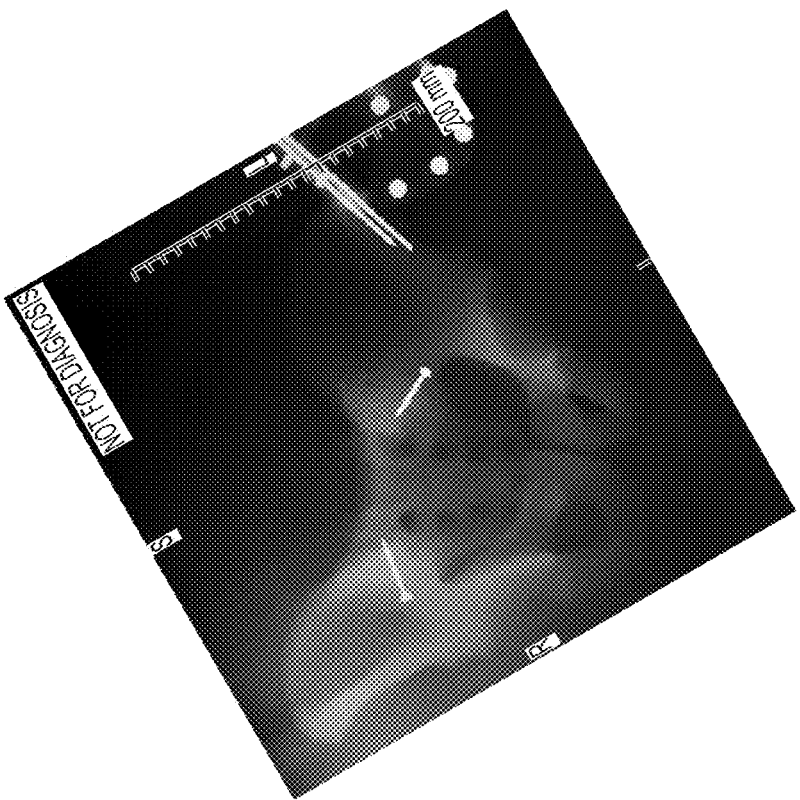
FIG. 26 is an exemplary radiography image of a hip/pelvis.

The registration process may run on software (e.g., a program) that prompts the user for input. For example, the software may require the user to identify landmarks on the image that correspond to landmarks on the 3D surface of the bone or implant. These correspondences may be used for an initial alignment of the model to the 2D image by optimizing the pose of the 3D model to minimize a cost function of the distance of the projected points to the selected points. The pose may be any or all of translation in x, y, z or rotations around the x-, y- and z-axes. The software may optionally also optimize to find the focal length of the camera (or other image taker) if it is unknown. This initial guess may then be used as an input into a refinement optimization step that may further update the pose to minimize an image based scoring function, which may use some metric between an image generated by projection of the 3D model onto the image plane and the original fluoroscopy or X-ray image. The metric may be derived directly from image information—edges, textures, intensities. The output of this optimization is the final pose of the 3D model that reflects the pose of the bone that optimally aligns the projection of the bone with the image data. Alternatively, the second optimization step may be run until a sufficiently satisfactory pose is found. The methods of 3D-to-2D registration are applicable to both pre-op reconstruction and intraoperative navigation (see FIGS. 25, 26). Several constraints may be placed if multiple objects are being registered to the same image. For example, the acetabular component will only be placed inside (or very near) to the acetabulum of the pelvis. This information may be used to constrain the allowed pose of the acetabulum during registration to the image. This technique is applicable whenever objects may have some known relative position. Further examples include femur to pelvis, femoral stem to femur.

IV Intraoperative Imaging

An intraoperative procedure may begin with preparing the patient for intra-operative imaging. The imaging system may produce radiographic images such as X-ray or fluoroscopy.

Figure 28:
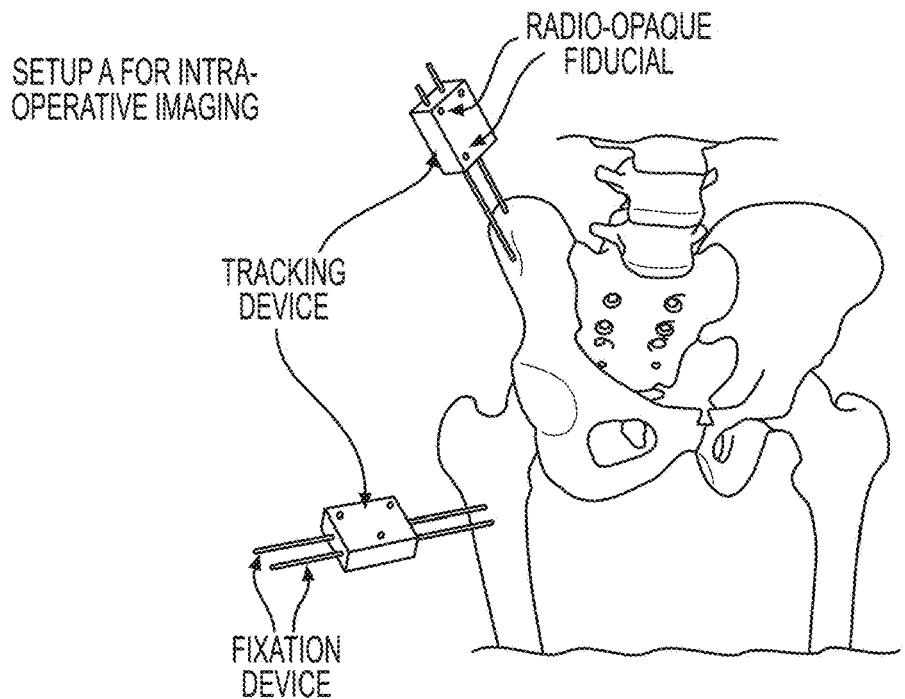
FIG. 28 is an exemplary depiction of setup A for intraoperative imaging where each bone of the joint (hip joint in this case) is attached to a tracking device via a fixation device, where each tracking device may include four or more radio-opaque features attached or embedded therein.

As part of a first exemplary process (setup A, see FIG. 28), the pelvis and/or femur of the patient may be attached with a fixation device (for example, bone pins), and a tracking device/sensor (e.g., an IMU) may be secured on to the fixation devices. By way of example, the fixation device may comprise a base attachment and an extension connector connecting the tracking device to the base attachment. The base attachment may be attached to a patient bone (e.g., pelvis). The extension connector may be removed after the registration to allow more room for a surgeon to operate.

It should be obvious to those who skilled in the art of sensor fusion and data processing that the positions and/or orientation of the device can be determined from the sensors' outputs using a Bayesian estimation algorithm. In exemplary form, a direct Kalman filter can be used to predict the positions and/or orientations based on sensors' outputs. See US20170296115, which is incorporated herein by reference. In further exemplary form, an error state Kalman filter can be used to predict the sensors' outputs error based on estimated orientations. It can be used to filter out erroneous or corrupted sensor data (e.g. vibration induced drift) that can potentially produce the wrong result.

A further alternate exemplary estimation technique may use an event based PID estimation technique that lowers the reliance of the sensor when a corrupted signal is detected. (e.g., prolong magnetic distortion).

The software is able to choose the outputs based on the conditions of the sensors to produce the best result.

The tracking device may be wired or wireless for data communication with a computing device having the software running thereon. By way of example, the tracking device may consist of a single or a combination of radio-opaque features for radio-imaging.

The radio-opaque features, which may be embedded in the tracking sensors or as standalone objects, may be arranged in any combination. By way of further example, the radio-opaque features may include at least four in number and be arranged so that at least one of the features is not in the same plane as the other features.

Figure 29:
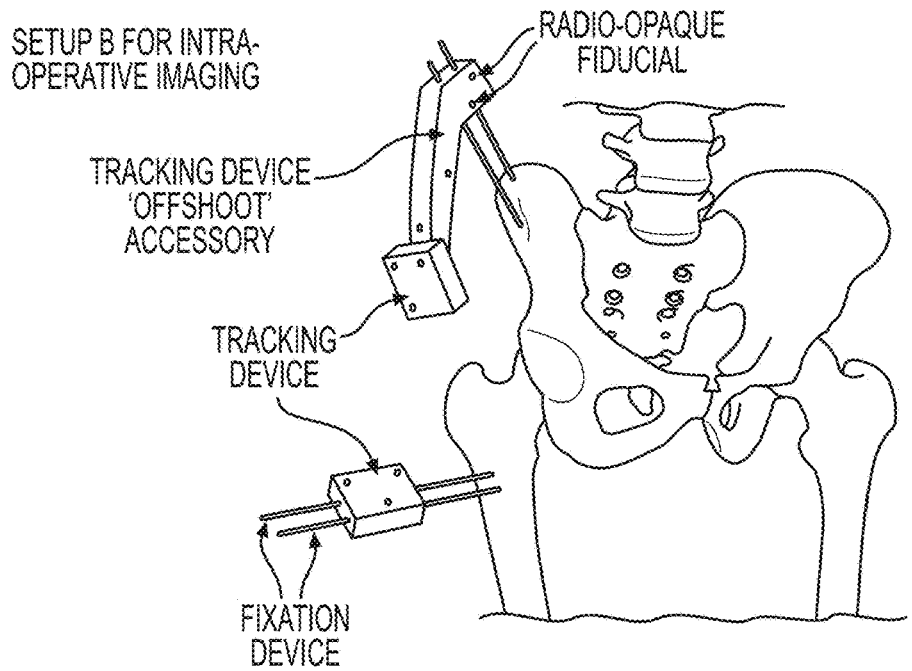
FIG. 29 is an exemplary depiction of setup B for intraoperative imaging where each bone of the joint (hip joint in this case) is attached to a tracking device via a fixation device (in this case, bone pins) and an additional tracking device accessory may be attached between the tracking device and the fixation device, where the accessory and tracking device each have four or more radio-opaque features attached or embedded therein.

As part of a second exemplary process (setup B, see FIG. 29), an accessory may be used to extend the tracking device/sensor (e.g., an IMU) from the fixation device. Because of the limited viewing area of the radiographic imaging system, the accessory may include additional radio-opaque features to aid the registration, and allow positioning of the tracking device to ensure that there are enough radio-opaque features available for registration. The accessory may have radio-opaque features embedded therein to aid the registration process.

Figure 30:
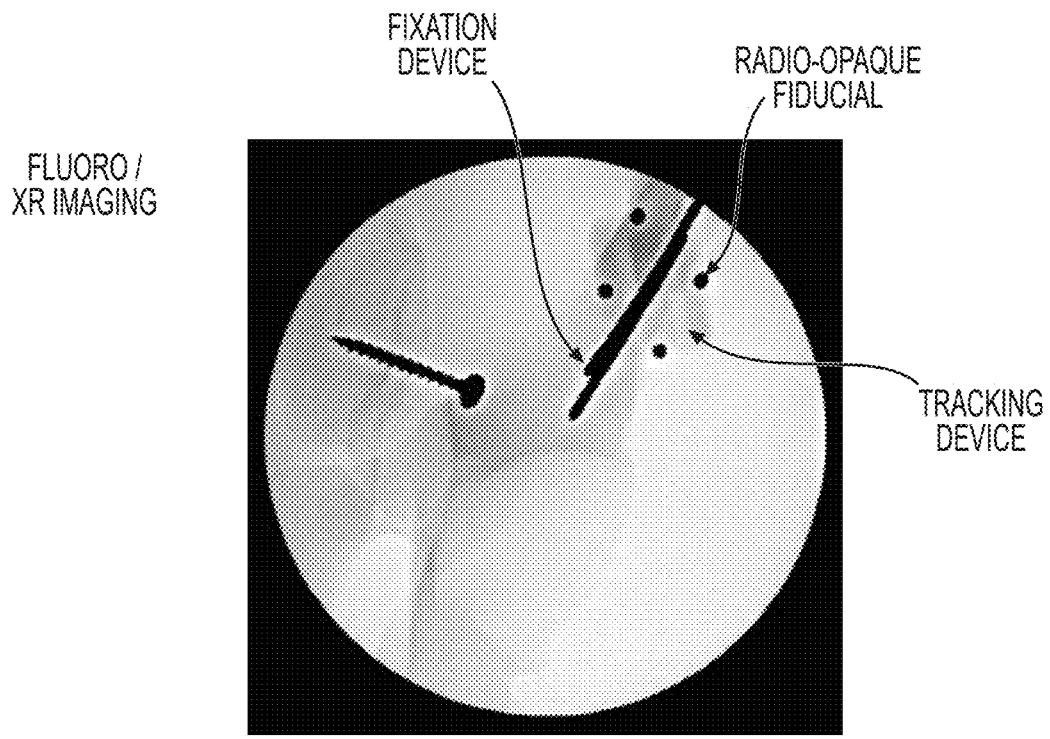
FIG. 30 is an exemplary radiographic image (e.g., fluoroscopy) showing a pelvis, a tracking device, a fixation device, and four radio-opaque features embedded into the tracking device.
Figure 31:
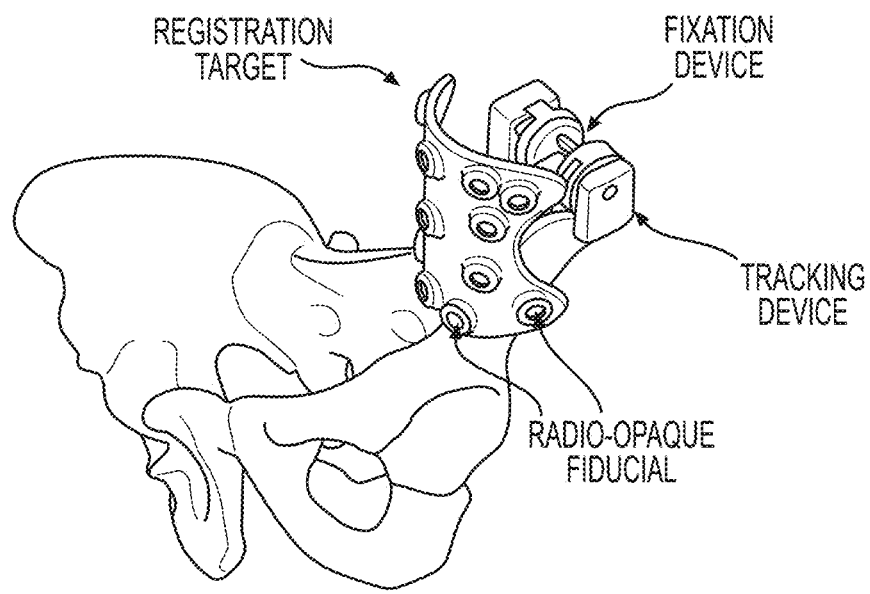
FIG. 31 is an exemplary mounting showing a tracking device/sensor, a fixation device (reference assembly), and a registration/image target with multiple radio-opaque features embedded therein being secured to a patient pelvis, in accordance with the instant disclosure.
Figure 32B:
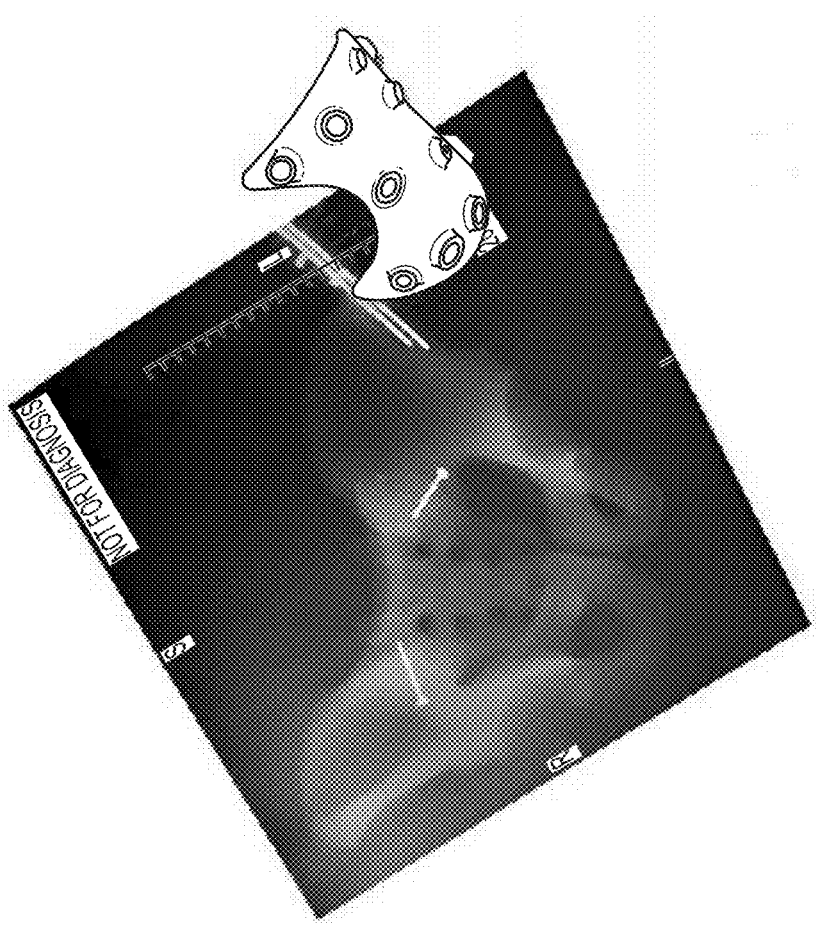
FIG. 32 shows exemplary X-ray images taken with (A) an image target mounted to a pelvis and (B) showing a virtual model of the image target superimposed onto the X-ray image, in accordance with the instant disclosure.
Figure 32A:
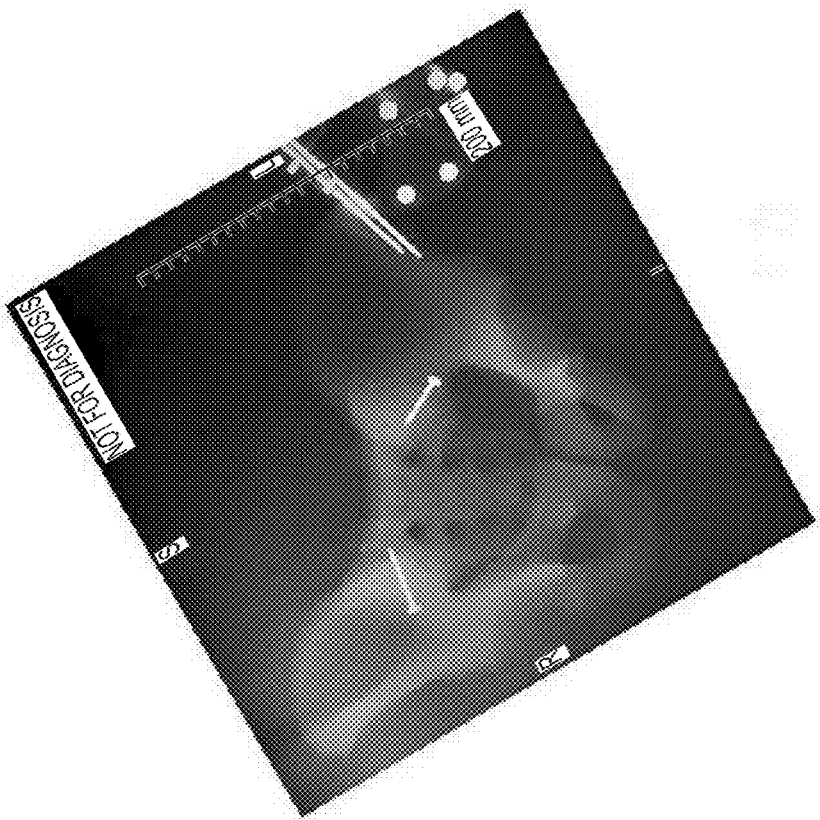
Figure 33A:
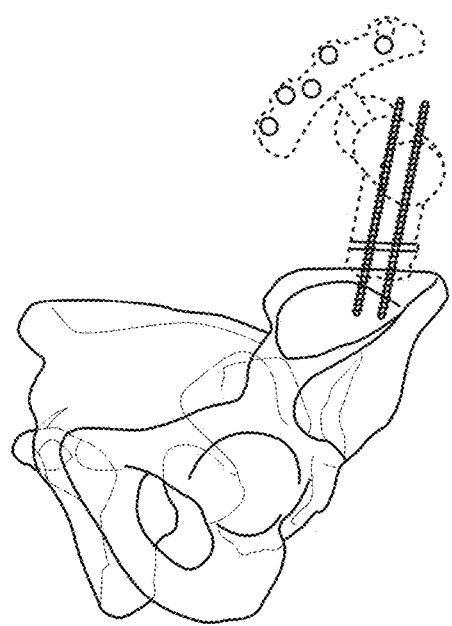
FIG. 33 shows (a) an imaging target, for registration of the tracking device/sensor, rigidly attached to the anatomy by way of an X-ray image, and (b) shows a 3D virtual model of the anatomy and the tracking device/sensor mounted thereto that matches the X-ray image.
Figure 33B:
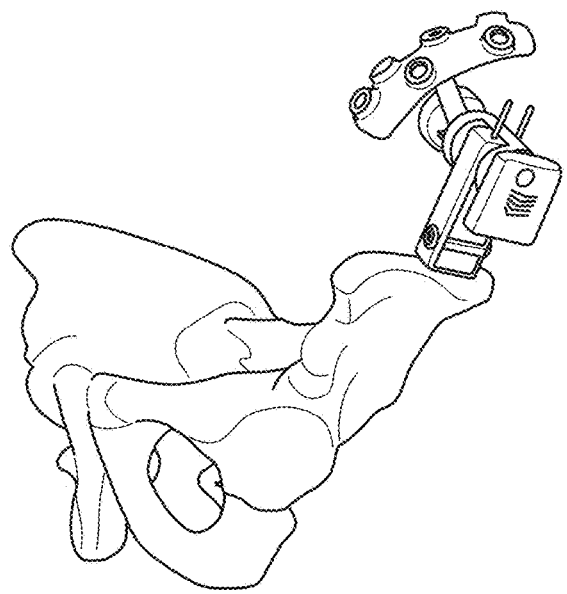

By way of further example, as depicted in FIG. 30, the accessory may be embedded with radio-opaque features that may be needed for intraoperative registration. By way of further example, in such a circumstance where the accessory has radio-opaque features, the accessory may be used alone for intraoperative imaging and registration. The tracking device may be attached to the accessory after the imaging is performed. The accessory may be operative to reduce electromagnetic interference from the radiographic imaging system to the tracking device.

As part of either exemplary process, multiple radiographic images may be taken. For example, one image where the pelvis and the radio-opaque features of the pelvis tracking device are in the viewing area of the radiographic imaging system and a second image where the femur and the radio-opaque features of the femoral tracking devices are in the viewing area of the radiographic imaging system. These images can then be used for registration.

After setting up the tracking device, a radiograph may be performed via a radiographic imaging system.

The image data may be transferred to a surgical guidance software via sending this image data wired or wirelessly through a network, or by using a physical transfer via external storage device. The image data may be processed by an imaging processing software, which may correct for distortions of the images.

V. Intraoperative Data Transfer

Intraoperative images may be transferred to an exemplary system disclosed herein, running the reconstruction and registration software, from an imaging device using different methods including, but not limited to: wireless (Blue tooth or Wi-Fi device), transfer through picture archiving and communication system (PACS), wired, or remote transfer via portable device such as a secured USB storage device.

VI. Intraoperative Registration

The orientations of a tracking device/sensor (e.g., an IMU) used in accordance with the instant disclosure may be recovered/discerned from radiography images using a registration target (i.e., an image target) associated with the tracking device that may include radio-opaque features. The configuration of radio-opaque features on the registration target may be known to a surgical guidance software, as described herein, which allows the software to compute the 3D orientations of the registration target from only the fiducial markers when radiography images are analyzed by the software.

The orientation of the tracking device/sensor may also be determined by the sensors on the tracking device itself. The orientation produced from the sensors may be in a different coordinate system than the orientation calculated from the radiography image(s). The transformation between the two orientations in potentially different coordinate systems may be computed so that the orientation determined by the tracking device can be transformed to the radiography image coordinate system and space, and vice versa.

A. Image Target for Registration of Navigation System

Figure 34:
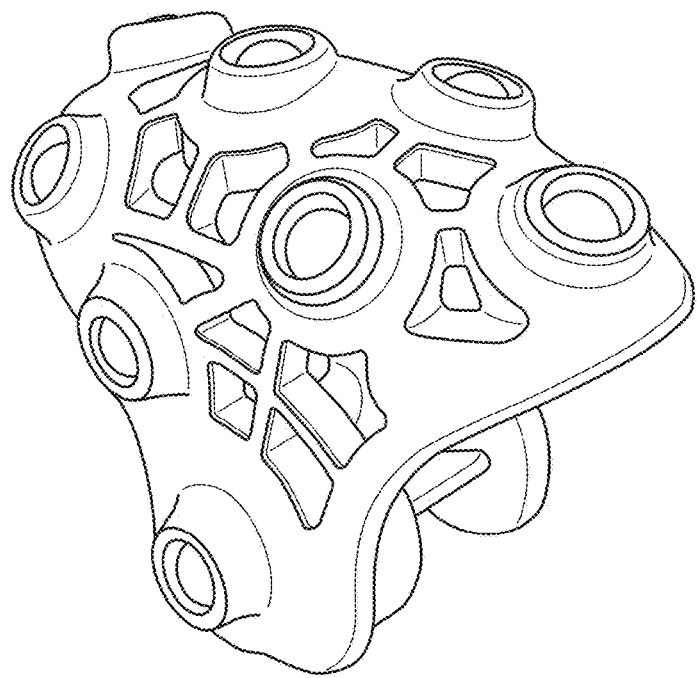
FIG. 34 depicts an exemplary image target in accordance with the instant disclosure.

An exemplary image target in accordance with the instant disclosure may be dimensioned so that the sizing is appropriate to be visible in all expected imaging views without being overly cumbersome (see FIG. 34). This dimensioning may be the result of one or more analyses performed on a representative population, in addition to simulated X-ray and fluoroscopic images, for the bodily region of interest such as, without limitation, any of the joints of a potential patient body.

Figure 35:
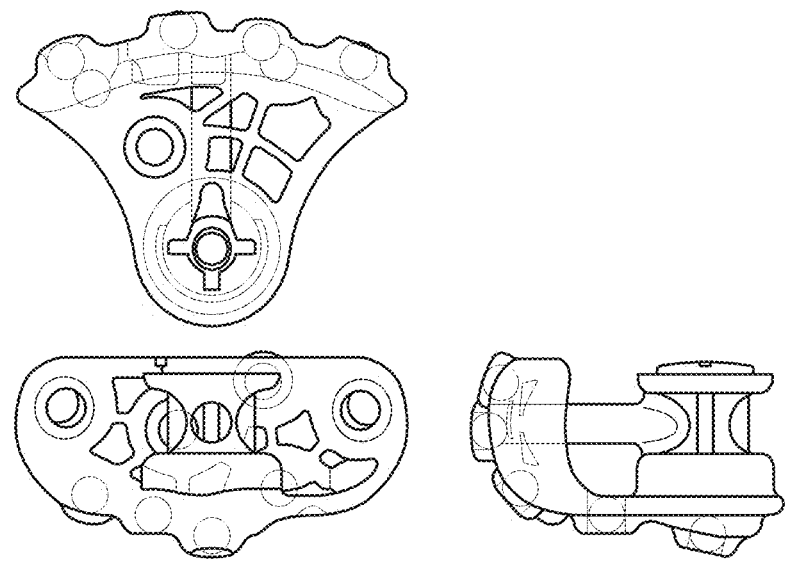
FIG. 35 depicts multiple views of the image target of FIG. 34.

An exemplary image target in accordance with the instant disclosure may include one or more beads, that may be embedded within a radiotransparent or radiotranslucent material, that may have a known shape and size. By way of example, a known size may comprise a sphere having a 9.4 mm diameter. The beads may be arranged in an asymmetric pattern along a non-planar surface so that the precise configuration of the beads is known to facilitate identification and registration of the image target in the acquired radiography images. The image target may comprise a bead jig, to hold and retain the beads, and may allow for rotation (e.g., between zero and 180 degrees) with respect to a tracking device, thereby allowing the beads to fit in predetermined image frames. The number of beads may vary, but preferably at least four beads are utilized that do not all lie within the same plane of once mounted to the bead jig. A greater number of beads may provide for greater redundancy, for example 5-20 beads. FIG. 35 shows an exemplary bead jig that includes an asymmetrical design pattern in accordance with the instant disclosure when viewed from different orthogonal perspectives. The asymmetric design helps reduce the chance that the beads will overlap with one another across differing views of the radiographic images taken while the bead jig is within the field of view.

Figure 36:
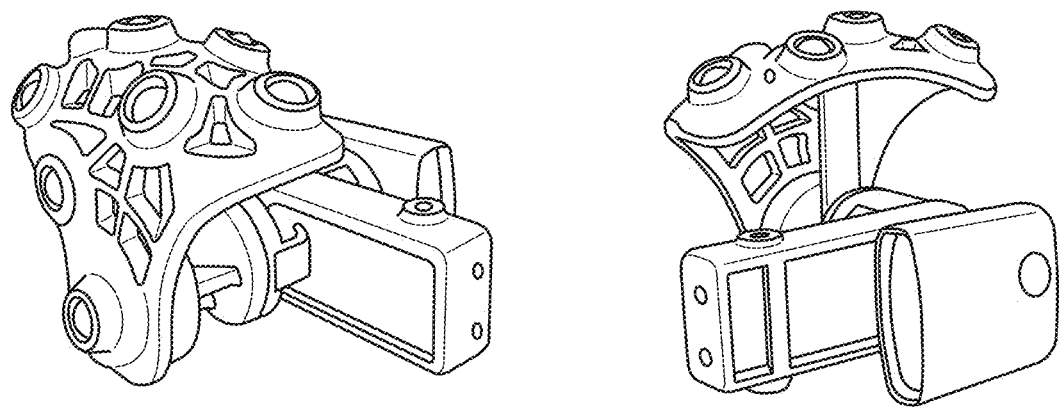
FIG. 36 depicts multiple views of an exemplary reference assembly comprising the image target of FIG. 34 mounted to a reference piece and a tracking device/sensor.
Figure 37:
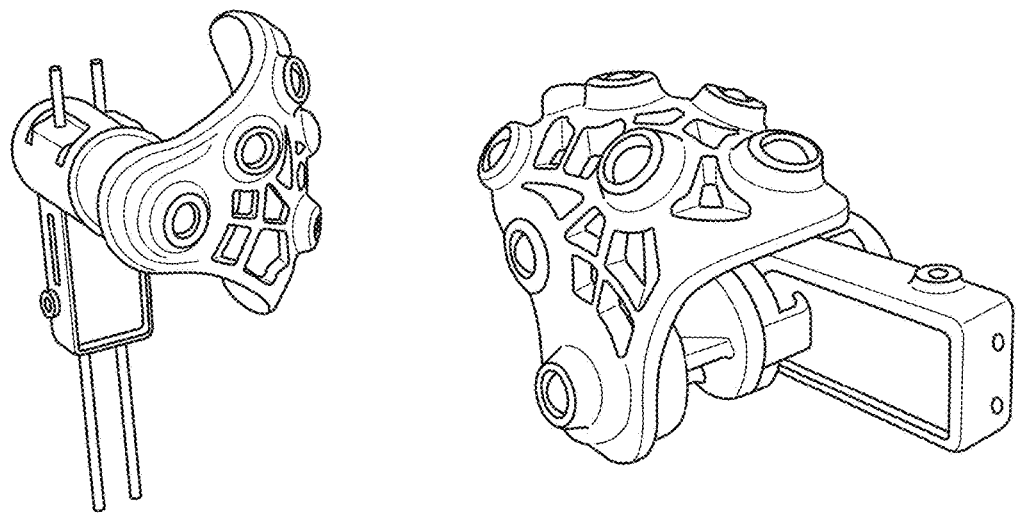
FIG. 37 depicts the exemplary reference assembly of FIG. 36 with and without bone pins mounted thereto.

The exemplary image target may be used with or without a tracking device/sensor (e.g., and IMU). The exemplary image target may include at least one locking feature, which allows locking of the image target with a tracking device/sensor, by way of a reference piece, as seen in FIG. 36. The reference piece may include at least two locking features, one which is intended to be used with the image target and one with the tracking device/sensor. The assembly of the image target, reference piece, and tracking device/sensor places the sensor in a known orientation and position relative to the image target. Therefore, when the image target 3D model is registered to the beads visible in the captured radiographic image(s), the tracking device/sensor position and orientation relative to the registered 3D image target can be determined by knowing the assembly design. FIG. 36 shows examples of the image target, tracking device/sensor, and reference assembly. Both the image target and tracking device/sensor are locked to the reference piece in a known orientation and known position.

Figure 38:
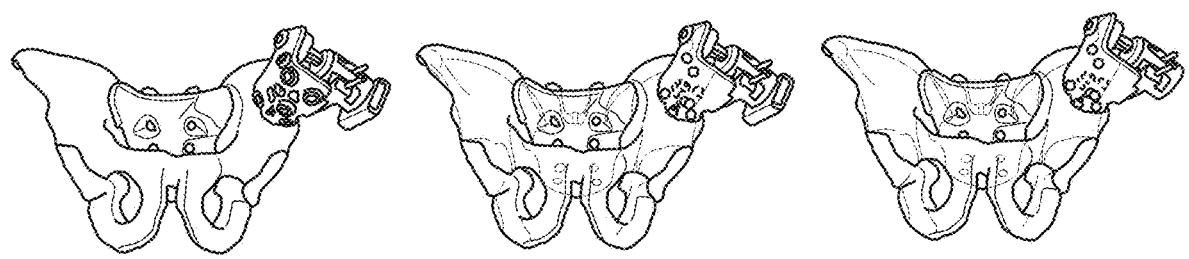
FIG. 38 depicts the exemplary reference assembly of FIG. 36 mounted to a virtual model of a pelvis (left) and mounted to an actual pelvis via an X-ray image (right) in an anterior-posterior view.
Figure 39:
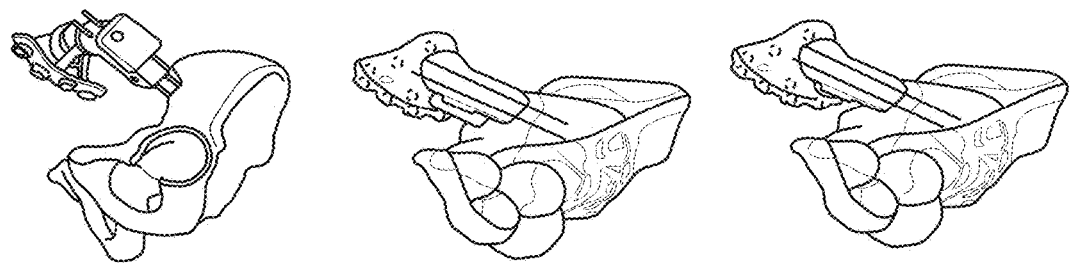
FIG. 39 depicts the exemplary reference assembly of FIG. 36 mounted to a virtual model of a pelvis (left) and mounted to an actual pelvis via an X-ray image (right) in a Judet view.
Figure 40:
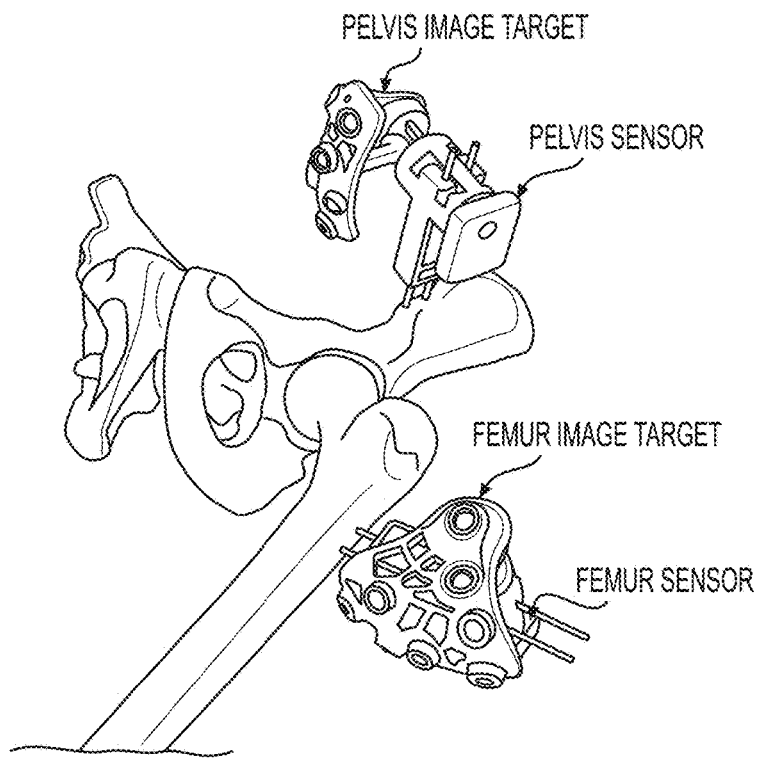
FIG. 40 is an exemplary virtual 3D joint model of the hip showing multiple exemplary reference assemblies of FIG. 36 mounted respectively to both the pelvis and femur that may allow 3D-2D registration and sensor navigation in accordance with the instant disclosure.
Figure 41:
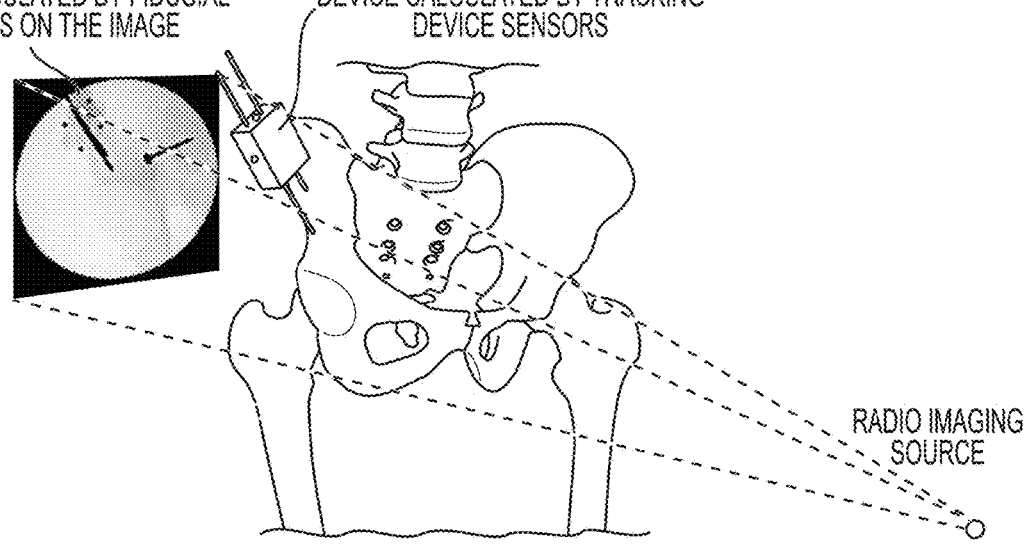
FIG. 41 is an exemplary depiction showing that the system establishes a relationship between the real world coordinate of the tracking device $q_0$ and the image coordinate by way of the image target using the fiducial markers in the radiographic images $q_1$.

FIGS. 38 and 39 show two different views in AP and Judet with the image target, reference piece, and tracking device/sensor in position in respective radiographic images and the result of using these radiographic images to construct and register corresponding 3D virtual models. The assembly (e.g., image target, reference piece, and tracking device/sensor) may be mounted to a patient bone in a rigid manner. This mounting may be performed percutaneously or using intra-incision fixation. The reference piece may be designed to facilitate this fixation. In an alternate exemplary embodiment of a reference piece, this may entail having at least two holes designed to allow surgical pins to pass therethrough, with the pins being configured to lock to the reference piece using conventional methods, such as, without limitation, utilization of set screws or similar devices. Because it may be desirable to guide the placement of certain femoral components during a reconstructive surgical procedure, the assembly may also be rigidly fixed to the femur, as shown in FIG. 40. It should be understood that, in view of the foregoing disclosure, one skilled in the art will understand that the exemplary assembly or any components thereof may be mounted to one or more bones of a patient and potentially utilized to register and/or create 3D virtual models of a patient's bone(s) as part of a surgical procedure and, optionally, as part of a surgical navigation system to be used during a surgical procedure.

B. Tracking Device to Patient Anatomy Registration

Figure 42B:
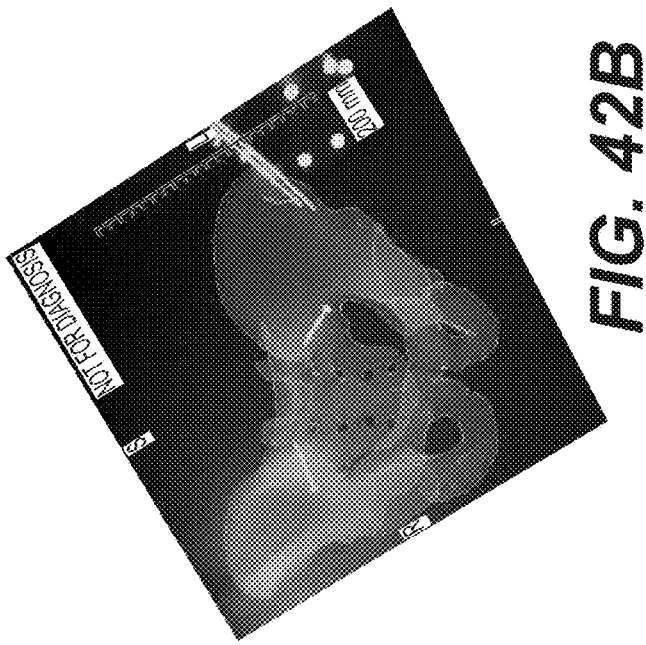
FIG. 42 illustrates an exemplary graphical view of a registration process in accordance with the instant disclosure.
Figure 42C:
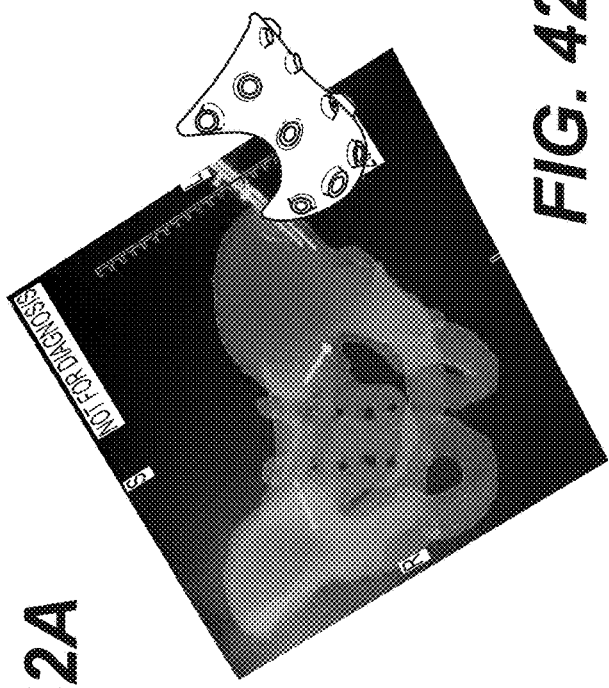
Figure 42A:
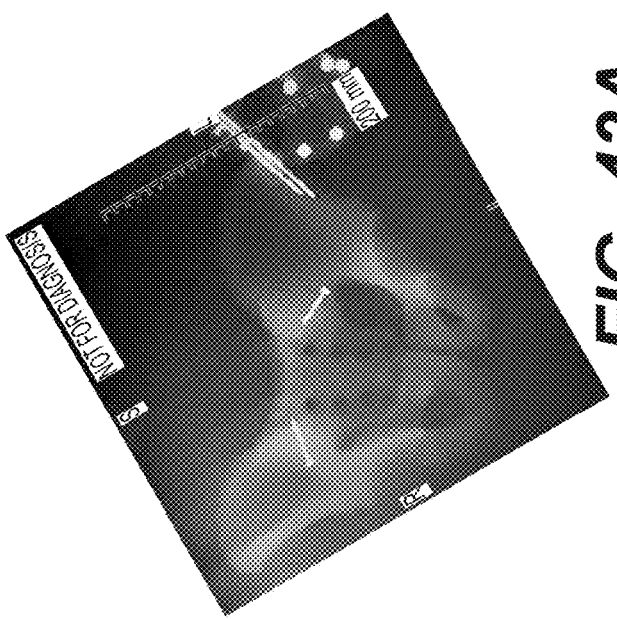

The orientations of the tracking device/sensor (e.g., and IMU) and the patient anatomy may both be transformed to the radiographic image space and registered together. This process may entail a first 3D-to-2D registration step for registering the patient anatomy to the image plane. Then a second 3D-to-2D registration step for aligning the reference assembly (image target, reference piece, and tracking device/sensor). Once the registration is completed, the relative location and orientation of the tracking device to the anatomy becomes known. At this point, the tracking device may be used to track the patient's bone segment. This step is outlined in FIGS. 42 and 43.

In an exemplary process of performing registration of the patient for a total hip arthroplasty procedure, one tracking device may be connected to the pelvis of the patient via the fixation device, while another tracking device may be connected to the femur of the patient via another fixation device. The radiographic images may then be taken for both bone segments (i.e., the femur and pelvis for hip arthroplasty) along with the radio-opaque features of each image target. As referenced in FIG. 42, the assembly is mounted to a patient bone and a radiography image is taken (A). The position and orientation of the patient's bone is recovered through the registration process described previously (B). The position and orientation of the global frame, provided by the image target, is recovered. The offset between the position and orientation of the patient's bone and the position and orientation of the image target are calculated, and the patient's bone is tied to the image target (C). The tracking device attached to the image target reports its current orientations at the same time that the image is taken. The offset between the tracking device and the image target are calculated so that the orientation of the tracking device is now in the global frame. Since both the tracking device and the anatomy are tied together by the image target in the global frame, the orientations of the patient bone can be registered to the tracking device, and the tracking device can be used to track orientation changes on the patient's bone. In this fashion, the image data may be transferred to a surgical guidance computer to perform registration. Once the registration is completed, the image target may be removed from the fixation device or assembly.

Figure 43:
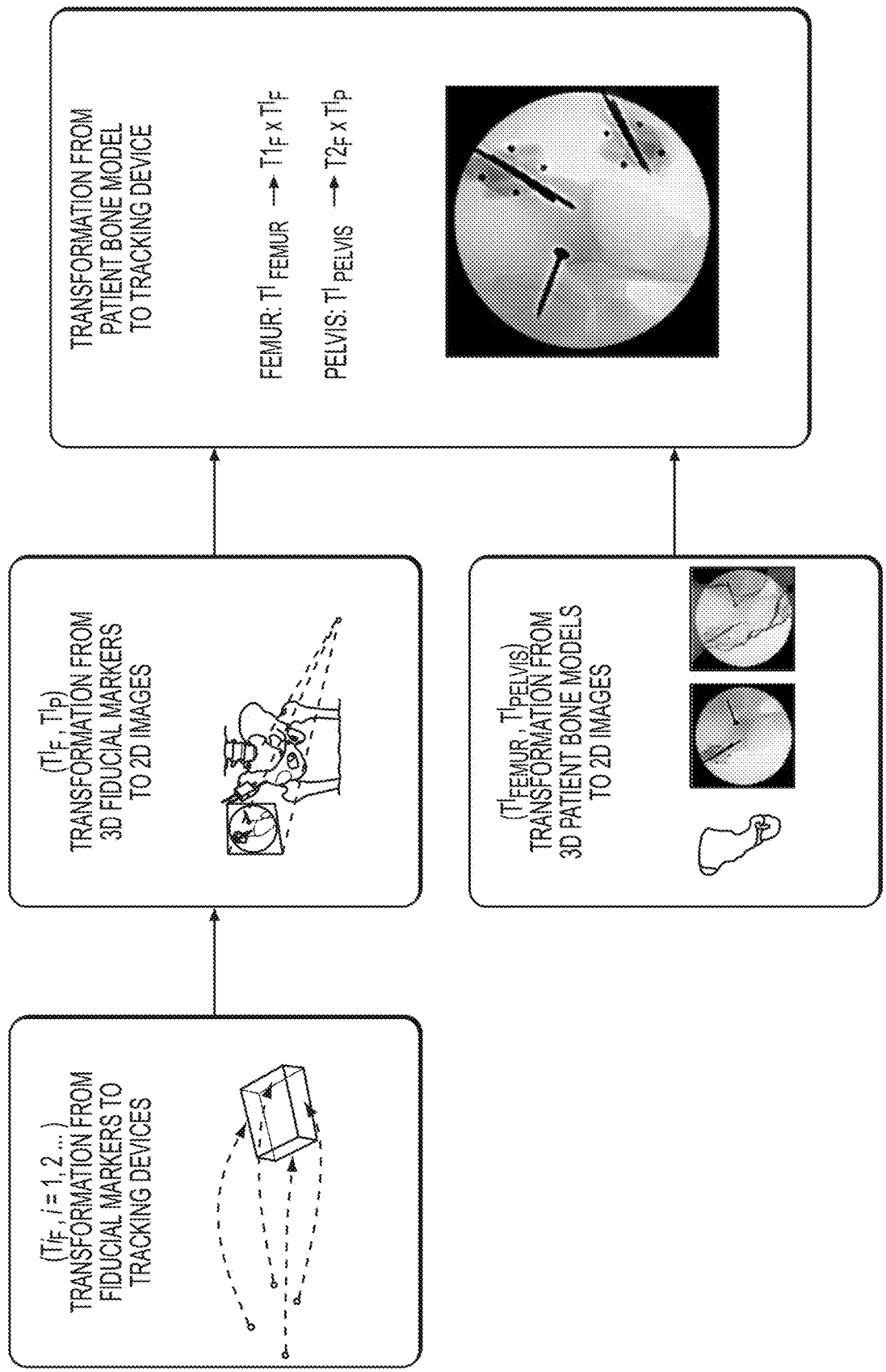
FIG. 43 illustrates an exemplary process flow for carrying out an exemplary registration process in accordance with the instant disclosure.
Figure 44A:
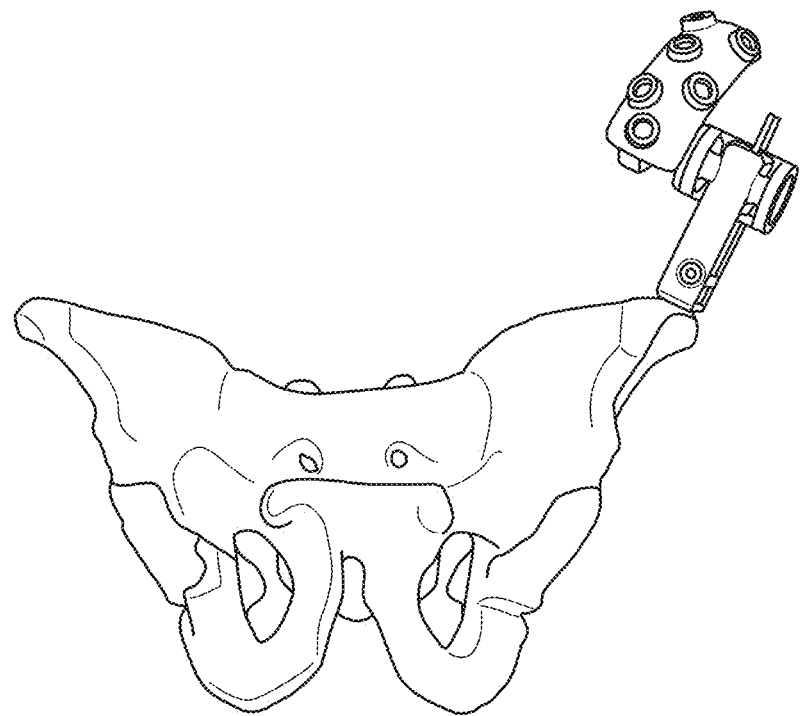
FIG. 44A illustrates a PAM reference assembly mounted to a patient anatomy in a predetermined position and orientation that may be used to register image and model data, as well as facilitate real-time surgical navigation.
Figure 44B:
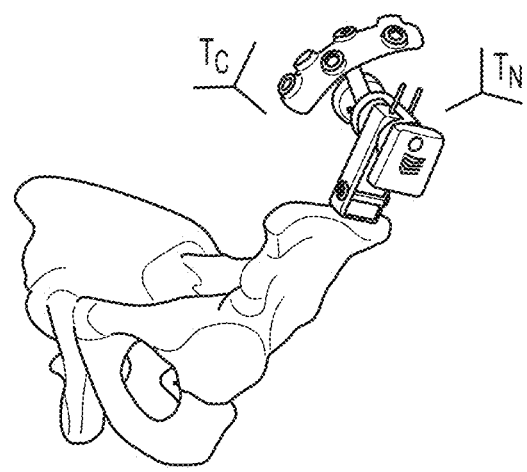
FIG. 44 B illustrates an exemplary calibration matrix between a real-time navigation system coordinate (TN) system and a calibration target coordinate system (TC).
Figure 45:
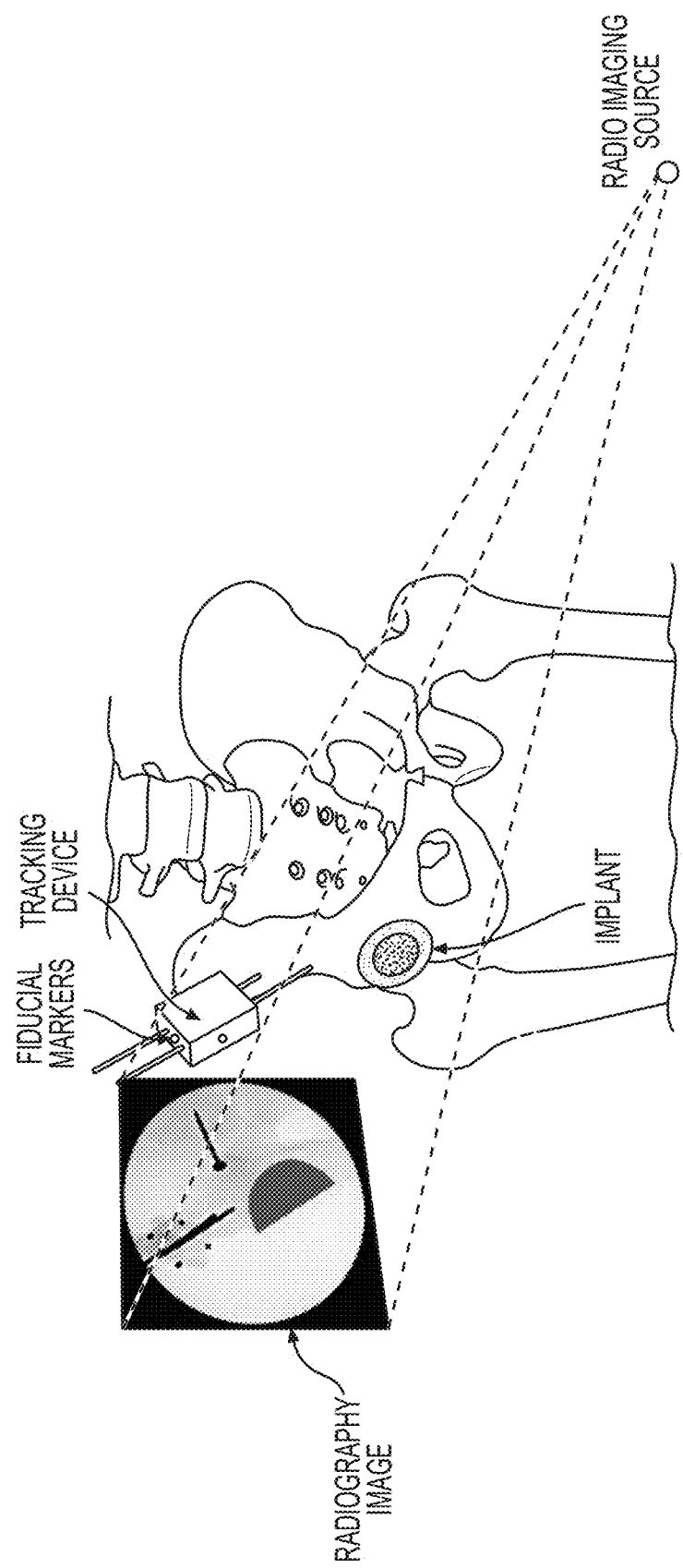
FIG. 45 is a graphical depiction of a radiographic imaging system that may be used a surgical procedure to verify the placement position of an implant in accordance with the instant disclosure.
Figure 46:
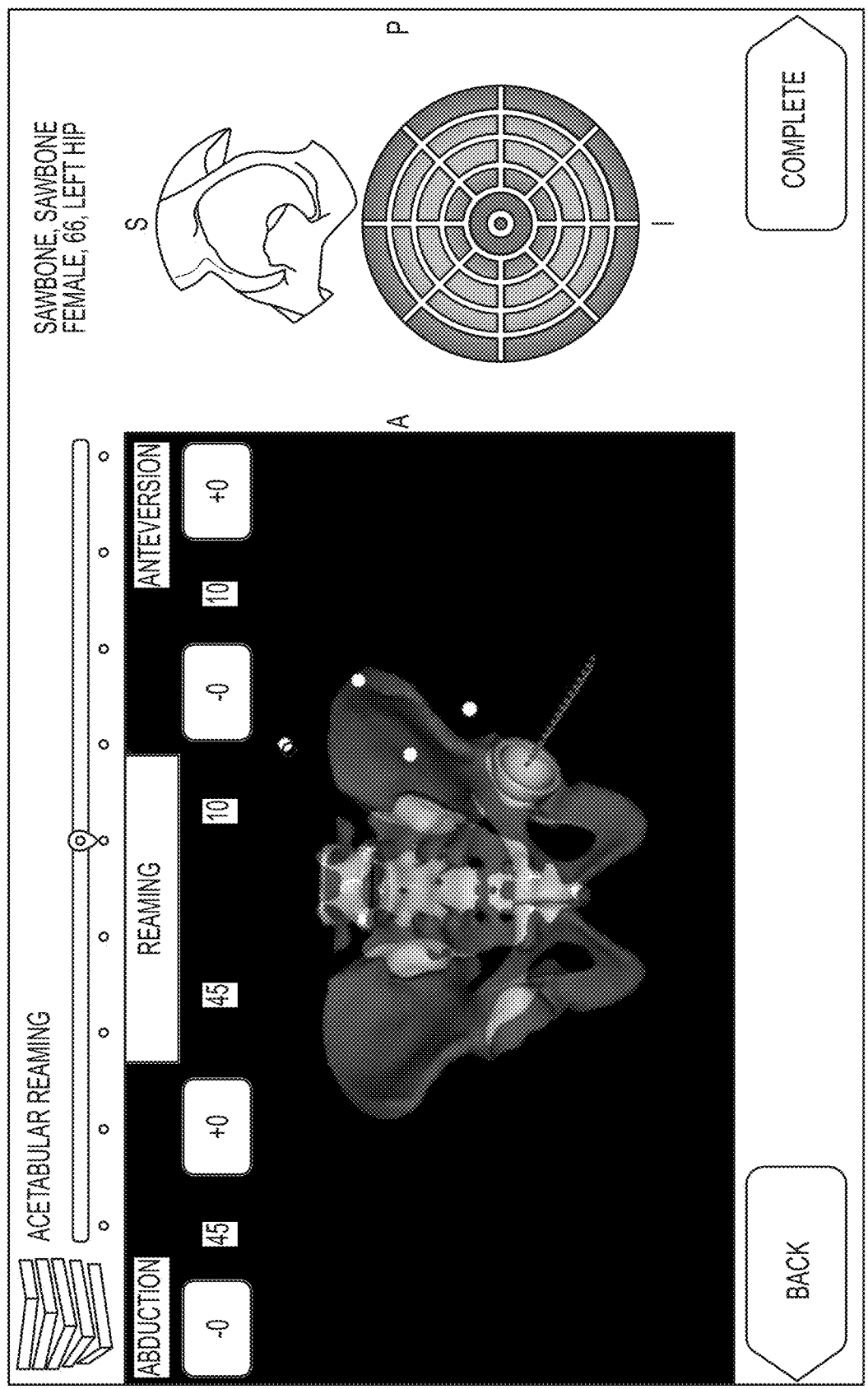
FIG. 46 is a screen shot of an exemplary surgical guidance display in accordance with the instant disclosure, which depicts a 3D virtual model of patient anatomy (in this case the hip) and the intended orientation a surgeon should follow to place the acetabular cup implant consistent with a preoperative plan, where deviations from the intended orientation are shown in a bullseye illustration to bring any deviation back to the intended orientation.
Figure 47:
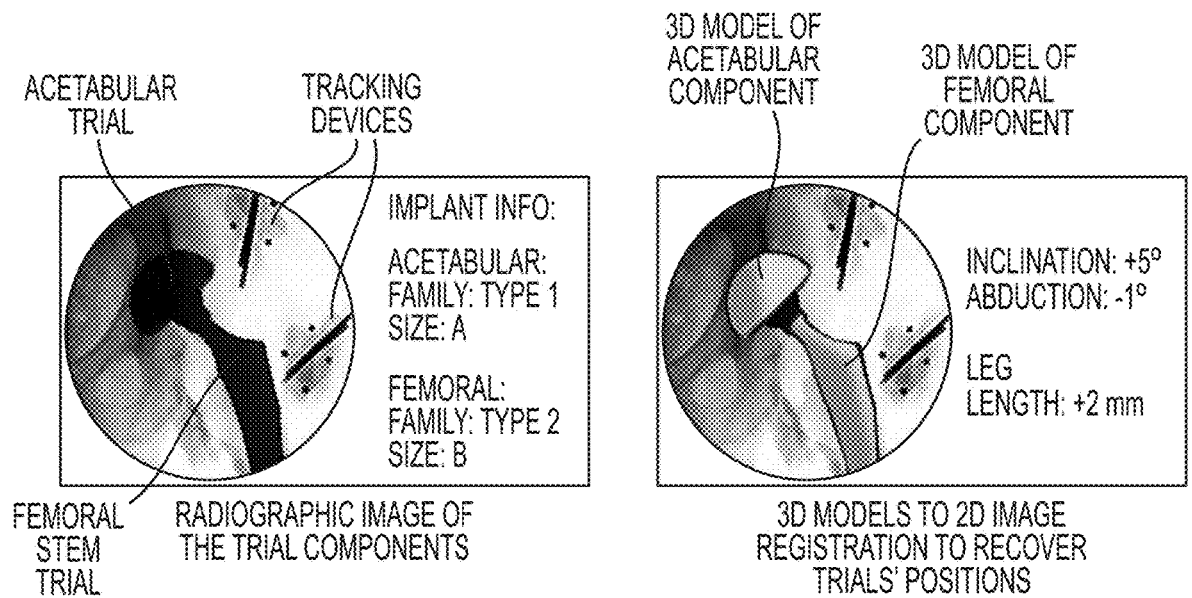
FIG. 47 is a depiction showing that since implant information is known to the surgical guidance software, it can use the 3D CAD model of the same implants to perform 3D models to 2D image registration, so that once 3D-to-2D image registration is completed, orientation metrics such as combined anteversion and abduction angles can be determined based on the relative orientation difference of the 3D to 2D models.
Figure 48:
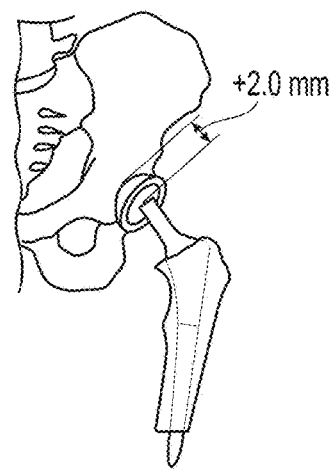
FIG. 48 is a graphical depiction reflecting that the spatial measurement such as leg length may be measured from the registered 3D models to obtain 3D measurements as compare to direct 2D measurement on the radiographic image, which may eliminate ambiguity of the clinical measurements from a 2D planar image.

Referring to FIG. 43, the relationship between the tracking device and the radio-opaque features of the image target are known to the system. The radio-opaque features may be embedded or attached to a secondary device attaching to the tracking device. The transformation from the fiducial marker locations to the orientation of the tracking device is defined as $T_{iF}$, i=1, 2 . . . . The transformation from the 3D locations of the radio-opaque features to the 2D radiography image is defined as $T_{IF}$ for the radio-opaque features on the femur and $T_{IP}$ for the radio-opaque features on the pelvis. The transformation to determine the orientation of the tracking device 1 attached to the femur based on the 2D radiography image is given as $T_{1F} \times T_{IF}$, and the orientation of the tracking device 2 attached to the pelvis based on the 2D radiography image is given as $T_{2F} \times T_{IP}$. The transformation from the 3D patient bone models to the 2D radiography image are defined as $T_{IFemur}$ for the femur and $T_{IPelvis}$ for the pelvis. With these transformations, the orientation of the patient bones can be registered to the tracking devices attached to them.

Femur: $T^i_{Femur} \rightarrow T1_F \times T^i_F$

Tibia: $T^i_{Pelvis} \rightarrow T2_F \times T^i_P$

C. Patient Anatomical Mapper (PAM)

In accordance with the instant disclosure, an exemplary patient anatomical mapper (PAM) comprises patient specific instrumentation that is manufactured to fit in one specific orientation and position on the patient's anatomy. The geometry of the PAM may be created from a virtual 3D model of the patient's bone, which is created from previously obtained imaging, such as pre-operative imaging. The PAM may include one or more locking features designed to facilitate attachment of a tracking device/sensor or a reference piece for holding a tracking device/sensor. A further locking feature of the PAM is patient-specific and designed to mate in a unique position and orientation with the patient anatomy (such as against a patient bone). When matching the patient-specific locking feature to the correct site/location of the patient anatomy, the orientation and position/location of the attached tracking device/sensor should be known relative to the anatomy.

The PAM may be embedded with radio-opaque features similar to the image target discussed herein, so that upon placing the PAM on the patient anatomy in the intended position and orientation, the position and orientation of the PAM relative to the image target may be known. This offset may be used to verify leg length after the implant is placed.

VII. Surgical Guidance

In accordance with the instant disclosure, the foregoing tracking devices/sensors (e.g., IMUs) may be utilized as part of surgical guidance such as a total hip arthroplasty procedure. In exemplary form, surgeons can continue typical surgical procedures of a total hip arthroplasty such as making an incision, performing femoral head resection, and exposing the acetabular cup. The surgeon can attach one of the tracking devices to a pelvis fixation device (to attach to the pelvis), and another tracking device to the surgical instruments to be guided including, without limitation, a drill, a cup impactor, a rasp handle, a cutting guide, or any other instrument. The tracking devices may be configured to continuously send data indicative of orientation and/or translation to the processing device (e.g., computer, specialized machine, tablet, etc.) running the surgical navigation software. The relative orientation between the tracking devices may be represented as inclination/declination, and abduction/adduction angles or any other values that may be desirable and be displayed on a display such as, without limitation, a computer monitor or surgical navigation display. The surgeon may use the tracking devices to know orientations of one or more surgical instruments for such exemplary procedures as acetabular resurfacing, acetabular cup impacting during trial placement, and acetabular cup impacting during actual placement of the final orthopedic implant, and verifying the orientation of the acetabular cup on the patient anatomy.

The surgeon may also use the tracking devices for femoral stem placement, which may include attaching one or more tracking devices to a femur fixation device (to attach to the femur), and another tracking device attached to the surgical instrument. The surgical navigation system may use data from the tracking devices to determine and guide the orientations of broaching, where the surgical guidance may alert the surgeon in cases where the broaching orientation can cause femoral fracture. The surgeon may also use this surgical navigation system and tracking devices to place the femoral implant. The surgical guidance software may estimate the combined clinical inclination/declination, and abduction/adduction angles of the implant. A more detailed discussion follows.

By way of example, a first IMU comprising a tracking device/sensor, optionally having been previously mounted to an acetabular registration tool, may be mounted to a surgical tool in a known location. In exemplary form, the IMU may be fixed rigidly to a cup reamer with a known orientation relative to the reaming direction so that the orientation of the cup reamer with respect to the pelvis is known and dynamically updated via multiple IMUs (e.g., 1st IMU mounted to the cup reamer and 2nd IMU mounted to pelvis).

The software program of the surgical navigation computer provides a graphical user interface (associated with the surgical navigation system) that may display virtual models of the patient's pelvis and a virtual model of the surgical tool in question, in this case a cup reamer (the virtual model of the patient's pelvis having already been completed pursuant to the virtual templating step, and the virtual model of the cup reamer or other surgical tool having been previously loaded into the system for the particular cup reamer and other surgical tools that may be utilized), and may update the orientation of the pelvis and surgical tool in real time via the display providing position and orientation information to the surgeon. Rather than using a display, the instant system may include surgical devices having indicator lights indicating to the surgeon whether the reamer is correctly oriented and, if not, what direction(s) the reamer needs to be repositioned to correctly orient the reamer consistent with the pre-operative planning After resurfacing using the cup reamer is complete, the IMU may be removed from the cup reamer and fixed rigidly to a cup inserter with a known orientation relative to the inserter direction. The cup inserter may then be utilized to place the cup implant, with the IMUs continuing to provide acceleration feedback that the software utilizes to calculate position to provide real time feedback as to the position of the pelvis with respect to the cup inserter. To the extent that holes are drilled into the pelvis before or after cup positioning, the IMU (optionally previously mounted to a registration tool) may be rigidly fixed to a surgical drill to ensure the correct orientation of the drill with respect to the pelvis. An optional analogous registration tool and set of IMUs may be used with the software system to assist with placement of the femoral stem component.

By way of example, a first IMU may be mounted to another surgical tool in a known location. In exemplary form, the IMU (optionally previously mounted to the femoral registration tool) may be fixed rigidly to a surgical saw in a known location so that movement of the IMU correspondingly translates into known movement of the surgical saw. Given a second IMU is fixedly mounted to the femur in a known location, the IMUs work together to provide dynamically updated information to the software system about changes in the position (via acceleration data) of both the femur and surgical saw.

The software program, as mentioned beforehand, provides a display allowing a surgeon to view virtual models of the patient's femur and of the surgical tool in question, in this case a surgical saw (the virtual model of the patient's femur having already been completed pursuant to the virtual templating step, and the virtual model of the surgical saw or other surgical tool having been previously loaded into the system for the particular surgical saw and other surgical tools that may be utilized), and is configured to update the orientation of the femur and surgical tool in real time via the display providing position and orientation information to the surgeon. Rather than using a display, the instant system may include surgical devices having indicator lights indicating to the surgeon whether the surgical saw is correctly oriented and, if not, what direction(s) the surgical saw needs to be repositioned to correctly orient the surgical saw to make the correct bone cuts consistent with the pre-operative planning. After making the requisite bone cuts, the first IMU may be removed from the surgical saw and fixed rigidly to a reamer (to correctly ream the intramedullary canal) and thereafter mounted to a femoral stem inserter with a known orientation relative to the inserter direction. The stem inserter may then be utilized to place the femoral stem implant within the reamed intramedullary canal, with the IMUs continuing to provide feedback that the software utilizes to calculate positions and orientations of the femur and stem inserter in real time and display the virtual models of the femur and stem inserter, relative to one another in real time, via the display so that the surgeon can visualize the relative position and orientation of the surgical instrument relative to patient anatomy without requiring a direct line of sight to the surgical site.

VIII. Intraoperative Placement Verification

During or after a final or trial component or components have been placed, radiographic images may be taken. The images may be used to detect trial orientation and position relative to anatomy via 3D-to-2D registration of the components and anatomy or landmarks to the image plane. There may be two configurations of this step depending on the surgical planning used. If no pre-operative reconstruction is available for the patient, a first step may be undertaken to calibrate the verification image with the previously acquired intraoperative images and to calculate the position of the patient 3D coordinate system relative to the verification image. This process may be identical to multi-view calibration and intraoperative landmarking as described in detail hereafter.

A. Using 3D Implants CAD Models

With knowledge of a current implant family and sizes, the 3D positions of the implants may be computed using 3D-to-2D image registration technique as discussed herein. By way of example, the 3D-to-2D image registration may be carried out as described in Applicant's Section III Anatomy Registration by using the implant geometries as the shapes to be registered. Additional metrics may be added to the scoring function to account for estimated position of the implants and implant constraints (e.g., constrain pose of the femoral stem relative to femoral anatomy and cup; constrain pose of cup relative to anatomy and femoral stem).

The 3D-to-2D image registration may be enhanced via inputs of the tracking devices, where the optimization algorithm may use the orientations from the tracking device to restrict and assist the position estimation. As the 3D positions of the implants are preferably known, any spatial measurement and metric such as leg length may be computed from the registered 3D models directly. By way of example, in case of a leg length mismatch, the surgical guidance system may provide an alternative implant family and sizes to adjust the leg length differences to more closely approximate one another.

B. Generic Template with No Implant CAD Models

Figure 49:
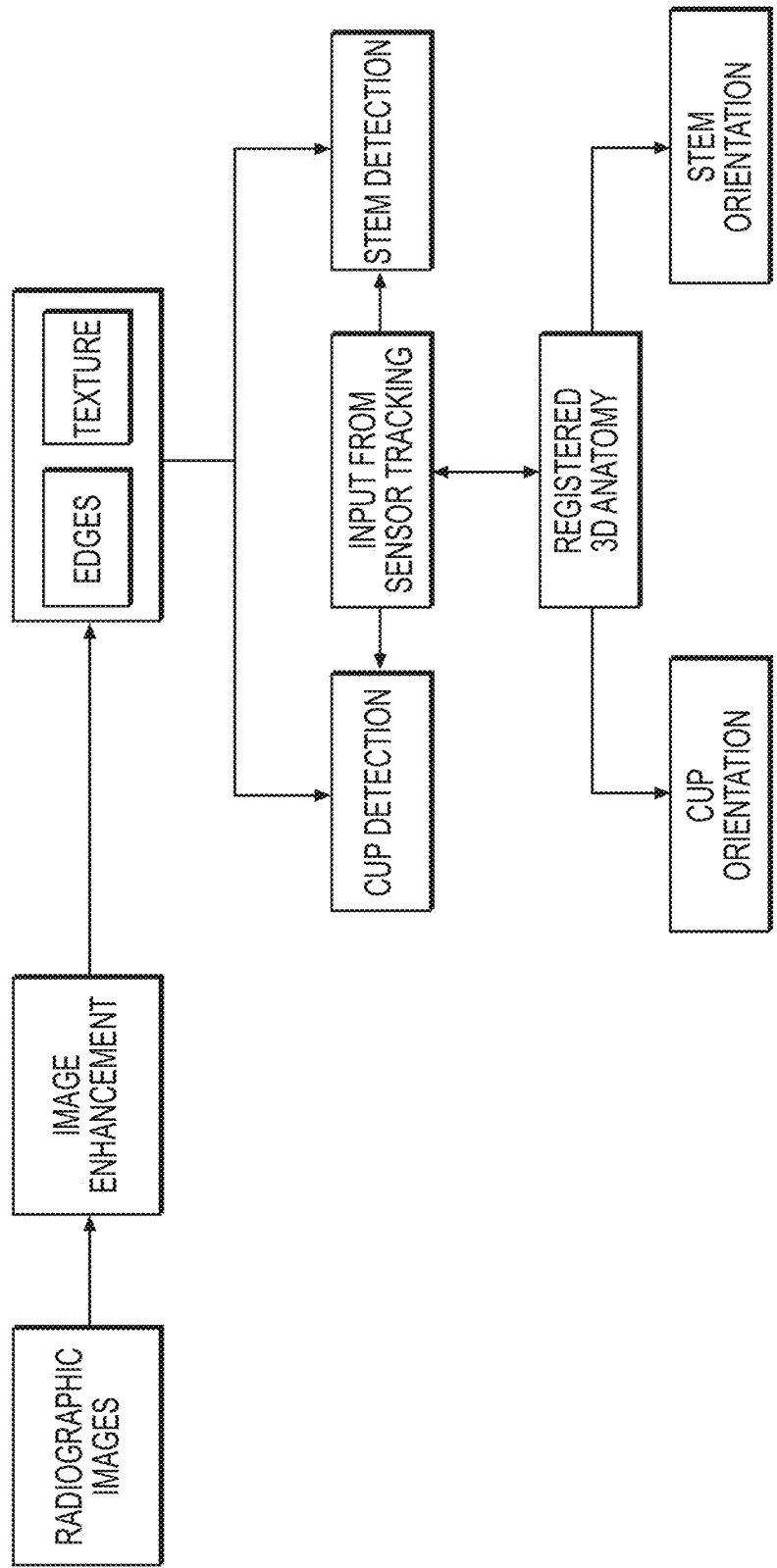
FIG. 49 is an exemplary flow diagram depicting a process of detecting cup and stem orientation without using an orthopedic implant CAD model.

As depicted in FIG. 49, implant orientation may be tracked and determined by the surgical navigation system without corresponding orthopedic implant CAD models. In exemplary form, radiographic images of the patient anatomy post orthopedic implant positioning may be taken. These images may be enhanced to allow software to automatically detect edges of objects depicted in the images, as well as differentiate between objects using texture within the images, to determine the relative position of objects within the images relative to one another. Likewise, data from the tracking devices may be concurrently utilized with object detection from the radiographic images to determine the relative position of the orthopedic implant (such as a femoral stem or an acetabular cup). This relative position data from the 2D images may then be registered to the 3D anatomical model via the 3D-to-2D image registration as described in Applicant's Section III Anatomy Registration. Post registration with the 3D model, the orthopedic implant orientation may be ascertained.

IX. Multi-Views Intraoperative Imaging

Multi-views intraoperative imaging may be required if no pre-operative imaging is captured, but a 3D coordinate system or anatomic model is desired to aid in component placement. Intraoperative images may be acquired to capture both patient anatomy and the image target (as discussed previously). A plurality of images may be acquired intraoperatively using convention imaging modalities including, without limitation, X-ray or fluoroscopy imaging. As an example, for a pelvis, a set of two or more images (AP, Judet RPO, Judet LPO) may be acquired, where the compilation of images preferably contains all necessary surgical landmarks for placement of an acetabular component. For a proximal femur anatomy, a set of two or more images (AP and lateral) may be acquired, where the compilation of image preferably contains all necessary surgical landmarks of both the proximal femur and intramedullary canal for placement of the femoral stem.

A. Multi-View Calibration

Figure 52:
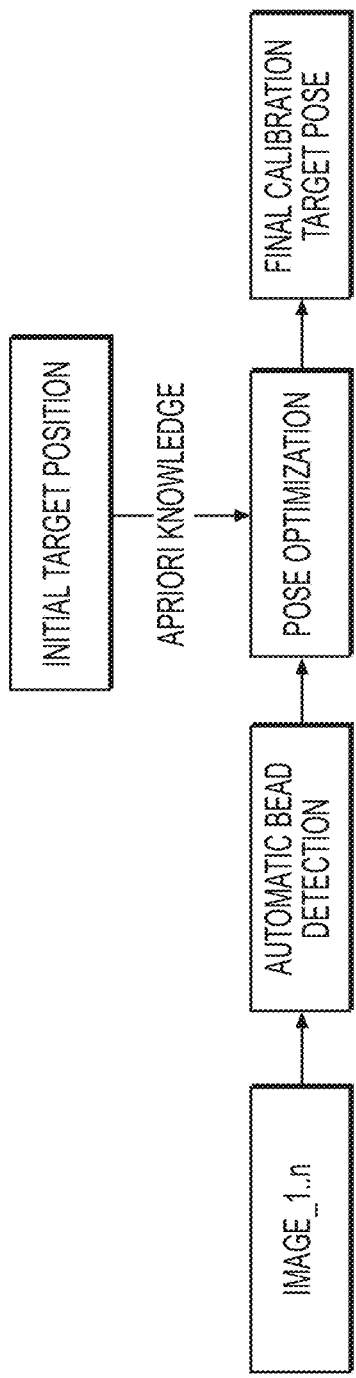
FIG. 52 is an exemplary flow diagram for automatic extraction of stereo calibration matrix in accordance with the instant disclosure.
Figure 53:
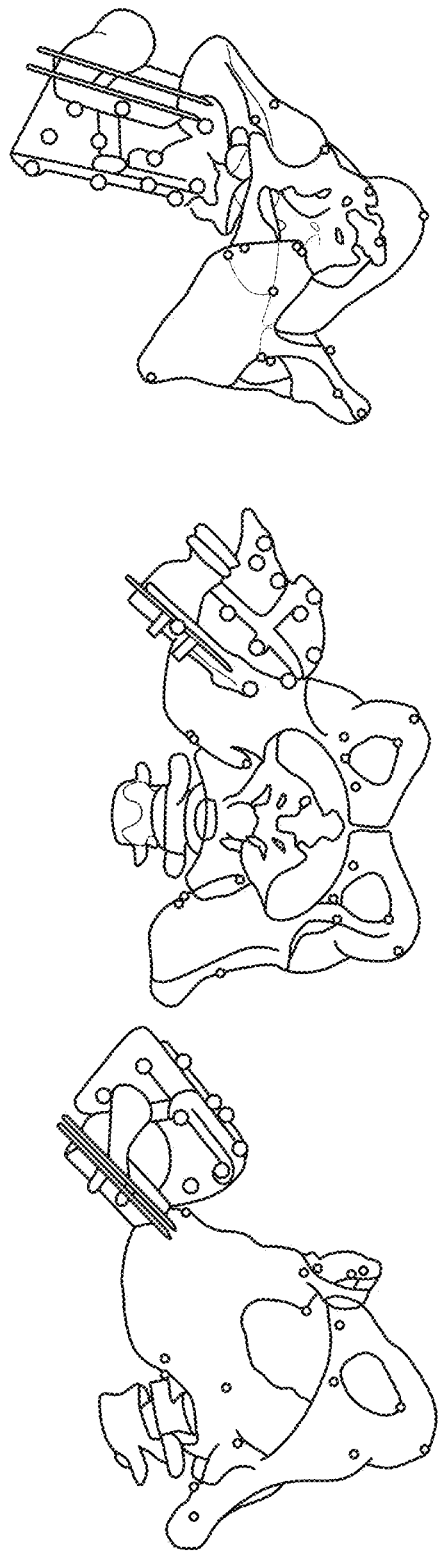
FIG. 53 is a series of radiographic images showing an initial product of a computer program automatically detecting radio-opaque beads visible in the radiographic images.
Figure 54:
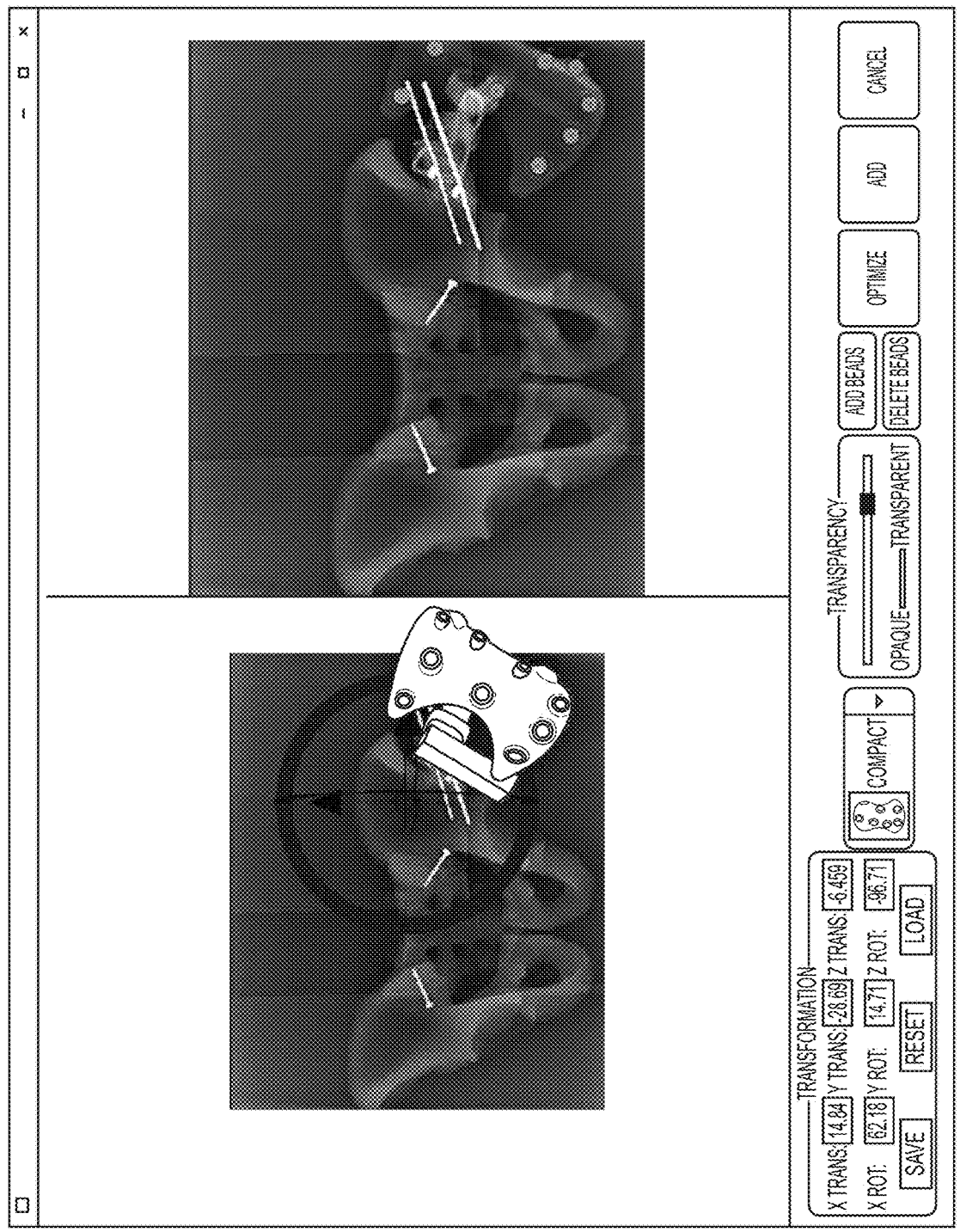
FIG. 54 is a screen shot from an exemplary computer program in accordance with the instant disclosure showing multiple radiographic images and the result of automatic pose estimation of the calibration target appearing in the images.

Multi-view calibration, in exemplary form and in accordance with the instant disclosure, may include a process of extracting image taking parameter to reconstruct a 3D scene from an "n" set of images. This information may then be utilized to reconstruct a set of 3D landmarks. An exemplary process of stereo camera calibration is outlined in FIG. 52. Input images may be enhanced and filtered, and an automatic target bead (i.e., radio-opaque target shapes) finding algorithm may then be utilized to find the locations of several or all of the calibration target beads visible in the image (see FIG. 53). Detected beads may then be used to calculate pixel spacing, followed by estimation of 3D target pose in space. This may be achieved by initializing position of the calibration target based on the view of the imager (e.g., an X-ray view) such as using a priori position that may be extracted from the location of calibration target relative to a standard imaging view. This initial pose may then be optimized to achieve the pose that achieves the bead configuration projected in the input image (see FIG. 54). An exemplary alternative to using a calibration target may include using corresponding points in each image.

X. Intraoperative Landmarking

Figure 55:
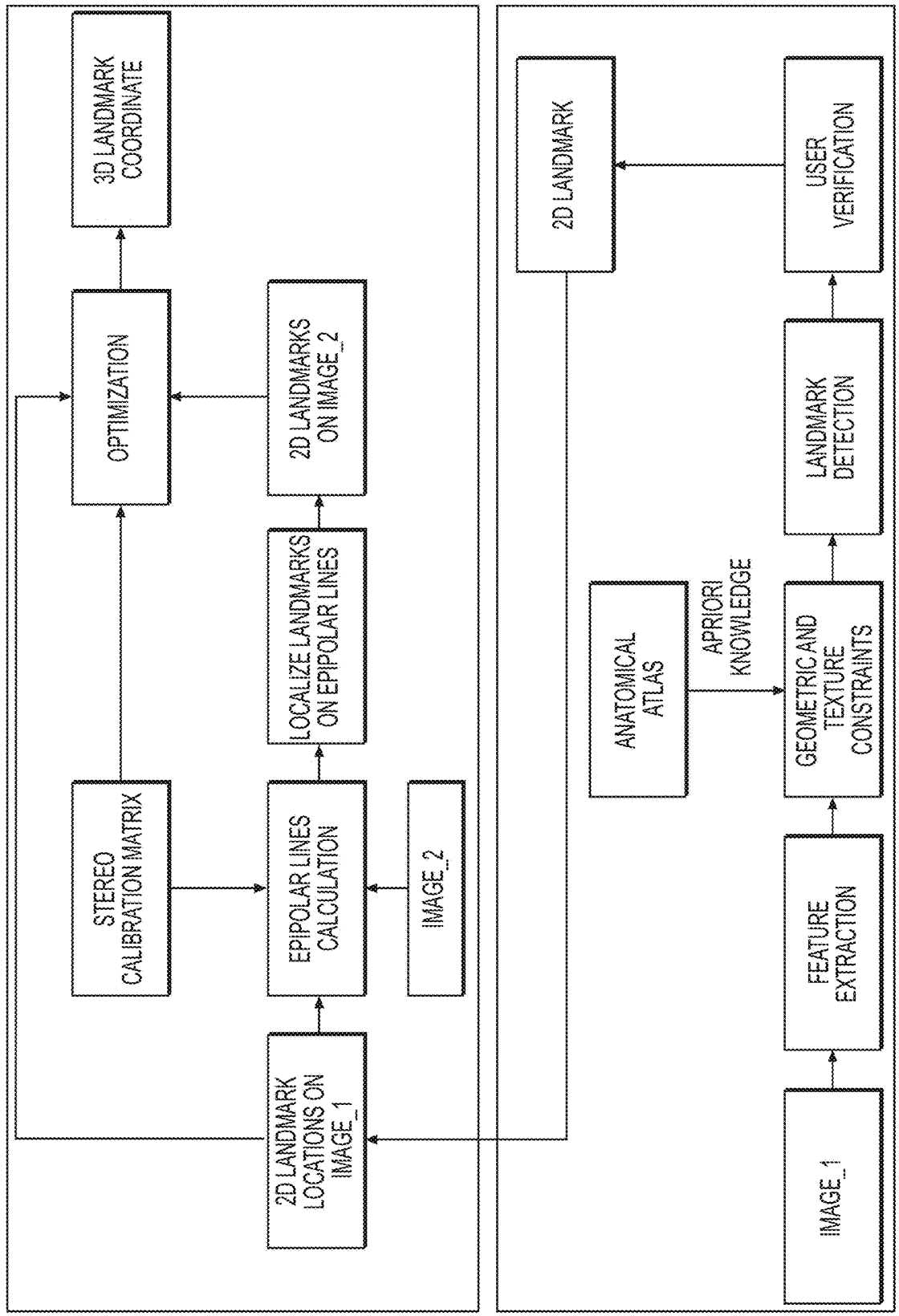
FIG. 55 is an exemplary flow diagram depicting an exemplary process for identifying three dimensional landmarking from "n" number of two dimensional stereo images, in accordance with the instant disclosure.
Figure 56:
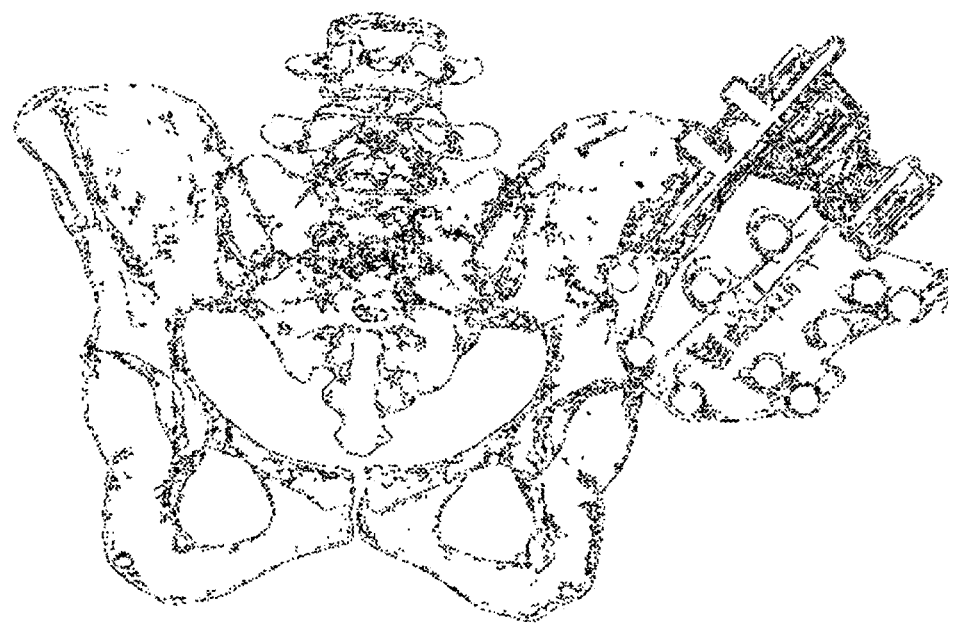
FIG. 56 is an exemplary graphical depiction reflecting anatomical surface edge detection of a pelvis having been extracted from an AP radiographic image of the pelvis.

In this exemplary disclosure, landmarking comprises a process of extracting relevant surgical landmarks that may be necessary for the placement of the implant from calibrated 2D images. A flow chart of the process is explained in FIG. 55. In exemplary form, a set of 2D landmarks may be identified on a first 2D image, for example the points may include left and right ASIS and pubic tubercle points on AP image. Initial position of those landmarks on image may be identified using an automatic algorithm that utilizes feature points extracted from 2D image(s) along with population statistics extracted from statistical anatomical atlas to calculate loci of those landmarks that my then be constrained, for example, using edge and/or texture information and relative positions of those landmarks to calculate a landmark's position (see FIG. 60).

Figure 57:
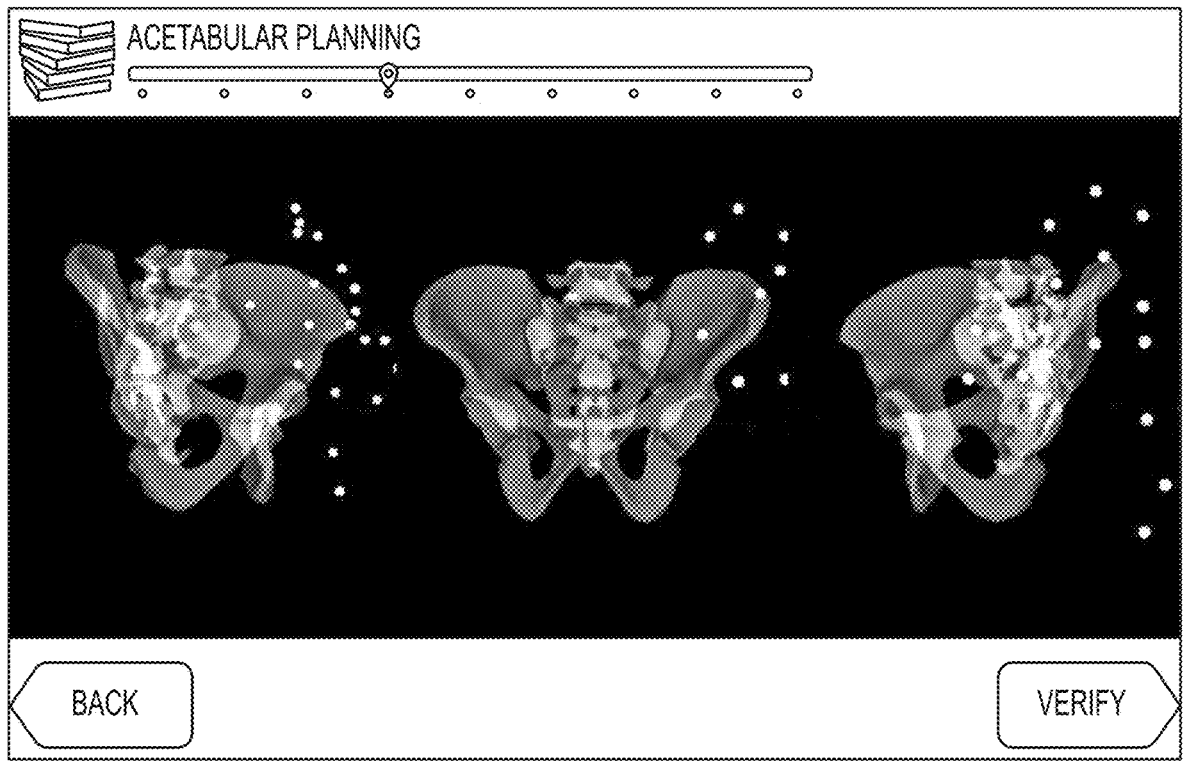
FIG. 57 is a graphical interface view of an exemplary user interface for generation of three dimensional landmarks from two dimensional stereo images in accordance with the instant disclosure.

Extracted 2D landmarks on the first image may then be utilized along with the stereo calibration matrix to create an epi polar line for each landmark on a second or subsequent image. Location of the landmark on the first image along with its location on an epipolar line on the second image may then be fed to an optimization algorithm that may extract the 3D position of the landmarks in the calibration target or imagine coordinate system (see FIG. 57). Those familiar with multi-view geometry will understand there are numerous well known methods to determine 3D positions from calibrated 2D images of the same scene that are all within the scope of the instant disclosure.

XI. Intraoperative Planning from Intraoperative Landmarking

Figure 58:
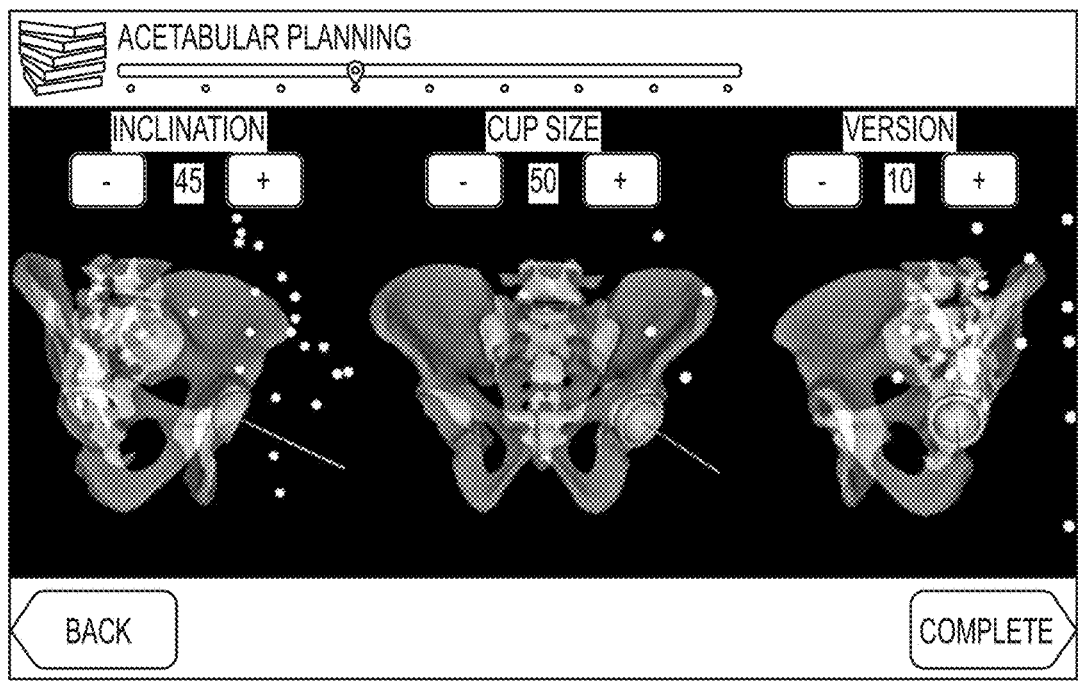
FIG. 58 is an exemplary screen shot taken from a user interface of showing multiple views of a virtual 3D model of a pelvis and reflecting implantation of an orthopedic cup, where the user interface is utilized for intraoperative surgical planning using extracted 3D landmarks from intraoperative stereo images.

In accordance with the instant disclosure, 3D landmarks may be extracted from calibrated intraoperative images and may be used to calculate relevant surgical axes and dimensions. In the context of a pelvis, this may include the right and left ASIS and the pubic tubercle points to compute the anterior posterior plane, SI, anterior-posterior (AP) and medial-lateral (ML) directions and/or the anatomical acetabular cup center and dimensions. A surgical planning interface may then be presented to a user that allows selection of desired implant sizes and orientations (see FIG. 58).

Following from the above description, it should be apparent to those of ordinary skill in the art that, while the methods and apparatuses herein described constitute exemplary embodiments of the present invention, the invention described herein is not limited to any precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A method of tracking motion of a body part, the method comprising:
   gathering motion data from a body part, the body part having mounted thereto a motion sensor;
   gathering a plurality of radiographic images taken of the body part while the body part is in different positions, the plurality of radiographic images having the body part and the motion sensor within a field of view; and,
   constructing a virtual three dimensional model of the body part from the plurality of radiographic images using a structure of the motion sensor identifiable within at least two of the plurality of radiographic images to calibrate the radiographic images.

2. The method of claim 1, wherein the motion sensor comprises an inertial measurement unit.

3. The method of claim 2, wherein the inertial measurement unit comprises a plurality of accelerometers, a plurality of gyroscopes, and a plurality of magnetometers.

4. The method of claim 1, where the motion sensor is mounted rigidly to the body part.

5. The method of claim 1, wherein the radiographic image comprises an X-ray.

6. The method of claim 1, wherein the radiographic image comprises a fluoroscopic image.

7. The method of claim 1, wherein calibrating the radiographic images is performed automatically.

8. The method of claim 7, wherein the automatic calibration of the radiographic images is performed by a computer running a software program.

9. The method of claim 1, further comprising:
   gathering data from the motion sensor that may be used to determine at least one of position and rotation of the motion senor as a function to time.

10. The method of claim 9, wherein the data gathered from the motion sensor is gathered wirelessly.

11. The method of claim 9, wherein the data gathered from the motion sensor is gathered from a wire connected to the motion sensor.

12. The method of claim 1, wherein gathering the motion data includes recording at least one of changes in position and rotation of the motion sensor as a function of time.

13. The method of claim 1, wherein gathering the motion data includes recording changes in acceleration of the motion sensor as a function of time.

* * * * *